United States Patent
Castro Pineiro et al.

(10) Patent No.: US 7,598,386 B2
(45) Date of Patent: Oct. 6, 2009

(54) SULPHONES WHICH MODULATE THE ACTION OF GAMMA-SECRETASE

(75) Inventors: Jose Luis Castro Pineiro, Bishops Stortford (GB); Ian Churcher, Great Dunmow (GB); Kevin Dinnell, Much Hadham (GB); Timothy Harrison, Great Dunmow (GB); Sonia Kerrad, Huningue (GB); Alan John Nadin, Sawbridgeworth (GB); Paul Joseph Oakley, South Benfleet (GB); Andrew Pate Owens, Huntingdon (GB); Duncan Edward Shaw, Bishops Stortford (GB); Martin Richard Teall, Bishops Stortford (GB); Susannah William, Basingstoke (GB); Brian John Williams, Great Dunmow (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 0 days.

(21) Appl. No.: 11/788,888

(22) Filed: Apr. 23, 2007

(65) Prior Publication Data

US 2007/0213329 A1 Sep. 13, 2007

Related U.S. Application Data

(62) Division of application No. 10/473,727, filed as application No. PCT/GB01/03471 on Aug. 29, 2001, now abandoned.

(30) Foreign Application Priority Data

Apr. 5, 2001 (GB) .................................. 0108591.9

(51) Int. Cl.
*C07D 211/00* (2006.01)
*C07D 211/68* (2006.01)
*C07D 211/40* (2006.01)
*C07D 211/70* (2006.01)
*C07D 309/00* (2006.01)

(52) U.S. Cl. ...................... 546/184; 546/193; 546/216; 546/348; 549/356

(58) Field of Classification Search ........................ None
See application file for complete search history.

(56) References Cited

U.S. PATENT DOCUMENTS

| 2,802,013 | A | | 8/1957 | Dodson et al. |
|---|---|---|---|---|
| 2,812,330 | A | * | 11/1957 | Dodson ...................... 546/219 |
| 2,813,100 | A | * | 11/1957 | Levy .......................... 546/185 |
| 5,703,129 | A | | 12/1997 | Felsenstein et al. |
| 2003/0114496 | A1 | | 6/2003 | Churcher et al. |
| 2004/0082617 | A1 | | 4/2004 | Harrison et al. |
| 2004/0121995 | A1 | | 6/2004 | Churcher et al. |
| 2004/0122050 | A1 | | 6/2004 | Churcher et al. |
| 2004/0171683 | A1 | | 9/2004 | Castro Pineiro |
| 2004/0230054 | A1 | | 11/2004 | Dinnell et al. |
| 2005/0075320 | A1 | | 4/2005 | Nadin et al. |

FOREIGN PATENT DOCUMENTS

| CA | 2 473 374 | | 7/2003 |
|---|---|---|---|
| DE | 735866 | * | 4/1943 |
| EP | 0 863 134 | | 9/1998 |
| EP | 1 466 898 | | 10/2004 |
| JP | 56-026847 | | 3/1981 |
| JP | 56025149 | | 3/1981 |
| JP | 56026866 | | 3/1981 |
| WO | WO 00/50391 | | 8/2000 |
| WO | WO 02/081433 | | 10/2002 |
| WO | WO 02/081435 | | 10/2002 |
| WO | WO 03/055850 | | 7/2003 |
| WO | WO 03/059335 | | 7/2003 |
| WO | WO 2004/013090 | | 2/2004 |
| WO | WO 2004/031137 | | 4/2004 |
| WO | WO 2004/031138 | | 4/2004 |
| WO | WO 2004/031139 | | 4/2004 |
| WO | WO 2004/048321 | | 6/2004 |
| WO | WO 2004/101538 | | 11/2004 |
| WO | WO 2004/101539 | | 11/2004 |
| WO | WO 2005/000798 | | 1/2005 |

OTHER PUBLICATIONS

Trost et al. J. Org. Chem. (1999), (64)15, 5427-5435.*
CAS online citation 52:35523 [retrieved Nov. 28, 2008] from STN; Columbus, OH, USA.*
O. Eisleb, "Neue Synthesin mit Natriumamids", Berichte Der Deutschen Chemischen Gesellschaft, vol. 74, No. 8, pp. 1433-1450 (1941).
P. Kisanga et al., "Development, Synthetic Scope, and Mechanistic Studies of the Palladium Catalyzed Cycloisomerization of Functionalized 1,6-Dienes in the Presence of Silane", J. Am. Chem. Soc., vol. 122, No. 41, pp. 10017-10026 (2000).

(Continued)

*Primary Examiner*—Karl J Puttlitz
(74) *Attorney, Agent, or Firm*—William Kronatin; Raynard Yuro

(57) ABSTRACT

Novel sulphones of Formula I are disclosed:

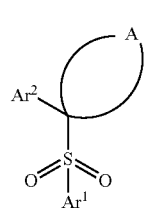

wherein A completes a 4-7 membered ring optionally comprising up to two heteroatoms. The compounds modulate the action of γ-secretase and are therefore useful in the treatment or prevention of Alzheimer's disease.

5 Claims, No Drawings

OTHER PUBLICATIONS

L. Capuano et al., "Neue Synthesen mit Diazodiketonen, IV. Cyclische S-Oxide", Chemische Berichte, vol. 112, No. 3, pp. 1012-1022 (1979).

T. Okuyama et al., "Flash Photolytic Generation of a Dithio Carbocation from 1,3-Dithiolane Derivatives and Its Reaction with Nucleophiles", Bull. Chem. Soc. Jpn., vol. 64, No. 9, pp. 2751-2756 (1991).

J. Golinski et al., "Reactions of Organic Anions; XCIV. Catalytic Two-Phase Alkylation of Benzyl Sulfones and Sulfonamides", Synthesis, No. 6, pp. 461-463 (1979).

C. Koradin et al., "Cesium Catalyzed Addition of Nitriles to Alkynes", Synlett, No. 10, pp. 1452-1454 (2000).

J. M. Decesare et al., "Gamma and delta-epoxy sulfones. Formation of different ring-sized products upon reaction with CH MgI or LiN[CH(CH )]", Canadian Journal of Chemistry, vol. 59, No. 10, pp. 1415-1424 (1981).

J. P. Scott et al., "Expedient Diels-Alder assembly of 4-aryl-4-phenylsulfonyl cycolhexanones", Tetrahedron Letters, vol. 45, pp. 3345-3348 (2004).

E. W. Garbisch et al., "On the Mechanism of Benzylic Substituent Hydrogenolysis", Journal of the American Chemical Society, vol. 89(16), pp. 4233-4235 (1967).

R. K. Norris et al., "An Example of Substitution Proceeding with Retention in the SRN1 Reaction. Trapping of a Pyramidal Benzylic Radical by Benzenethiolate Ion", J. of the Chem. Soc. Chem. Comm., Issue 3, pp. 79-80 (1981).

R.K. Norris et al., "The Stereochemistry of the S N1 Reaction in Some Cyclohexane Derivatives", Tetrahedron, vol. 38, No. 8, pp. 1051-1057 (1982).

M. Mokosza et al., "Ambiphilic Reactivity of 2,4-Dinitrobenzyl p-Tolyl Sulfone Carbanion" Polish J. Chem., vol. 72, pp. 1198-1201 (1998).

B. Corbel et al., Database Abstract 89:42507, "Preparation of Cyclobutenones and Cyclopent-2Oenones via Epoxy Sulfone Cyclizations", Canadian Journal of Chemistry (1978), 56 (4), 505-511.

M. Makosza et al. Database Abstract 105:225979, "Reactions of organic Anions. 133. Alkylation and the Knoevenagel Condensation of Nitrobenzylic Sulfones and Nitriles", Synthetic Communications, 1986, 16 (4), 419-423.

Co-pending U.S. Appl. No. 12/151,296, filed on May 6, 2008.

US Office Action Dated Jul. 29, 2008 for Co-pending U.S. Appl. No. 12/151,296, filed on May 6, 2008.

* cited by examiner

SULPHONES WHICH MODULATE THE ACTION OF GAMMA-SECRETASE

CROSS-REFERENCE TO RELATED APPLICATIONS

This application is a divisional of U.S. patent application Ser. No. 10/473,727, filed Oct. 1, 2003, now abandoned which is the U.S. national phase of International Patent Application No. PCT/GB01/03471, filed Aug. 29, 2001, which claims priority under 35 U.S.C. § 119(e) from Great Britain Application No. 0108591.9, filed Apr. 5, 2001.

The present invention relates to a novel class of compounds, their salts, pharmaceutical compositions comprising them, processes for making them and their use in therapy of the human body. In particular, the invention relates to novel sulphones which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2):1-7; ID *research alert* 1997 2(1):1-8; Current Opinion in CPNS Investigational Drugs 1999 1(3):327-332; and Chemistry in Britain, January 2000, 28-31.)

Aβ is a peptide comprising 39-43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

Japanese Patent Publication No. 56 026847 discloses certain 4-aryl-4-arylsulphonylcyclohexanone derivatives as intermediates in the synthesis of substituted salicylic acids.

The present invention provides a novel class of non-peptidic compounds which are useful in the treatment or prevention of AD by modulating the processing of APP by the putative γ-secretase, thus arresting the production of Aβ.

The present invention provides a pharmaceutical composition comprising, in a pharmaceutically acceptable carrier, a compound of formula I:

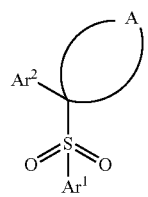

wherein:

A represents the atoms necessary to complete a saturated or unsaturated ring containing 4, 5, 6 or 7 ring atoms, at most 2 of which are selected from nitrogen, oxygen and sulphur, the remainder being carbon, said ring bearing, in addition to $Ar^2$ and $Ar^1 SO_2$, 0-3 substituents independently selected from =X, halogen, CN, $NO_2$, $N_3$, $R^2$, $CF_3$, $N(R^1)_2$, $OR^1$, $COR^1$, $CO_2R^1$, $CON(R^1)_2$, $OCOR^1$, $OCO_2R^2$, $OCON(R^1)_2$, $N(R^1)COR^2$, $N(R^1)CO_2R^2$, $OSO_2R^2$ and $N(R^1)SO_2R^2$;

X represents $C(R^1)_2$, $CHCO_2R^1$, O, S, $NOR^1$, $CHCON(R^1)_2$, $NNHCOR^2$, or the atoms necessary to complete a spiro-linked 5- or 6-membered carbocyclic or heterocyclic ring;

$Ar^1$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$R^1$ represents H or $R^2$, or two $R^1$ groups together with a nitrogen atom to which they are mutually attached may complete an N-heterocyclyl group bearing 0-3 substituents selected from =O, =S, =$NOR^1$, halogen, CN, $NO_2$, $R^2$, $CF_3$, $N(R^{1a})_2$, $OR^1$, $COR^1$, $CO_2R^1$ and $CON(R^{1a})_2$;

$R^{1a}$ represents H or $R^2$, or two $R^{1a}$ groups together with a nitrogen atom to which they are mutually attached may complete an N-heterocyclyl group bearing 0-3 substituents selected from =O, =S, halogen, $C_{1-4}$alkyl CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, Ar and COAr;

$R^2$ represents $C_{1-6}$alkyl, $C_{3-9}$cycloalkyl, $C_{3-6}$cycloalkyl $C_{1-6}$alkyl, $C_{2-6}$alkenyl, $C_{2-6}$alkynyl or C-heterocyclyl, any of which may bear up to 3 substituents independently selected from halogen, CN, $NO_2$, $N_3$, $CF_3$, $OR^{2a}$, $N(R^{2a})_2$, $CO_2R^{2a}$, $COR^{2a}$, $OCOR^{2a}$, $CON(R^{2a})_2$, $OCON(R^{2a})_2$, $CONR^{2a}$ ($OR^{2a}$), CONHC(=NOH)$R^{2a}$, $CON(R^{2a})N(R^{2a})_2$, heterocyclyl, phenyl and heteroaryl, said heterocyclyl, phenyl and heteroaryl substituents themselves bearing 0-3 substituents selected from halogen, CN, $NO_2$, $CF_3$, $OR^{2a}$, $N(R^{2a})_2$, $CO_2R^{2a}$, $COR^{2a}$, $CON(R^{2a})_2$ and $C_{1-4}$alkyl; or $R^2$ represents Ar; or 2 $OR^2$ groups attached to adjacent carbon atoms may complete a 1,3-dioxolane ring;

$R^{2a}$ represents H, $C_{1-6}$-alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, $OR^{2b}$, $CO_2R^{2b}$, $N(R^{2b})_2$, $CON(R^{2b})_2$, Ar and COAr; or $R^{2a}$ represents Ar; or two $R^{2a}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

$R^{2b}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr; or $R^{2b}$ represents Ar; or two $R^{2b}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

In a subset of the compounds of formula I,

A represents the atoms necessary to complete a saturated or unsaturated ring containing 5, 6 or 7 ring atoms, at most 2 of which are selected from nitrogen, oxygen and sulphur, the remainder being carbon, said ring bearing 0-3 substituents independently selected from =C($R^1$)$_2$, =CHCO$_2R^1$, =O, =S, =NOR$^1$, halogen, CN, NO$_2$, N$_3$, R$^2$, CF$_3$, N(R$^1$)$_2$, OR$^1$, COR$^1$, CO$_2$R$^1$, CON(R$^1$)$_2$, OCOR$^1$, OCO$_2$R$^2$, N(R$^1$)COR$^2$, N(R$^1$)CO$_2$R$^2$, OSO$_2$R$^2$ and N(R$^1$)SO$_2$R$^2$;

$Ar^1$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy;

$R^1$ represents H or $R^2$, or two $R^1$ groups together with a nitrogen atom to which they are mutually attached may complete an N-heterocyclyl group bearing 0-3 substituents selected from =O, =S, =NOR$^1$, halogen, CN, NO$_2$, R$^2$, CF$_3$, N(R$^{1a}$)$_2$, OR$^1$, COR$^1$, CO$_2$R$^1$ and CON(R$^{1a}$)$_2$;

$R^{1a}$ represents H or $R^2$, or two $R^{1a}$ groups together with a nitrogen atom to which they are mutually attached may complete an N-heterocyclyl group bearing 0-3 substituents selected from =O, =S, halogen, $C_{1-4}$alkyl CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, Ar and COAr;

$R^2$ represents $C_{1-6}$alkyl, $C_{3-9}$cycloalkyl, $C_{3-6}$cycloalkyl $C_{1-6}$alkyl, $C_{2-6}$alkenyl, $C_{2-6}$alkynyl or C-heterocyclyl, any of which may bear a substituent selected from halogen, CN, $NO_2$, $CF_3$, $OR^{2a}$, $N(R^{2a})_2$, $CO_2R^{2a}$, $COR^{2a}$, $CON(R^{2a})_2$, heterocyclyl, phenyl and heteroaryl, said heterocyclyl, phenyl and heteroaryl substituents themselves bearing 0-3 substituents selected from halogen, CN, $NO_2$, $CF_3$, $OR^{2a}$, $N(R^{2a})_2$, $CO_2R^{2a}$, $COR^{2a}$, $CON(R^{2a})_2$ and $C_{1-4}$alkyl, or $R^2$ represents Ar;

$R^{2a}$ represents H, $C_{1-4}$alkyl, or Ar; or two $R^{2a}$ groups together with a nitrogen atom to which they are mutually attached may complete an N-heterocyclyl group bearing 0-3 substituents selected from =O, =S, halogen, $C_{1-4}$alkyl CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, Ar and COAr; and Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl.

The invention further provides a compound of formula I or a pharmaceutically acceptable salt thereof, with the proviso that if A represents —$CH_2$—CH($CO_2R$)—CO—$CH_2CH_2$— or —CH=C($CO_2R$)—CO—$CH_2CH_2$—, where R represents methyl, ethyl, n-propyl or n-butyl, and $Ar^1$ represents phenyl, 4-methylphenyl or 4-chlorophenyl, then $Ar^2$ does not represent phenyl, 4-halophenyl or 2,4-dihalophenyl where the halogens are independently Cl or F.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl $C_{1-6}$alkyl", "$C_{2-6}$alkynyl" and "$C_{1-6}$alkoxy" are to be construed in an analogous manner.

The expression "$C_{3-9}$cycloalkyl" as used herein refers to nonaromatic monocyclic or fused bicyclic hydrocarbon ring systems comprising from 3 to 9 ring atoms. Examples include cyclopropyl, cyclobutyl, cyclopentyl, cyclohexyl, cyclohexenyl and bicyclo[2.2.1]heptyl.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "$C_{6-10}$aryl" as used herein includes phenyl and naphthyl.

The expression "heterocyclyl" as used herein means a cyclic or polycyclic system of up to 10 ring atoms selected from C, N, O and S, wherein none of the constituent rings is aromatic and wherein at least one ring atom is other than carbon. Preferably not more than 3 ring atoms are other than carbon. Examples of heterocyclyl groups include azetidinyl, pyrrolidinyl, terahydrofuryl, piperidinyl, piperazinyl, morpholinyl, thiomorpholinyl, imidazolidinyl, oxazolidinyl, thiazolidinyl, 2,5-diazabicyclo[2.2.1]heptyl, 2-aza-5-oxabicyclo[2.2.1]heptyl and 1,4-dioxa-8-azaspiro[4,5]decanyl. Unless otherwise indicated, heterocyclyl groups may be bonded through a ring carbon atom or a ring nitrogen atom where present. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and wherein at least one ring atom is other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds in accordance with the invention may exist as enantiomers by virtue of the asymmetry of the molecule as a whole. It is to be understood that in such cases both enantiomers, and mixtures thereof in any proportion, are included within the scope of the invention, and that structural formulae depicting molecules of this type shall be representative of both of the possible enantiomers, unless otherwise indicated.

In the compounds of formula I, A completes a saturated or unsaturated ring system containing 4, 5, 6 or 7 ring atoms, at most 2 of which are selected from nitrogen, oxygen or sulphur, the remainder being carbon, which optionally bears up to 3 additional substituents as defined previously. Preferably, A completes a 4-, 5-, 6-, or 7-membered ring in which at most 1 ring atom is oxygen or nitrogen and the remainder carbon, and in certain embodiments when A completes a 4-membered ring, said ring is carbocyclic. Examples of rings completed by A include cycloheptane, cyclohexane, cyclohexene, cyclopentane, cyclopentene, cyclobutane, piperidine, pyrrolidine and pyran, with cycloheptane, cyclohexane, cyclohexene, cyclopentane, cyclopentene and pyran preferred.

The ring completed by A may bear up to 3 substituents in addition to those shown in formula I, but when A completes a 4-membered ring, said ring typically bears at most 2 additional substituents, preferably at most 1 additional substituent. Where three additional substituents are present, two of them are preferably attached to the same ring carbon atom. Preferred substituents include =X; halogen; azide; hydroxy or alkoxy represented by $OR^1$; alkylsulphonyloxy represented by $OSO_2R^2$; amino or N-heterocyclyl represented by $N(R^1)_2$; optionally substituted alkyl, alkenyl, aryl or heteroaryl represented by $R^2$; carboxylic acid or alkoxycarbonyl represented by $CO_2R^1$; carbamoyl represented by $CON(R^1)_2$; carbamoyloxy represented by $OCON(R^1)_2$; and amido represented by $N(R^1)COR^2$.

When A completes a cyclobutyl ring, it is aptly substituted by $OR^1$.

When the ring completed by A bears one additional substituent which is connected to the ring by a single bond, that substituent may be either cis or trans with respect to the $Ar^1SO_2$ group, but the cis configuration is preferred.

Typical embodiments of =X include alkylidene represented by $=C(R^1)_2$, $=CHCON(R^1)_2$ or $=CHCO_2R^1$; oxo represented by =O; oximino or alkoximino represented by $=NOR^1$; $=N-NHCOR^2$; or the atoms necessary to complete a spiro-linked 5- or 6-membered carbocyclic or heterocyclic ring such as:

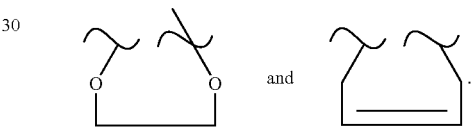

In certain embodiments, the ring positions adjacent to the carbon bonded to the $Ar^1SO_2$ group are occupied by unsubstituted methylene groups.

Examples of fragments represented by A include, but are not limited to: $-(CH_2)_n-$, $-(CH_2)_pCH=CH(CH_2)_q-$, $-(CH_2)_r-O-(CH_2)_s-$, $-(CH_2)_r-NR^1-(CH_2)_n-$, $-(CH_2)_r-CF_2-(CH_2)_s-$, $-(CH_2)_r-CR^1R^2-(CH_2)_s-$,

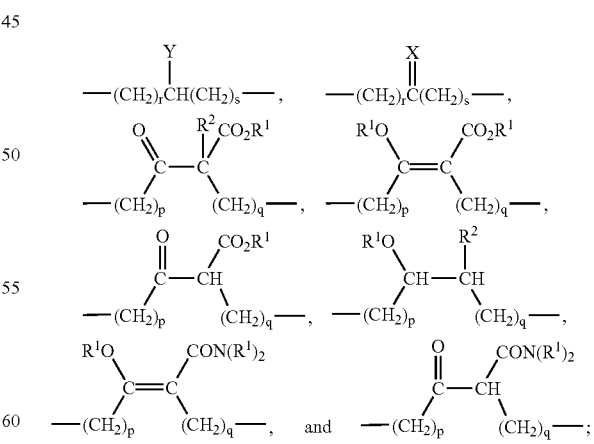

where n is an integer in the range 4-6;

p and q are both 0-4 such that p+q is an integer in the range 2-4;

r and s are 0-5 such that r+s is an integer in the range 2-5, and

Y represents $OR^1$, $N(R^1)_2$, $N(R^1)COR^2$, $OCOR^2$, $OCON(R^1)_2$, $CO_2R^1$, $CON(R^1)_2$ or CN.

Preferably, each of p, q, r and s is at least 1.

Preferably, p+q is 2 or 3, most preferably 3.

Preferably, r+s is 3 or 4, most preferably 4.

$R^1$ represents H or $R^2$, or two $R^1$ groups together with a nitrogen atom to which they are mutually attached may complete an N-heterocyclyl group. Examples of N-heterocyclyl groups represented by $N(R^1)_2$ include pyrrolidin-1-yl, piperidin-1-yl, piperazin-1-yl, morpholin-4-yl, thiomorpholin-4-yl and 1,4-dioxa-8-azaspiro[4,5]decan-8-yl, each optionally bearing up to 3 substituents as defined previously. Preferably, such heterocyclyl groups bear at most 2 substituents selected from =O, $CF_3$, OH, $R^2$, $CO_2R^1$ and $N(R^{1a})_2$.

$R^{1a}$ represents H or $R^2$, or two $R^{1a}$ groups together with a nitrogen atom to which they are mutually attached may complete an N-heterocyclyl group, optionally substituted as defined previously, an example being piperidin-1-yl.

$R^2$ represents $C_{1-6}$alkyl, $C_{3-9}$cycloalkyl, $C_{3-6}$cycloalkyl$C_{1-6}$alkyl, $C_{2-6}$alkenyl, $C_{2-6}$alkynyl or C-heterocyclyl (any of which is optionally substituted as defined previously), or Ar. Alternatively, two $OR^2$ groups attached to adjacent carbon atoms may complete a 1,3-dioxolane ring such as 2,2-dimethyl-1,3-dioxolane. Preferred substituents on groups represented by $R^2$ include CN, phenyl, heteroaryl (such as imidazolyl, furyl, thiazolyl, pyrazolyl, thiadiazolyl, oxadiazolyl, triazolyl, tetrazolyl and pyridyl), C-heterocyclyl (such as 1-t-butoxycarbonylpyrrolidin-2-yl), $COR^{2a}$, $OR^{2a}$, $N(R^{2a})_2$, $CO_2R^{2a}$, $CON(R^{2a})_2$, $OCON(R^{2a})_2$, $CONR^{2a}(OR^{2a})$, and $CON(R^{2a})N(R^{2a})_2$. Typically, not more than 2 substituents are present on $R^2$.

$R^{2a}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent as defined previously; or $R^{2a}$ represents Ar; or two $R^{2a}$ groups together with a nitrogen atom to which they are mutually attached may complete an N-heterocyclyl group which is optionally substituted as defined previously. Particular values of $R^{2a}$ include H, aryl (such as phenyl), heteroaryl (such as pyridyl), $C_{3-6}$cycloalkyl (such as cyclopropyl, cyclobutyl and cyclopentyl), $C_{3-6}$cycloalkyl$C_{1-6}$alkyl (such as cyclopropylmethyl), $C_{2-6}$alkenyl (such as allyl), and linear or branched $C_{1-6}$alkyl which is optionally substituted with $CF_3$, Ar, $OR^{2b}$, $N(R^{2b})_2$, $CO_2R^{2b}$ or $CON(R^{2b})_2$.

Examples of N-heterocyclyl groups represented by $N(R^{2a})_2$ include piperidin-1-yl (optionally substituted with OH, $CO_2H$, $CO_2C_{1-4}$alkyl, Me or Ph), piperazin-1-yl (optionally substituted with Me or Ph), morpholin-4-yl, thiomorpholin-4-yl, 1,1-dioxo-thiomorpholin-4-yl, 2-oxo-imidazolidin-1-yl, 5,5-dimethyl-2,2-dioxo-oxazolidin-3-yl, 2,5-dioxo-imidazolidin-1-yl, 2-oxo-oxazolidin-3-yl, 2-oxo-pyridin-1-yl, and 2-oxo-pyrrolidin-1-yl.

$R^{2b}$ typically represents H or $C_{1-4}$alkyl.

Typically, $R^2$ represents $C_{2-6}$alkenyl (such as allyl) or $C_{1-6}$alkyl, such as methyl, ethyl, n-propyl or t-butyl, which is optionally substituted as described above.

$Ar^1$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy. Preferably, $Ar^1$ represents optionally substituted phenyl or heteroaryl. Typical heteroaryl embodiments of $Ar^1$ include optionally substituted pyridyl, in particular optionally substituted 3-pyridyl. Preferably, $Ar^1$ bears 0-2 substituents, more preferably 1 or 2 substituents, and most preferably 1 substituent which is preferably in the para-position relative to the sulphone group. Typical substituents include halogen (especially chlorine, bromine and fluorine), $C_{1-4}$alkyl (such as methyl), $C_{1-4}$alkoxy (such as methoxy), and $CF_3$. Examples of groups represented by $Ar^1$ include 4-chlorophenyl, 4-bromophenyl, 4-fluorophenyl, 4-trifluoromethylphenyl, 4-methylphenyl, 3,4-difluorophenyl, 3,4-dichlorophenyl, 4-methoxyphenyl and 6-chloro-3-pyridyl. Most preferably, $Ar^1$ represents 4-chlorophenyl, 4-bromophenyl or 4-trifluoromethylphenyl.

$Ar^2$ represents $C_{6-10}$aryl or heteroaryl bearing 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy. Preferably, $Ar^2$ represents phenyl bearing 1 or 2 substituents as indicated, and most preferably, $Ar^2$ represents 2,5-disubstituted phenyl. Preferred substituents include halogen (especially bromine, chlorine and fluorine) and substituted alkyl, such as hydroxymethyl. Examples of groups represented by $Ar^2$ include 2,5-dichlorophenyl, 2,5-difluorophenyl, 2-bromo-5-fluorophenyl, 5-bromo-2-fluorophenyl, 5-iodo-2-fluorophenyl and 2-hydroxymethyl-5-fluorophenyl. Very aptly, $Ar^2$ represents 2,5-difluorophenyl.

A subclass of the compounds of the invention comprises the compounds of formula II:

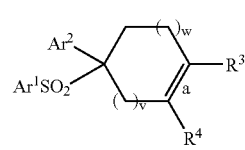

and the pharmaceutically acceptable salts thereof, wherein
v is 1 and w is 0, 1 or 2, or v is 2 and w is 0 or 1;
bond a (indicated by the dotted line) may be single or double;
$R^3$ represents H, $OR^1$, $N(R^1)_2$ or $N(R^1)COR^2$;
$R^4$ represents H, $R^2$, $OR^1$, $OCOR^2$, CN, $CO_2R^1$ or $CON(R^1)_2$;
and $Ar^1$, $Ar^2$, $R^1$ and $R^2$ have the same meanings as before.

When $R^3$ represents $N(R^1)_2$ or $N(R^1)COR^2$, bond a is preferably single and $R^4$ is preferably H.

When bond a is single, $R^3$ may be cis or trans relative to $Ar^1SO_2$—, but is preferably cis.

Examples of compounds within this subclass include those wherein $Ar^1$ represents 4-chlorophenyl, $Ar^2$ represents 2,5-difluorophenyl, v is 1 and w, a, $R^3$ and $R^4$ are as indicated in the following table:

| w | Bond a | $R^3$ | $R^4$ |
|---|--------|-------|-------|
| 0 | Single | H | H |
| 0 | Double | H | H |
| 0 | Single | OH | H |
| 1 | Single | H | H |
| 1 | Double | H | H |
| 1 | Single | OH | H |
| 1 | Double | OH | $CO_2Me$ |
| 1 | Double | O-allyl | $CO_2Me$ |
| 1 | Double | O—$CH_2Ph$ | $CO_2Me$ |
| 1 | Single | OH | $CH_2OH$ |
| 1 | Double | OMe | $CO_2Me$ |
| 1 | Double | OH | $CONH_2$ |
| 1 | Single | $NH_2$ | H |
| 1 | Single | $NMe_2$ | H |

-continued

| w | Bond a | R³ | R⁴ |
|---|---|---|---|
| 1 | Single | NHCH₂Ph | H |
| 1 | Single | morpholin-4-yl | H |
| 1 | Single | thiomorpholin-4-yl | H |
| 1 | Single | NHCH₂CO₂Me | H |
| 1 | Single | 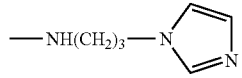 | H |
| 1 | Single | 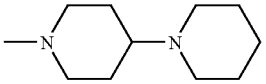 | H |
| 1 | Single | 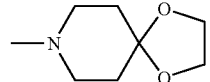 | H |
| 1 | Single | 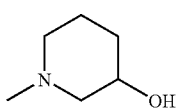 | H |
| 1 | Single | 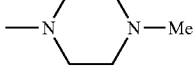 | H |
| 1 | Single | 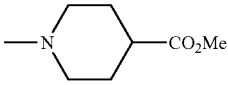 | H |
| 1 | Single | 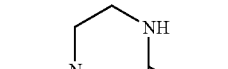 | H |
| 1 | Single | 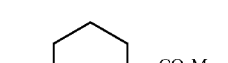 | H |
| 1 | Single | 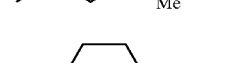 | H |
| 1 | Single | 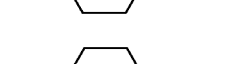 | H |
| 1 | Single | 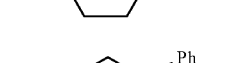 | H |
| 1 | Single | 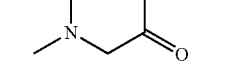 | H |
| 1 | Single | —NHCH(Me)CO₂Me | H |
| 1 | Single | 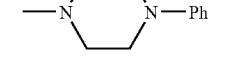 | H |

-continued

| w | Bond a | R³ | R⁴ |
|---|---|---|---|
| 1 | Single | 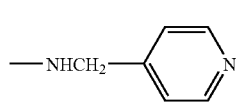 | H |
| 1 | Single | 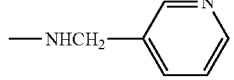 | H |
| 1 | Single | 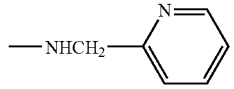 | H |
| 1 | Single | 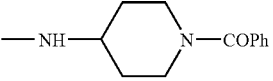 | H |
| 1 | Single | 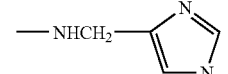 | H |
| 1 | Single | 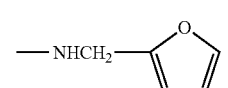 | H |
| 1 | Single | —NHCO(CH₂)₃NMe₂ | H |
| 1 | Single | 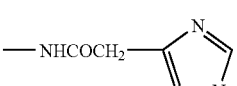 | H |
| 1 | Single | —NHCOCH₂NMe₂ | H |
| 1 | Single | —NHCOPh | H |
| 1 | Single | —NHCOMe | H |
| 1 | Single | NHCH₂CH₂OH | H |
| 1 | Single | NHCH(CONH₂)CH₂CH(Me)₂ | H |
| 1 | Single | NHCH₂CONH₂ | H |
| 1 | Single | OMe | H |
| 2 | Double | H | H |
| 2 | Single | H | H |
| 2 | Single | morpholin-4-yl | H |
| 1 | Single | H | OH |
| 1 | Single | H | OCOMe |
| 1 | Single | H | OEt |
| 1 | Single | H | O-allyl |
| 1 | Single | —O—C(Me)₂—O— | |
| 1 | Single | OH | OH |
| 1 | Single | OCH₂CONH₂ | H |
| 1 | Single | OCH₂CO₂H | H | and pharmaceutically acceptable salts thereof.

A subset of the compounds of formula II are those in which v is 2, bond a is single and R³ is H. Particular examples of compounds within this subset include those in which w is 0 and Ar¹, Ar² and R⁴ have the identities shown in the following table:

| Ar¹ | Ar² | R⁴ |
|---|---|---|
| 3,4-di-Cl—C₆H₃ | 2,5-di-F—C₆H₃ | H |
| 4-Cl—C₆H₄ | 2-F—C₆H₄ | H |
| 4-Cl—C₆H₄ | 2,5-di-F—C₆H₃ | CO₂Me |
| 4-Cl—C₆H₄ | 2,5-di-F—C₆H₃ | OCOMe |

-continued

| Ar¹ | Ar² | R⁴ |
|---|---|---|
| 4-Cl—C₆H₄ | 2,5-di-F—C₆H₃ | 1,2,3-triazol-1-yl |
| 4-Br—C₆H₄ | 2,5-di-F—C₆H₃ | H |
| 4-F—C₆H₄ | 2,5-di-F—C₆H₃ | H |
| 4-Cl—C₆H₄ | 2-Br-5-F—C₆H₃ | H |
| 4-Me—C₆H₄ | 2,5-di-F—C₆H₃ | H |
| 4-Cl—C₆H₄ | 2,5-di-F—C₆H₃ | CN |
| 4-(CF₃O)—C₆H₄ | 2,5-di-F—C₆H₃ | H |
| 3-Cl—C₆H₄ | 2,5-di-F—C₆H₃ | H |
| 4-Cl—C₆H₄ | C₆H₅ | H | and pharmaceutically acceptable salts thereof.

In a further subset of the compounds of formula II, v is 2, bond a is single, $R^3$ is H and $R^4$ is $R^2$. Within this subset, there is the group of compounds defined by formula IIA:

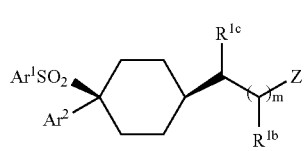

IIA wherein m is 0 or 1;

Z represents halogen, CN, $NO_2$, $N_3$, $CF_3$, $OR^{2a}$, $N(R^{2a})_2$, $CO_2R^{2a}$, $OCOR^{2a}$, $COR^{2a}$, $CON(R^{2a})_2$, $OCON(R^{2a})_2$, $CONR^{2a}(OR^{2a})$, $CON(R^{2a})N(R^{2a})_2$, $CONHC(=NOH)R^{2a}$, heterocyclyl, phenyl or heteroaryl, said heterocyclyl, phenyl or heteroaryl bearing 0-3 substituents selected from halogen, CN, $NO_2$, $CF_3$, $OR^{2a}$, $N(R^{2a})_2$, $CO_2R^{2a}$, $COR^{2a}$, $CON(R^{2a})_2$ and $C_{1-4}$alkyl;

$R^{1b}$ represents H, $C_{1-4}$alkyl or OH;

$R^{1c}$ represents H or $C_{1-4}$alkyl;

with the proviso that when m is 1, $R^{1b}$ and $R^{1c}$ do not both represent $C_{1-4}$alkyl;

and $Ar^1$, $Ar^2$ and $R^{2a}$ have the same meanings as before;

and the pharmaceutically acceptable salts thereof.

When m is 1 and $R^{1b}$ is OH, Z preferably represents optionally substituted phenyl or heteroaryl.

In the compounds of formula IIA, $Ar^1$ is typically selected from phenyl groups substituted in the 4-position with halogen, methyl or trifluoromethyl and phenyl groups substituted in the 3- and 4-positions by halogen; and $Ar^2$ is typically selected from phenyl groups substituted in the 2- and 5-positions by halogen. In particular embodiments, $Ar^1$ is 4-chlorophenyl or 4-trifluoromethylphenyl and $Ar^2$ is 2,5-difluorophenyl.

$R^{1b}$ typically represents H, methyl or OH, preferably H.

$R^{1c}$ typically represents H or methyl, preferably H.

Z is typically selected from CN, $N_3$, $OR^{2a}$, $N(R^{2a})_2$, $CO_2R^{2a}$, $COR^{2a}$, $CON(R^{2a})_2$, $OCON(R^{2a})_2$, $CONR^{2a}(OR^{2a})$, $CON(R^{2a})N(R^{2a})_2$, and optionally substituted phenyl or heteroaryl.

When Z represents $OR^{2a}$, $R^{2a}$ aptly represents H, Ar (especially heteroaryl such as pyridyl), alkyl (such as methyl, ethyl, propyl or butyl), or substituted alkyl (especially $CH_2Ar$ such as benzyl or pyridylmethyl).

When Z represents $N(R^{2a})_2$, the $R^{2a}$ groups aptly complete an N-heterocyclyl group which is optionally substituted as described above. Preferred substituents include =O and methyl. Specific examples of N-heterocyclyl groups represented by Z include morpholin-4-yl, 2-oxo-imidazolidin-1-yl, 5,5-dimethyl-2,2-dioxo-oxazolidin-3-yl, 2,5-dioxo-imidazolidin-1-yl, 2-oxo-oxazolidin-3-yl, 2-oxo-pyridin-1-yl, and 2-oxo-pyrrolidin-1-yl.

When Z represents $CO_2R^{2a}$, $R^{2a}$ aptly represents H or alkyl (such as methyl, ethyl, propyl or butyl).

When Z represents $COR^{2a}$, $R^{2a}$ aptly represents Ar, especially heteroaryl, and in particular 5-membered heteroaryl such as 1,2,4-triazol-3-yl.

When Z represents $CON(R^{2a})_2$ or $OCON(R^{2a})_2$, the $R^{2a}$ groups independently represent H or optionally substituted alkyl, cycloalkyl, cycloalkylalkyl or alkenyl, or together complete an N-heterocyclyl group. Very aptly, one $R^{2a}$ represents H and the other represents alkyl (such as methyl, ethyl, n-propyl, isopropyl, n-butyl, sec-butyl, tert-butyl or 1-ethylpropyl), alkenyl (such as allyl), cycloalkyl (such as cyclopropyl, cyclobutyl or cyclopentyl), cycloalkylalkyl (such as cyclopropylmethyl) or substituted alkyl (such as alkyl substituted with Ar, especially 2-pyridylethyl, 3-(imidazol-1-yl)propyl or 2-phenylethyl; or alkyl substituted with $CF_3$, $CO_2R^{2b}$, or $CON(R^{2b})_2$, especially 2,2,2-trifluoromethyl, methoxycarbonylmethyl or carbamoylmethyl). Alternatively, the two $R^{2a}$ groups complete an N-heterocyclyl group, such as morpholine, thiomorpholine, thiomorpholine-1,1-dioxide, 4-methylpiperazine, 4-phenylpiperazine, piperidine, 4-hydroxypiperidine or piperidine which is substituted in the 3- or 4-position with $CO_2R^{2b}$ and/or $C_{1-4}$alkyl, especially 3- or 4-carboxypiperidine, 3- or 4-ethoxycarbonylpiperidine, 3-carboxy-3-methylpiperidine and 3-ethoxycarbonyl-3-methylpiperidine.

When Z represents $CONR^{2a}(OR^{2a})$, each $R^{2a}$ aptly represents H or alkyl, such as methyl.

When Z represents $CON(R^{2a})N(R^{2a})_2$, each $R^{2a}$ aptly represents H or alkyl. Specific examples include $CONHNH_2$ and $CONHNH^tBu$.

When Z represents $CONHC(=NOH)R^{2a}$, $R^{2a}$ aptly represents alkyl such as methyl or ethyl.

Heteroaryl groups represented by Z are very aptly 5-membered, such as tetrazole, triazole, thiazole, thiadiazole, oxadiazole, pyrazole and imidazole, which are typically unsubstituted or substituted with methyl or hydroxy groups. The keto-tautomers of hydroxy-substituted heteroaryl groups are to be considered interchangeable with the enol forms. Specific examples include 1,2,3,4-tetrazol-1-yl, 1,2,3,4-tetrazol-2-yl, 1,2,3,4-tetrazol-5-yl, 3-hydroxy-1,2,4-triazol-5-yl, 1,2,4-triazol-3-yl, 5-methyl-1,2,4-triazol-3-yl, 2,5-dimethyl-1,2,4-triazol-3-yl, 1,3,4-oxadiazol-2-yl, 5-methyl-1,3,4-oxadiazol-2-yl, 5-methyl-1,3,4-thiadiazol-2-yl, 3-methyl-1,2,4-oxadiazol-5-yl, imidazol-2-yl, imidazol-1-yl, 4-methylthiazol-2-yl, pyrazol-1-yl, 1,2,3-triazol-1-yl, 1,2,4-triazol-1-yl, and 1,2,3-triazol-2-yl.

Examples of individual compounds in accordance with formula IIA are provided in the Examples section appended hereto.

A second subclass of the compounds of the invention comprises the compounds of formula III:

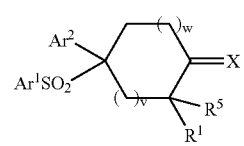

III and the pharmaceutically acceptable salts thereof, wherein
v is 1 and w is 0, 1 or 2, or v is 2 and w is 0 or 1;

X represents $C(R^1)_2$, $CHCO_2R^1$, O, $NOR^1$, $CHCON(R^1)_2$, $NNHCOR^2$, or the atoms necessary to complete a spiro-linked 5- or 6-membered carbocyclic or heterocyclic ring;

$R^5$ represents H, $CO_2R^1$ or $CON(R^1)_2$;

and $R^1$, $R^2$, $Ar^1$ and $Ar^2$ have the same meanings as before.

Preferably, v is 1 and w is 0 or 1. Most preferably, v and w are both 1.

Examples of compounds within this subclass include those wherein $Ar^1$ represents 4-chlorophenyl, $Ar^2$ represents 2,5-difluorophenyl, v and w are both 1 and X, $R^1$ and $R^5$ are as indicated in the following table:

| =X | $R^1$ | $R^5$ |
|---|---|---|
| =O | H | H |
| =O | $CH_2Ph$ | $CO_2Me$ |
| =O | H | $CONH_2$ |
| =O | H | $CO_2Me$ |
| =O | Me | $CO_2Me$ |
| =O | allyl | $CO_2Me$ |
| =N—OH | H | H |
| =N—OMe | H | H |
| =N—$OCH_2Ph$ | H | H |
| =N-$OCH_2CH=CH_2$ | H | H |
| =N—$O^tBu$ | H | H |
| =N—$OCH_2CO$—N(piperazine)N—Ph | H | H |
| =N—$OCH_2CO$—N(morpholine) | H | H |
| =N—$OCH_2CONH$—(4-Cl-C6H4) | H | H |
| =$CH_2$ | H | H |
| =$CHCO_2H$ | H | H |
| acryloyl-morpholine | H | H |
| acryloyl-piperidine-4-OH | H | H |
| acryloyl-N-Me-piperazine | H | H |
| acryloyl-N-Ph-piperazine | H | H |
| acrylamide-CH2CH2-(2-pyridyl) | H | H |
| acrylamide-(CH2)3-imidazole | N | N |

| =X | $R^1$ | $R^5$ |
|---|---|---|
| cyclic -O-CH2-O- (dioxolane) | H | N |
| =N—NH—COMe | H | H |
| =$CHCH_2CH_2CO_2Et$ | H | H |
| =N—O—$CH_2CO_2H$ | H | H | and the pharmaceutically acceptable salts thereof.

Further examples of compounds in accordance with formula III include those in which $R^1$ and $R^5$ are both H, and v, w, $Ar^1$, $Ar^2$ and X are as shown in the following table:

| v | w | $Ar^1$ | $Ar^2$ | =X |
|---|---|---|---|---|
| 2 | 0 | 4-Cl—$C_6H_4$ | 2,5-di-F—$C_6H_3$ | =O |
| 1 | 2 | 4-Cl—$C_6H_4$ | 2,5-di-F—$C_6H_3$ | =O |
| 1 | 1 | 4-$CF_3$—$C_6H_4$ | 2,5-di-F—$C_6H_3$ | =$CHCO_2Et$ |
| 1 | 0 | 4-Cl—$C_6H_4$ | 2,5-di-F—$C_6H_3$ | 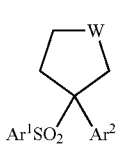 |
| 1 | 1 | 4-Cl—$C_6H_4$ | 5-Br-2-F—$C_6H_3$ | =O |
| 1 | 1 | 4-Cl—$C_6H_4$ | 2-F-5-I—$C_6H_3$ | =O |
| 1 | 1 | 4-MeO—$C_6H_4$ | 2,5-di-F—$C_6H_3$ | =O | and the pharmaceutically acceptable salts thereof.

A third subclass of the compounds of the invention is defined by formula IV and the pharmaceutically acceptable salts thereof:

IV wherein:

W represents —$NR^6$—$(CH_2)_t$—, —O—$CHR^7$—, or —$CF_2CH_2$—;

$R^6$ represents $R^1$, $COR^2$ or $CO_2R^2$;

$R^7$ represents H or $OR^1$;

t is 0 or 1; and $Ar^1$, $Ar^2$, $R^1$ and $R^2$ have the same meanings as before.

Examples of groups represented by $R^6$ include H, optionally substituted $C_{1-6}$alkyl (such as methyl, ethyl, benzyl and $CH_2CO_2Me$), $C_{2-6}$alkenyl (such as allyl), t-butoxycarbonyl, and acyl (such as $COCH_2CH_2CO_2Me$).

A fourth subclass of the compounds of the invention is defined by formula V and the pharmaceutically acceptable salts thereof:

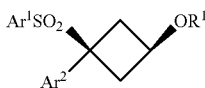

wherein $Ar^1$, $Ar^2$ and $R^1$ have the same meanings as before.

Within this subclass, $R^1$ aptly represents H, $C_{1-6}$alkyl such as methyl, ethyl or propyl, any of which is optionally substituted with $OR^{2a}$, $CO_2R^{2a}$ or $CON(R^{2a})_2$, where $R^{2a}$ has the same meaning as before, or $C_{2-6}$alkenyl such as allyl.

Individual compounds within this subclass are described in the Examples appended hereto, in particular Examples 150-159.

and the pharmaceutically acceptable salts thereof.

It will be apparent that certain compounds of formula III are tautomers of compounds of formula II. In particular, compounds of formula III wherein X represents O and $R^1$ is H may tautomerise to corresponding compounds of formula II wherein $R^3$ represents OH and bond a is double. It is to be understood that both tautomeric forms are within the scope of the invention, regardless of which tautomeric form is present in the greater amount under any particular set of conditions.

The compounds of formula I have an activity as modulators of the processing of APP by γ secretase.

The invention provides pharmaceutical compositions comprising one or more compounds of formula I or the pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to formula I or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 10 mg/kg of body weight per day. The compounds may be administered on a regimen of 1 to 4 times per day. In some cases, however, dosage outside these limits may be used.

The compounds of formula I may be synthesised by a variety of routes starting from the benzyl sulphones:

wherein $Ar^1$ and $Ar^2$ have the same meanings as before. The sulphones (1) are prepared by oxidation of thioethers $Ar^2$—$CH_2$—$SAr^1$ (2), which in turn are formed by reaction of thiols $Ar^1SH$ (3) with benzyl derivatives $Ar^2CH_2$-L (4), where L is a leaving group such as chloride or bromide and $Ar^1$ and $Ar^2$ have the same meanings as before. The reaction between (3) and (4) takes place in an inert solvent such as dichloromethane in the presence of a base such as triethylamine, while the oxidation of (2) to (1) is conveniently effected by m-chloroperoxybenzoic acid, also in an inert solvent such as dichloromethane.

In a first process, bis-alkylation of (1) with L-A-L (5) (where L and A have the same meanings as before) provides the compounds of formula I directly. The reaction may be carried out in the presence of sodium hydride in DMF at room temperature, and is particularly suitable when A represents a fragment such as —$CH_2CH_2OCH_2CH_2$—.

In a second process, sequential alkylation of (1) with L-$CH_2(CH_2)_w$CH=$CH_2$ and L-$(CH_2)_v$CH=$CH_2$ provides the bis-olefins (6) which give the cycloalkenes (7) on treatment with a rhodium catalyst:

(6)

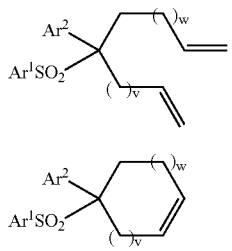

(7)

where v, w, L, Ar$^1$ and Ar$^2$ have the same meanings as before. The alkylations take place at ambient temperature in an aprotic solvent such as DMF or THF in the presence of strong base such as sodium hydride or potassium t-butoxide. Suitable catalysts for the cyclisation of (6) to (7) include bis(tricyclohexylphosphine)benzylidine ruthenium(IV) dichloride, the reaction taking place at room temperature in an inert solvent such as dichloromethane.

In a third process, reaction of (1) with at least two equivalents of an acrylate ester (8) provides enols (9) which are tautomeric with keto-esters (10):

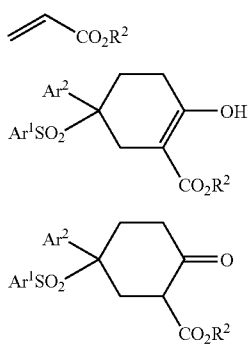

(8)

(9)

(10)

where R$^2$, Ar$^1$ and Ar$^2$ have the same meanings as before. On the basis of NMR spectral data, the products are believed to exist predominantly as the enols (9). The reaction may be carried out at ambient temperature in an inert solvent such as THF in the presence of strong base such as potassium t-butoxide.

In a fourth process, sequential treatment of (1) with BuLi, Me$_3$SiCl and formaldehyde provides vinyl sulphones (11), which react with amine derivatives (12) in the presence of trifluoroacetic acid to provide pyrrolidines (13):

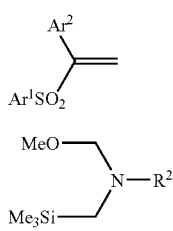

(11)

(12)

-continued

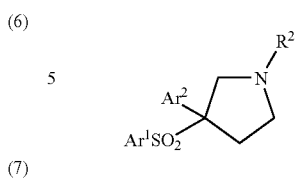

(13)

where R$^2$, Ar$^1$ and Ar$^2$ have the same meanings as before. The reaction to form (11) is carried out at −78° C. in THF, while the formation of (13) may be carried out in dichloromethane at 0° C.

An alternative route to compounds of formula I involves reaction of styrene derivatives (27) with thiophenols Ar$^1$SH in the presence of perchloric acid, with subsequent oxidation by m-chloroperoxybenzoic acid:

(27)

where A, Ar$^1$ and Ar$^2$ have the same meanings as before. The styrenes (27) are available by reaction of the triflates (28) with Ar$^2$—B(OH)$_2$ in the presence of a Pd(0) catalyst, and the triflates may be formed by treatment of the ketones (29) with N-phenyl triflamide and strong base such as lithium di-isopropylamide at low temperatures under anhydrous conditions:

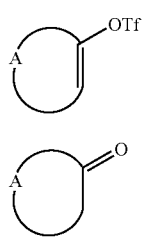

(28)

(29)

where Tf represents trifluoromethanesulphonyl and A, Ar$^1$ and Ar$^2$ have the same meanings as before.

Compounds in accordance with formula I, prepared by any of the above processes, may be converted into other compounds in accordance with formula I by the application of conventional synthesis methodology.

For example, the compounds of formulae (9) or (10) may be reacted with R$^2$-L in the presence of base to provide a mixture of O-alkyl and C-alkyl derivatives (14) and (15):

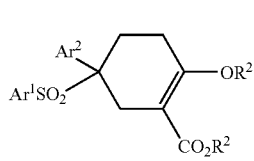

(14)

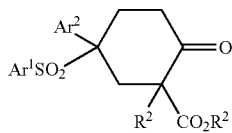
(15)

where L, $R^2$, $Ar^1$ and $Ar^2$ have the same meanings as before. The reaction is typically carried out in refluxing acetone in the presence of potassium carbonate, and the products separated by conventional chromatographic techniques.

The esters (9), (10), (14) and (15) may be hydrolysed to the corresponding carboxylic acids, which may be coupled with amines to provide the corresponding amides, or with alcohols to provide alternative esters. Alternatively, the esters (9), (10), (14) and (15) themselves may be reacted with amines or alcohols to provide amides or alternative esters.

Reduction of the esters (9) or (10) with sodium borohydride provides the diols (16):

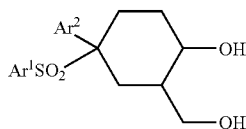
(16)

The cycloalkenes (7) may be reduced to the corresponding cycloalkanes (17):

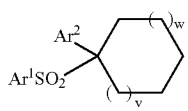
(17)

where v, w, $Ar^1$ and $Ar^2$ have the same meanings as before. The reaction is typically carried out by hydrogenation over Pd/C at 45 psi. in a solvent such as ethyl acetate.

Alternatively, the cycloalkenes (7) may be treated sequentially with borane in THF and alkaline hydrogen peroxide to provide the alkanols (18):

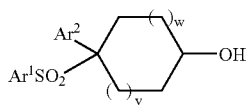
(18)

where v, w, $Ar^1$ and $Ar^2$ have the same meanings as before. The alkanols may be reacted with methanesulphonyl chloride to provide the corresponding mesylates, which may be subjected to nucleophilic displacement by a variety of nucleophiles such as halide, cyanide and azide (e.g. at 90° C. in DMF solution). Azides formed in this way may be reduced to the primary amines (19):

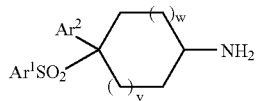
(19)

where v, w, $Ar^1$ and $Ar^2$ have the same meanings as before. The reduction may be effected by treatment with triphenylphosphine in refluxing aqueous THF.

The alkanols (18) may also be oxidised to ketones (20):

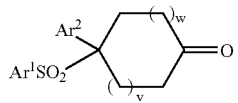
(20)

where v, w, $Ar^1$ and $Ar^2$ have the same meanings as before. Any of the conventional oxidants may be used, such as pyridinium dichromate, but an alternative route to the ketones (20) in which v and w are both 1 is by decarboxylation of the compounds (9)/(10), which may be accomplished by heating at 150° C. in DMSO in the presence of sodium chloride and water. The latter procedure, followed by reduction of the carbonyl group with borohydride, provides an alternative route to the alkanols (18) in which v=w=1.

The ketones (20) react with $R^1$—$ONH_2$ to form oximes and alkoximes (21):

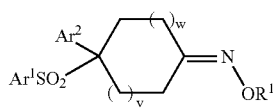
(21)

where $R^1$, v, w, $Ar^1$ and $Ar^2$ have the same meanings as before. The reaction may be carried out in a mixture of pyridine and ethanol at 80° C.

The ketones (20) may alternatively be converted to the amines (22) by reaction with $(R^1)_2NH$ and sodium triacetoxyborohydride:

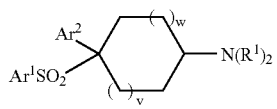
(22)

where $R^1$, v, w, $Ar^1$ and $Ar^2$ have the same meanings as before. The reaction takes place at ambient temperature in dichloromethane, and is particularly suitable for the synthesis of secondary and tertiary amines wherein at least one of the $R^1$ groups is other than H.

The ketones (20) may converted to the difluorides (23) by reaction with (diethylamino)sulphur trifluoride:

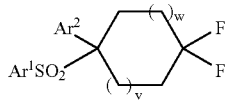

(23)

where v, w, $Ar^1$ and $Ar^2$ have the same meanings as before. The reaction may be carried out in dichloromethane at ambient temperature.

The ketones (20) may alternatively be condensed with ylides such as $Ph_3P=CH(R^1)_2$ and $Ph_3P=CHCO_2R^2$ to form alkylidene derivatives (24) and (25):

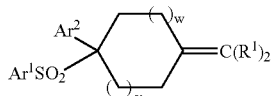

(24)

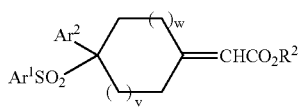

(25)

where v, w, $R^1$, $R^2$, $Ar^1$ and $Ar^2$ have the same meanings as before. The ylides are formed by treatment of the corresponding phosphonium bromides with butyllithium in an aprotic solvent at low temperature, and are reacted in situ with the ketones (20).

The primary amines (19) may be alkylated and/or acylated in accordance with standard techniques. In particular, they may be coupled with acids $R^2CO_2H$ to form the amides (26) using any of the well known processes for amide bond formation:

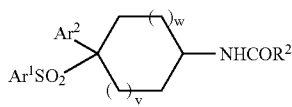

(26)

where $R^2$, v, w, $Ar^1$ and $Ar^2$ have the same meanings as before. Suitable processes include conversion of the carboxylic acid to the acid chloride prior to reaction with amine (19), and the use of coupling agents such as dimethylaminopyridine, hydroxybenzotriazole, dicyclohexylcarbodiimide, carbonyldiimidazole and the like.

Compounds of formula IIA in which m is 0 and Z is $CO_2R^{2a}$, $CON(R^{2a})_2$, $CONR^{2a}(OR^{2a})$, $CON(R^{2a})N(R^{2a})_2$ or $CONHC(=NOH)R^{2a}$ may be prepared by coupling of a carboxylic acid (30) with (respectively) $R^{2a}OH$, $HN(R^{2a})_2$, $HNR^{2a}(OR^{2a})$, $HN(R^{2a})N(R^{2a})_2$ or $H_2NC(=NOH)R^{2a}$,

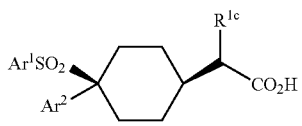

(30)

where $Ar^1$, $Ar^2$, $R^{1c}$ and $R^{2a}$ have the same meanings as before. Any of the standard coupling techniques may be used, including the use of coupling agents such as dimethylaminopyridine, hydroxybenzotriazole, dicyclohexylcarbodiimide, carbonyldiimidazole and the like. In one preferred method, the acid is converted to the corresponding acid chloride (e.g. by treatment with oxalyl chloride in DMF solution) and reacted directly with the desired nucleophile. In another preferred method, the acid is converted to an active ester derivative such as the pentafluorophenol ester (e.g. by coupling with the phenol in the presence of dicyclohexyl carbodiimide), and this intermediate is reacted with the desired nucleophile.

The acids (30) are available by hydrolysis of the esters (31), typically under alkaline conditions such as treatment with LiOH in ethanol solution:

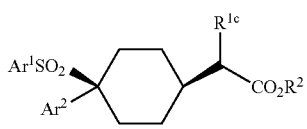

(31)

where $Ar^1$, $Ar^2$, $R^{1c}$ and $R^2$ have the same meanings as before. In this context, $R^2$ is typically methyl or ethyl.

The esters (31) are available by reduction of the alkylidene derivatives (25) in which v=w=1, optionally followed by alkylation with ($C_{1-4}$alkyl)-L where L is a leaving group (especially bromide or iodide) when $R^{1c}$ is other than H. The reduction may be carried out using sodium borohydride and nickel(II) chloride in ethanol, while the optional alkylation may be effected by treating the ester (31, $R^{1c}$=H)) with strong base (e.g. sodium bis(trimethylsilyl)amide) in an aprotic solvent at low temperature, followed by treatment with ($C_{1-4}$alkyl)-L and warming to room temperature.

Alternatively, the unsaturated esters (25, v=w=1) may be hydrolysed to the corresponding acids and converted to amides by reaction with $HN(R^{2a})_2$ prior to reduction.

Compounds of formula IIA in which m is 0 and Z is $COR^{2c}$ may be prepared by treatment of the corresponding compounds in which Z is $CONR^{2c}(OR^{2c})$ with $R^{2c}$—Li, where $R^{2c}$ represents $R^{2a}$ which is other than H. The reaction is typically carried out in an aprotic solvent at low temperature, and is particularly useful when $R^{2c}$ in $COR^{2c}$ represents aryl or heteroaryl. In such cases, subsequent reduction of the carbonyl group (e.g. using sodium borohydride) provides the compounds of formula IIA in which m is 1, $R^{1b}$ is OH and Z is aryl or heteroaryl.

Compounds of formula IIA in which m is 0 and Z is halogen, CN, $N_3$, $OR^{2a}$, $N(R^{2a})_2$ or heteroaryl bonded through N may be obtained by reaction of a sulphonate ester (32) with (respectively) halide ion, cyanide ion, azide ion, $R^{2a}OH$, $HN(R^{2a})_2$ or heteroaryl comprising NH in the ring:

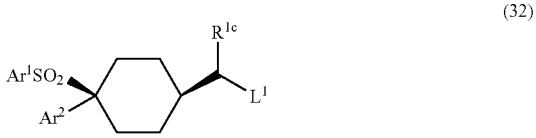

(32)

where $L^1$ represents a sulphonate leaving group (such as mesylate, tosylate or triflate) and $Ar^1$, $Ar^2$ and $R^{2a}$ have the same meanings as before. The displacement reaction may be carried out in DMF at elevated temperature, e.g. about 80° C. When the nucleophile is $R^{2a}OH$, $HN(R^{2a})_2$ or heteroaryl comprising NH in the ring, it is advantageous to generate the corresponding anion by treatment with sodium hydride prior to reaction with (32).

The sulphonates (32) are prepared by reaction of the alcohols (33) with the appropriate sulphonyl chloride (e.g. under anhydrous conditions at low temperature in the presence of a tertiary amine).

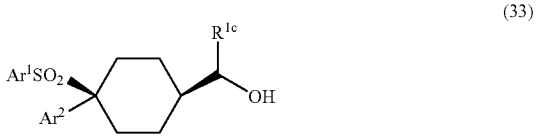

(33)

The alcohols (33) are available from the hydroboration of alkylidenes (24) in which one of the $R^1$ groups is H and the other is H or $C_{1-4}$alkyl. The process typically involves reaction with borane in THF at room temperature, followed by treatment with alkaline hydrogen peroxide and separation of the desired cis isomer by chromatography.

An alternative route to the alcohols (33) in which $R^{1c}$ is H involves converting an alcohol (18) in which v=w=1 to the corresponding mesylate (or equivalent leaving group), effecting nucleophilic displacement with cyanide ion, hydrolysing the resulting nitrile to the corresponding carboxylic acid, followed by reduction to the primary alcohol. The hydrolysis is typically carried out under acid conditions (e.g. in a mixture of acetic acid and conc. HCl at 110° C.) and the reduction is conveniently carried out by sequential treatment with isobutyl chloroformate and borohydride in THF.

Compounds of formula IIA in which m is 0 and Z is $OCOR^{2a}$ or $OCON(R^{2a})_2$ are available by reaction of alcohols (33) with (respectively) $R^{2a}COCl$ or $R^{2a}$—NCO in accordance with standard procedures.

Compounds of formula IIA in which m is 0 and Z represents aryl or heteroaryl bonded through C may be prepared by reaction of a sulphonyl derivative (32) with the appropriate aryllithium or heteroaryllithium. Alternatively, the corresponding compounds in which Z represents a functional group such as CN, $CO_2H$, $CONH_2$, $CONHNH_2$ or $CONHC(=NOH)R^{2a}$ may be converted to heteroaryl derivatives using conventional techniques of heterocyclic synthesis. Examples of such conversions include:

treatment of a nitrile derivative with azide to form a tetrazol-5-yl derivative;

treatment of a nitrile derivative with methanol and HCl, followed by a hydrazide, to form a 5-substituted-1,3,4-oxadiazol-3-yl derivative;

treatment of a hydrazide derivative with triethylorthoformate to form a 1,3,4-oxadiazol-3-yl derivative;

treatment of a hydrazide derivative with acetamidine to form a 5-methyl-1,2,4-triazol-3-yl derivative;

treatment of an amide derivative with Lawesson's reagent, followed by a chloromethyl ketone, to form a 4-substituted-thiazol-2-yl derivative;

treatment of a carboxylic acid derivative (or active ester thereof) with semicarbazide to form a 1,2,4-triazol-3-one derivative;

treatment of a carboxylic acid derivative (or active ester thereof) with a hydrazide, followed by Lawesson's reagent, to form a 5-substituted-1,3,4-thiadiazol-2-yl derivative; and treatment of a $CONHC(=NOH)R^{2a}$ derivative with strong base (e.g. potassium t-butoxide) to form a 3-substituted-1,2,4-oxadiazol-5-yl derivative.

Illustrations of these conversions are provided in the Examples appended hereto.

Compounds of formula IIA in which m is 1 and $R^{1b}$ is H or $C_{1-4}$alkyl may be obtained via oxidation of an alcohol (33) to the corresponding aldehyde or ketone, and elaboration of the carbonyl group thereof in the manner described previously in connection with conversion of the ketones (20) into compounds of formula IIA in which m is 0.

Compounds of formula V may be obtained by treatment of the sulphones (1) with an alkyllithium (e.g. BuLi) and epichlorohydrin, and optional alkylation of the resulting cyclobutanol with $R^1$-L, where $R^1$ and L have the same meanings as before. The reaction of (1) with epichlorohydrin is typically carried out at low temperature in THF, and the optional alkylation is typically effected by treatment of the cyclobutanol with sodium hydride in DME and reaction of the resulting alkoxide with $R^1$-L.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. In particular, certain products may be formed as mixtures of cis and trans isomers in which a particular ring substituent is on the same or opposite side of the ring as the arylsulphonyl group. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:
(1) Mouse neuroblastoma neuro 2a cells expressing human app695 are cultured at 50-70% confluency in the presence of sterile 10 mM sodium butyrate.
(2) Cells are placed in 96-well plates at 30,000/well/100 μL in minimal essential medium (MEM) (phenol red-free)+10% foetal bovine serum (FBS), 50 mM HEPES buffer (pH7.3), 1% glutamine, 0.2 mg/ml G418 antibiotic, 10 mM sodium butyrate.
(3) Make dilutions of the compound plate. Dilute stock solution to 5.5% DMSO/110 μM compound. Mix compounds vigorously and store at 4° C. until use.
(4) Add 10 μL compound/well. Mix plate briefly, and leave for 18 h in 37° C. incubator.
(5) Remove 90 μL of culture supernatant and dilute 1:1 with ice-cold 25 mM HEPES (pH 0.3), 0.1% BSA, 11.0 mM EDTA (+broad spectrum protease inhibitor cocktail; pre-aliquotted into a 96-well plate). Mix and keep on ice or freeze at −80° C.
(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.
(7) Prepare reagents necessary to determine amyloid peptide levels, for example by ELISA assay.
(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 μL/well MTS/PES solution to the cells; mix and leave at 37° C.
(11) Read plate when the absorbance values are approximately 1.0 (mix briefly before reading to disperse the reduced formazan product).

Alternative assays are described in *Biochemistry*, 2000, 39(30), 8698-8704.

The Examples of the present invention all had an $ED_{50}$ of less than 10 μM, preferably less than 1 μM and most preferably less than 100 nM in at least one of the above assays.

The following examples illustrate the present invention.

EXAMPLES

Intermediate 1

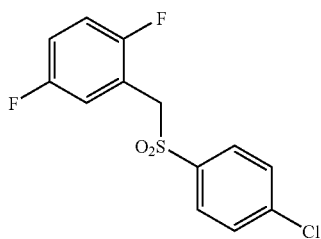

4-Chlorothiophenol (3.6 g, 0.025 mol) in dichloromethane (100 ml) was treated with 2,5-difluorobenzyl bromide (5.17 g, 0.025 mol) and triethylamine (3.9 ml, 0.028 mol), reaction was stirred for 2 hours then diluted with dichloromethane (250 ml) and washed with water (100 ml) and brine (100 ml). The separated organic layer was dried (MgSO$_4$) and evaporated to dryness. Product was purified by passing down a plug of silica eluting with hexane-ethyl acetate mixtures. 5.12 g. $^1$H NMR CDCl$_3$ 7.23 (4H,s), 6.69-6.86 (3H,m) and 4.04 (2H,s).

This thioether (5.12 g, 0.018 mol) was dissolved in dichloromethane (100 ml) and treated with m-chloroperoxybenzoic acid (14.3 g, 0.042 mol 50% w/w)) and stirred for 2 hours. The reaction was then washed with Na$_2$S$_2$O$_5$ (5% solution, 100 ml), brine (50 ml), dried (MgSO$_4$) and evaporated to dryness. The sulphone product was purified on silica eluting with hexane-ethyl acetate mixtures, 3.6 g. $^1$H NMR CDCl$_3$ 7.61 (2H,d, J=8.6 Hz), 7.45 (2H,d, J=8.6 Hz), 7.13-7.08 (1H, m), 7.05-7.01 (1H,m), 7.05-7.00 (1H,m), 6.99-6.87 (1H,m) and 4.36 (2h,s).

Intermediate 2

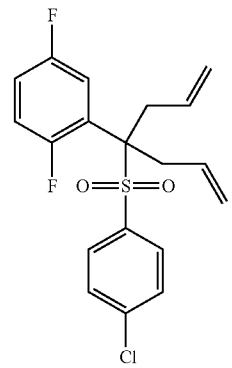

Intermediate 1 (500 mg, 1.66 mmol) in N,N-dimethylformamide (DMF) (2.5 ml) was treated with sodium hydride (73 mg, 60% w/w in mineral oil, 1.82 mmol), then allyl bromide (216 μl, 2.49 mmol). The mixture was stirred at room temperature for 16 hours, a further portion of sodium hydride (36 mg, 60% w/w in mineral oil, 0.91 mmol) added and stirring at room temperature continued for another 5.5 hours. The reaction mixture was diluted with water (40 ml) and extracted with ethyl acetate (3×50 ml), and the combined organics washed with brine (sat., 100 ml), dried (MgSO$_4$) and evaporated to dryness, giving an orange oil (506 mg). This material was chromatographed on silica, eluting with 0-5% ethyl acetate in hexanes to give product 199 mg. $^1$H NMR (400 MHz, CDCl$_3$), 2.79-2.88 (1H, m), 3.17-3.23 (1H, m), 4.57-4.61 (1H, m), 5.00-5.10 (2H, m), 5.50-5.60 (1H, m), 6.79-6.85 (1H, m), 6.94-7.00 (1H, m), 7.23-7.28 (1H, m), 7.38-7.41 (2H, m), 7.53-7.56 (2H, m).

This mono-allyl derivative (50 mg, 0.15 mmol) in tetrahydrofuran (2 ml) was treated with allyl bromide (14 μl, 0.16 mmol). Potassium tert-butoxide (161 μl, 1M solution in tetrahydrofuran, 0.16 mmol) was then dripped in slowly and mixture stirred at room temperature for 2 hours. The reaction mixture was diluted with ethyl acetate (20 ml), washed with water (30 ml) and then brine (sat., 30 ml), then dried (MgSO$_4$)

and evaporated to dryness, giving 39 mg crude material. This was purified by preparative t.l.c., eluting with 5% ethyl acetate in hexanes, giving product 10.6 mg.

¹H NMR (400 MHz, CDCl₃), 3.08-3.15 (2H, m), 3.20-3.30 (2H, m), 5.14-5.24 (4H, m), 5.75-5.90 (2H, m), 6.75-6.82 (1H, m), 6.94-7.00 (2H, m), 7.37 (4H, d, J=8.0 Hz).

Intermediate 3

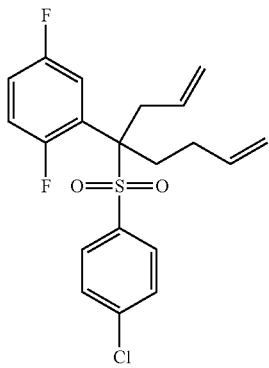

Intermediate 1 (1.01 g, 3.34 mmol) in DMF (3 ml) was dripped into a stirring suspension of sodium hydride (134 mg, 60% w/w in mineral oil, 3.34 mmol) in DMF (2 ml), and the mixture treated with 4-bromo-1-butene (508 μl, 5.01 mmol) and stirred at room temperature for 1.5 hours. The reaction mixture was diluted with water (150 ml) and extracted with ethyl acetate (3×100 ml). The combined organics were washed with brine (sat., 150 ml), dried (MgSO₄) and evaporated in vacuo to give 1.05 g crude material which was chromatographed on silica, eluting with 0-5% ethyl acetate in hexanes to give product. 720 mg. ¹H NMR (360 MHz, CDCl₃), 1.85-1.96 (1H, m), 2.06-2.25 (2H, m), 2.49-2.58 (1H, m), 4.54 (1H, dd, J=11.2 Hz and J=2.5 Hz), 4.97 (2H, dq, J=12.9 Hz and J=1.2 Hz), 5.64-5.75 (1H, m), 6.80-6.86 (1H, m), 6.96-7.02 (1H, m), 7.22-7.27 (1H, m), 7.36-7.40 (2H, m), 7.51-7.55 (2H, m).

This homoallyl derivative (720 mg, 2.02 mmol) in DMF (10 ml) was dripped into a stirring suspension of sodium hydride (202 mg, 60% w/w in mineral oil, 5.06 mmol) in DMF (7 ml). The mixture was treated with allyl bromide (875 μl, 10.1 mmol) and stirred at room temperature for 64 hours, then diluted with water (150 ml) and extracted with ethyl acetate (3×100 ml). The combined organics were washed with brine (sat., 200 ml), dried (MgSO₄) and evaporated in vacuo to give 910 mg crude material which was chromatographed on silica, eluting with 0-5% ethyl acetate in hexanes to give product (794 mg.) A portion of this material (44 mg) was further purified by preparative t.l.c., eluting with 10% ethyl acetate in hexanes to give 36 mg pure product. ¹H NMR (400 MHz, CDCl₃), 1.8-1.95 (1H, m), 2.27-2.33 (1H, m), 2.41-2.46 (2H, m), 3.03 (1H, dd, J=14.8 Hz and J=7.0 Hz), 3.31 (1H, dd, J=15.4 Hz and J=6.3 Hz), 4.99-5.06 (2H, m), 5.18-5.28 (2H, m), 5.73-5.84 (1H, m), 5.90-6.00 (1H, m), 6.78-6.86 (1H, m), 7.00-7.08 (2H, m), 7.31-7.37 (4H, m).

Intermediate 4

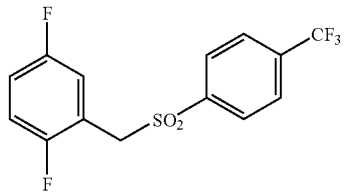

Prepared as for Intermediate 1, using 4-trifluoromethylthiophenol, and obtained as a solid. ¹H NMR (360 MHz, CDCl₃) δ 7.85-7.83 (2H, m), 7.76-7.74 (2H, m), 7.15-7.10 (1H, m), 7.06-7.0 (1H, m), 6.92-6.86 (1H, m) and 4.46 (2H, s).

Intermediate 5

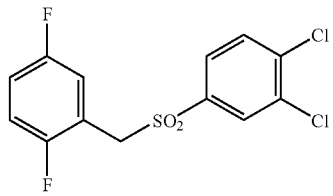

Prepared as for Intermediate 1, using 3,4-dichlorothiophenol, and obtained as a solid. ¹H NMR (360 MHz, CDCl₃) δ 7.76 (1H, d, J=2 Hz), 7.76 (1H, d, J=8.4 Hz), 7.51-7.48 (1H, m), 7.17-7.11 (1H, m), 7.08-7.05 (1H, m), 6.96-6.90 (1H, m) and 4.37 (2h, s).

Intermediate 6

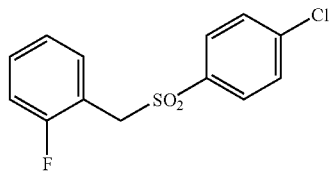

Prepared as for Intermediate 1 using 4-chlorothiophenol and 2-fluorobenzyl bromide as starting materials to obtain product as a solid. ¹H NMR (360 MHz, CDCl₃) δ 7.59-7.56 (2H, m), 7.44-7.41 (2H, m), 7.36-7.29 (2H,m), 7.16-7.12 (1H, m), 6.95-6.90 (1H,m) and 4.40 (2H, s).

Intermediate 7

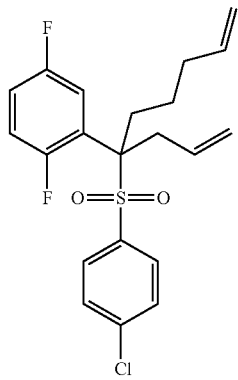

Prepared as for Intermediate 3, substituting 5-bromo-1-pentene for 4-bromo-1-butene.

$^1$H NMR (400 MHz, CDCl$_3$), 1.20-1.31 (1H, m), 1.54-1.68 (1H, m), 2.06-2.12 (2H, m), 2.33-2.38 (2H, m), 2.99-3.05 (1H, m), 3.28 (1H, dd, J=15.6 Hz and J=6.4 Hz), 4.97-5.05 (2H, m), 5.16-5.26 (2H, m), 5.70-5.78 (1H, m), 5.87-5.98 (1H, m), 6.78-6.84 (1H, m), 6.99-7.06 (2H, m), 7.29-7.37 (4H, m).

Example 1

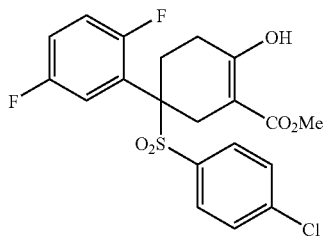

Intermediate 1 (1 g, 3.31 mmol) and methyl acrylate (0.84 ml, 9.27 mmol) in tetrahydrofuran (30 ml) were treated dropwise with potassium $^t$butoxide (3.64 ml 1M solution in tetrahydrofuran, 3.64 mmol). The reaction was stirred for 2 hours, diluted with ethyl acetate (100 ml) and washed with water (50 ml) and brine (50 ml). The organic phase was separated, dried (MgSO$_4$) and evaporated to dryness, and the product purified on silica eluting with hexane-ethyl acetate mixtures. (1.0 g). $^1$H NMR CDCl$_3$ 12.0 (1H,s), 7.41 (4H,s), 7.06-7.0 (2H,m), 6.87-6.81 (1H,s), 3.81 (3H,s), 3.38 (1H,dd, J=3.2, 15.8 Hz), 3.02-2.92 (2H,m), 2.52 (1H,dd, J=5.7, 18.5 Hz), 2.3-2.2 (1H,m) and 2.2-2.1 (1H,m).

Example 2

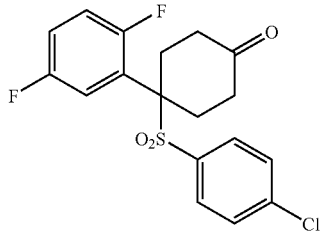

The ester from Ex. 1 (1.0 g, 2.25 mmol) in dimethylsulfoxide (10 ml) was treated with NaCl (0.3 g, 4.96 mmol) and water (0.9 ml, 4.96 mmol) and heated at 150° C. for 2 hours. The cooled reaction mixture was diluted with ethyl acetate (100 ml), washed with saturated NH$_4$Cl (100 ml), and the organic phase separated, dried (MgSO$_4$) and evaporated to dryness. The product was purified on silica eluting with hexane-ethyl acetate mixtures, 0.5 g. $^1$H NMR CDCl$_3$ 7.43-7.37 (4H,m), 7.22-7.1 (2H,m), 6.97-6.9 (1H,m), 3.05-2.98 (2H,m) and 2.61-2.53 (2H,m).

Example 3

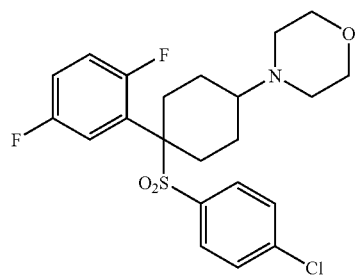

The ketone from Ex. 2 (0.14 g, 0.36 mmol) and morpholine (0.048 ml, 0.54 mmol) in dichloroethane (10 ml) were treated with sodium triacetoxyborohydride (0.23 g, 1.08 mmol) and stirred at room temperature for 18 hours. The reaction was diluted with ethyl acetate (50 ml), washed with saturated sodium bicarbonate (2×50 ml) and brine (50 ml), and the organic phase separated, dried (MgSO$_4$) and evaporated to dryness. The cis and trans products were purified on silica eluting with hexane-ethyl acetate mixtures, 0.04 and 0.06 g.

Isomer A $^1$H NMR CDCl$_3$ 7.36-7.32 (4H,m), 7.14-7.09 (2H,m), 7.06-7.01 (1H, m), 3.75-3.73 (4H,m),2.67-2.60 (2H, m), 2.50-2.45 (4H,m), 2.36-2.32 (2H,m), 2.09-2.04 (3H,m) and 1.31-1.21 (2H,m). MS (MH+) 456.

Isomer B $^1$H NMR CDCl$_3$ 7.38-7.32 4H, m), 7.1-7.0 (2H, m), 6.87-6.80 (1H,m), 3.64-3.62 (4H,m), 3.0-2.6 (2H,br m), 2.45-2.26 (4H,m), 2.32-2.04 (5H,m) and 1.19-1.12 (2H,m). MS (MH+) 456.

Example 4

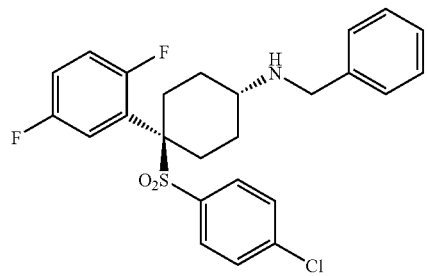

and

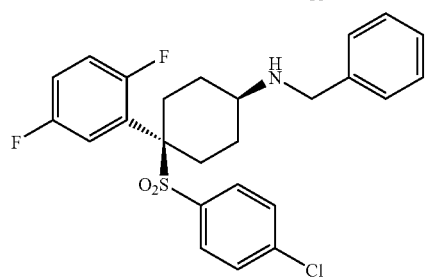

prepared as in example 3, substituting benzylamine for morpholine. MS (MH+) 477(479)

Examples 5-16

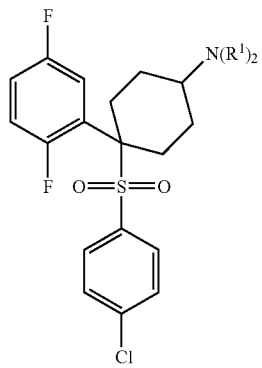

To the ketone from Ex. 2 (50 mg, 0.13 mmol) in dichloroethane (2 ml) was added the appropriate amine (0.95 eq) and then sodium triacetoxyborohydride (42 mg, 0.2 mmol). The reaction was stirred at room temperature until the starting amine was consumed (typically 24-48 h), then sat. aq sodium hydrogen carbonate (1 ml) was added, followed by dilution with dichloromethane (2 ml). The organic layer was removed and transferred to a SCX Varian Bond Elut™ cartridge and the organic layer passed through the cartridge by suction filtration. The product was liberated from the cartridge by passing a solution of ammonia in methanol (2.0 M) through it. Evaporation to dryness afforded the product, usually as a white solid.

By this method, the following were obtained as mixtures of cis and trans isomers:

| Example No. | —N(R¹)₂ | MS (MH+) |
|---|---|---|
| 5 | morpholine-thio (N-thiomorpholinyl) | 438 |
| 6 | N-methylpiperazinyl | 467 |
| 7 | N-phenylpiperazinyl | 529 |
| 8 | 4-CO₂Me-piperidinyl | 510 |
| 9 | 1,4-dioxa-8-azaspiro[4.5]decyl | 510 |
| 10 | 3-hydroxypiperidinyl | 468 |
| 11 | 4-hydroxypiperidinyl | 468 |
| 12 | 4-methyl-3-oxopiperazinyl | 467 |
| 13 | —NHCH₂CO₂Me | 492 |
| 14 | 4-methyl-1-phenyl-3-oxopiperazinyl | 543 |
| 15 | 4-CF₃-piperidinyl | 556 |
| 16 | 3-CO₂Et-3-Me-piperidinyl | 538 |

Examples 17-21

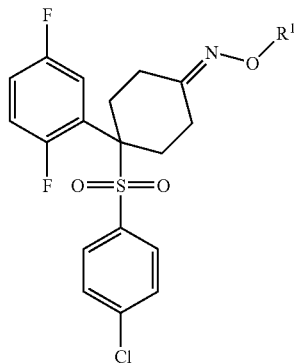

The ketone from Ex. 2 (0.13 g, 0.33 mmol) and hydroxylamine or alkoxylamine H₂NOR¹ (0.92 mmol) were dissolved in pyridine-ethanol (9 ml, 2:1) and heated at 80° C. for 3 hours. The reaction was then diluted with ethyl acetate (50 ml), washed with 2N HCl (5×25 ml), dried (MgSO₄) and evaporated to dryness. Product were purified on silica eluting with hexane-ethyl acetate mixtures.

By this route there were obtained:

| Example No. | R¹ |
|---|---|
| 17 | H |
| 18 | methyl |
| 19 | CH₂CH═CH₂ |
| 20 | t-butyl |
| 21 | benzyl | with yields and spectral data as follows:

Example 17

Yield 69 mg, $^1$H NMR CDCl$_3$ 7.60 (1H,br), 7.41-7.36 (4H, m), 7.17-7.07 (2H, m), 6.93-6.87 (1H, m), 3.47-3.43 (1H,m), 2.88-2.83 (2H, m), 2.31-2.23 (2H,m), 2.07-2.04 (1H,m) and 1.71-1.68 (1H,m). MS MH+ 399.

Example 18

Yield 22 mg. $^1$H NMR CDCl$_3$ 7.41-7.39 (4H, m), 7.16-7.06 (2H, m), 6.93-6.86 (1H, m), 3.76 (3H, s), 3.4-3.33 (1H, m), 2.85-2.65 (2H, m), 2.55-2.52 (1H, m), 2.30-2.21 (2H, m), 2.04-2.02 (1H, m) and 1.68-1.61 (1H, m).

Example 19

Yield 28 mg. $^1$H NMR CDCl$_3$ 7.41-7.36 (4H,m), 7.15-7.05 (2H, m), 6.93-6.86 (1H, m), 5.98-5.88 (1H, m), 5.27-5.16 (2H, m), 4.49-4.48 (2H, m), 3.43-3.39 (1H, m), 2.91-2.81 (2H, m), 2.57-2.34 (1H, m), 2.34-2.19 (2H, m), 2.07-1.98 (1H, m) and 1.75-1.61 (1H, m).

Example 20

Yield 32 mg. $^1$H NMR CDCl$_3$ 7.42-7.35 (1H, m), 7.18-7.05 (2H, m), 6.81-6.85 (1H, m), 3.42-3.36 (1H, m), 2.82-2.76 (2H, m), 2.58-2.54 (1H, m), 2.34-2.18 (2H, m), 2.2-1.87 (1H, m), 1.7-1.62 (1H, m) and 1.21 (9JH, s).

Example 21

Yield 38 mg. $^1$H NMR CDCl$_3$ 7.40-7.25 (9H, m), 7.15-7.05 (2H, m), 6.92-6.85 (1H, m), 5.02 (2H, s), 3.45-3.41 (1H, m), 2.90-2.80 (2H, m), 2.57-2.53 (1H, m), 2.32-2.16 (2H, m), 2.06-1.98 (1H, m) and 1.74-1.67 (1H, m).

Example 22

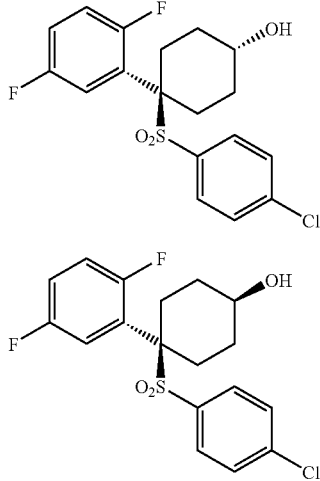

(a)

(b)

The ketone from example 2, (0.1 g, 0.26 mmol) in methanol (2 ml) was treated with NaBH$_4$ (0.098 g, 0.26 mmol) and stirred for 1 hour. The reaction was quenched with HCl (1N, 10 ml), diluted with ethyl acetate (20 ml), then the organic phase was separated, dried (MgSO$_4$) and evaporated to dryness. The cis and trans products were purified on silica eluting with hexane-ethyl acetate mixtures.

(a) (trans) 0.052 g. $^1$H NMR CDCl$_3$ 7.39-7.33 (4H,m), 7.11-7.02 (2H,m), 6.88-6.82 (1H,m), 3.80-3.73 (1H,m), 2.80-2.60 (2H,m), 2.22-2.16 (2H,m), 2.08-2.04 (2H,m), 1.53(1H, br) and 1.27-1.13 (2H,m).

(b) (cis) $^1$H NMR(CDCl$_3$) 7.40 (4H,s), 7.16-7.03 (2H,m), 6.90-6.83 (1H,m), 3.97-3.95 (1H, m), 3.77-3.68 (1H, m), 3.51-3.49 (1H, m), 2.61-2.53 (2H,m), 1.91-1.83 (2H, m) and 1.50-1.42 (2H, m).

Example 23

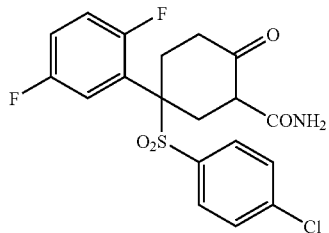

The ester from Ex. 1, (0.1 g, 0.22 mmol) in methanol was saturated with ammonia at 0° C., sealed and stirred for 18 hours. The reaction was then evaporated to dryness and the product purified on silica eluting with hexane-ethyl acetate mixtures, 0.056 g. $^1$H NMR d$_6$-DMSO 7.64 (2H,d,J=8.5 Hz), 7.53 (2H,d,J=8.6 Hz), 7.48-7.42 (2H,m), 7.34-7.29(1H,m), 7.19-7.10 (2H,m), 3.35-3.21(2H,m), 2.85-2.76 (2H,m), 2.43-2.37 (1H,m), 2.19-2.14(1H,m) and 2.0-1.95 (1H,m).

Examples 24 and 25

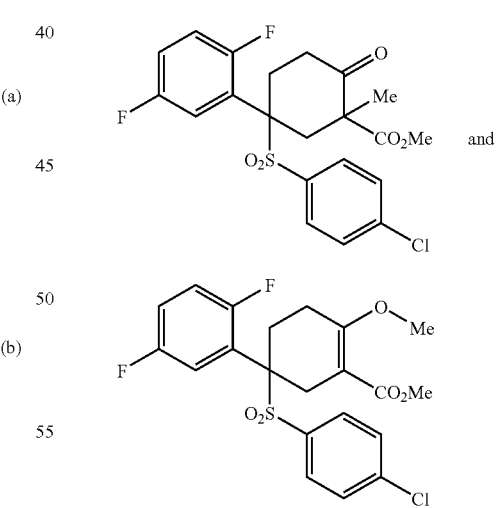

24 and

25

The product from Ex. 1 (400 mg, 0.88 mmol) and potassium carbonate (234 mg, 1.66 mmol) in acetone (10 ml) were treated dropwise with methyl iodide (0.28 ml, 4.4 mmol). After stirring for 72 hours at reflux and then evaporation to dryness, the residue was partitioned between ethyl acetate (3×100 ml) and water (50 ml) and brine (50 ml). The organic phase was separated, dried (MgSO$_4$) and evaporated to dryness. Product was purified on silica eluting with hexane-ethyl acetate mixtures, 0.42 g. A portion of this material was purified by preparative tlc, and the C-methyl product 24 [$^1$H NMR CDCl$_3$ 7.41 (2H,d, J=8.6 Hz), 7.27 (2H,d, J=10.1 Hz), 7.12-7.06 (2H,m), 6.89-6.84 (1H,m), 3.52-3.35 (1H, m), 3.22 (3H, s), 2.81-2.57 (5H,m) and 1.43 (3H,s).] and the O-methyl product 25 [$^1$H NMR CDCl$_3$ 7.39 (2H,d, J=8.6 Hz), 7.36 (2H,d, J=8.6 Hz), 7.12-7.08 (2H,m), 6.92-6.85 (1H,m), 3.80 (3H,s), 3.59 (1H, dd, J=14.8 and 1.4 Hz), 2.99-2.76 (4H,m), 2.52-2.46 (1H,m) and 1.54 (3H,s).] were obtained.

Examples 26 and 27

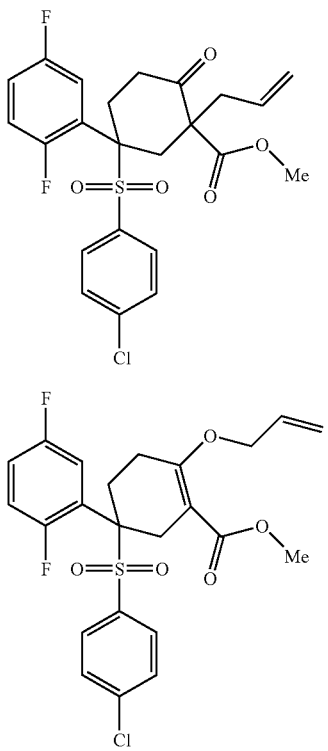

Examples 28 and 29

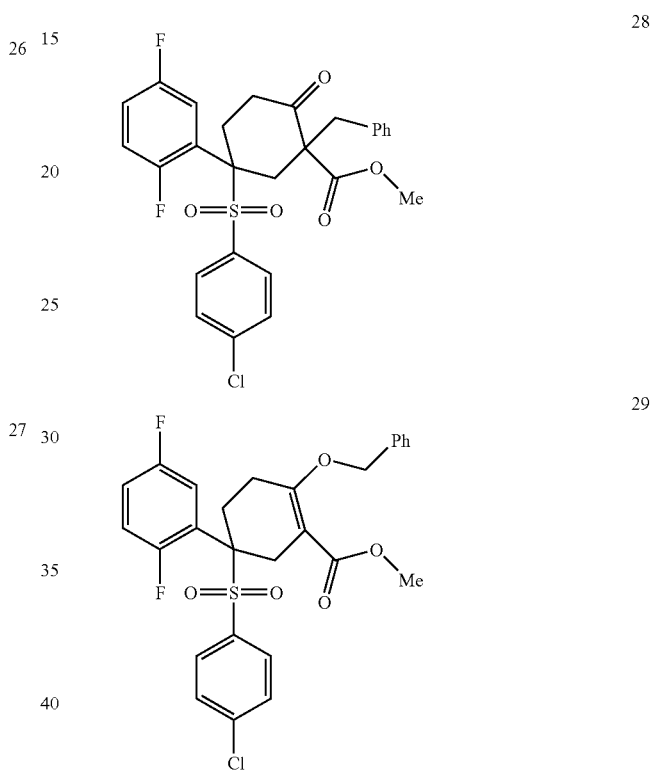

The product from Ex. 1 (200 mg, 0.45 mmol) in acetone (4 ml) was treated with potassium carbonate (125 mg, 0.90 mmol) and allyl bromide (58.7 µl, 0.68 mmol). After stirring at reflux for 2.5 hours, a further portion of allyl bromide (39 µl, 0.45 mmol) was added and stirring at reflux continued for a further 5 hours. The cooled reaction mixture was evaporated in vacuo and the resulting colourless oil diluted with water (20 ml), then extracted with ethyl acetate (3×20 ml). The combined organics were dried (MgSO$_4$) then evaporated in vacuo, giving a white foam (230 mg) which was chromatographed on silica, eluting with 0-15% ethyl acetate in hexanes to give the C-allyl product 26 (106 mg) and the O-allyl product 27 (31 mg).

A portion of 26 (30 mg, 0.06 mmol) was purified further by preparative t.l.c., eluting with 25% ethyl acetate in hexanes to give 13.7 mg. $^1$H NMR (360 MHz, CD$_3$OD), 2.50-2.61 (4H, m), 2.68-2.75 (2H, m), 2.85-2.95 (1H, br), 3.20 (3H, s), 3.36-3.40 (1H, m), 5.11-5.17 (2H, m), 5.72-5.83 (1H, m), 6.95-7.05 (1H, br), 7.20-7.25 (2H, m), 7.38-7.41 (2H, m), 7.50-7.53 (2H, m).

O-allyl 27 $^1$H NMR (360 MHz, CD$_3$OD), 2.10-2.25 (1H, m), 2.28-2.40 (1H, m), 2.71 (1H, dd, J=18.3 Hz and J=5.9 Hz), 2.98-3.02 (2H, m), 3.46 (1H, dd, J=16.4 Hz and J=3.6 Hz), 3.71 (3H, s), 4.32-4.35 (2H, m), 4.91-5.08 (2H, m), 5.67-5.75 (1H, m), 6.94-7.02 (1H, m), 7.03-7.09 (1H, m), 7.14-7.18 (1H, m), 7.46 (2H, dd, J=6.8 Hz and J=2.0 Hz), 7.54 (2H, dd, J=6.7 Hz and J=1.9 Hz).

The product from Ex. 1 (100 mg, 0.23 mmol) in acetone (2 ml) was treated with potassium carbonate (62 mg, 0.45 mmol) and benzyl bromide (41 µl, 0.35 mmol) and stirred at reflux for 16 hours. The cooled reaction mixture was evaporated in vacuo and the resulting colourless oil diluted with water (20 ml), then extracted with ethyl acetate (3×20 ml). The combined organics were dried (MgSO$_4$) then evaporated in vacuo, giving a white foam (144 mg). This material was purified by preparative t.l.c., eluting with 25% ethyl acetate in hexanes to give the C-benzyl product 28 (85 mg) $^1$H NMR (360 MHz, CD$_3$OD), 2.30-2.40 (1H, m), 2.44-2.55 (1H, m), 2.58-2.62 (2H, m), 2.74-2.90 (2H, m), 3.10-3.14 (1H, m), 3.15 (3H, s), 3.38-3.45 (1H, m), 7.00-7.11 (1H, m), 7.18-7.30 (7H, m), 7.36 (2H, dd, J=7.0 Hz and J=1.9 Hz), 7.49 (2H, d, J=8.7 Hz)

and the O-benzyl product 29. 14 mg. $^1$H NMR (360 MHz, CD$_3$OD), 2.02-2.18 (1H,m), 2.22-2.35 (1H,m), 2.73 (1H, dd, J=18.2 Hz and J=5.7 Hz), 2.90-3.02 (2H, m), 3.44 (1H, dd, J=13.2 Hz and J=2.9 Hz), 3.73 (3H, s), 4.91 (2H, d, J=4.0 Hz), 6.83-6.96 (2H, m), 7.06-7.17 (6H, m), 7.43 (2H, d, J=8.6 Hz), 7.52 (2H, d, J=8.6 Hz).

Example 30

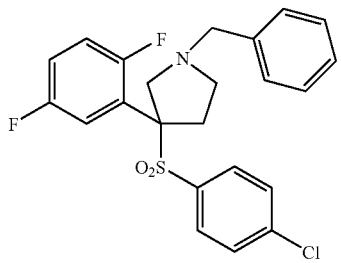

Intermediate 1 (3 g, 9.9 mmol), in tetrahydrofuran (100 ml) was treated with butyl lithium (6.8 ml, 10.9 mmol, 1.6M solution in hexanes) at −78° C. for 0.5 hours before adding chlorotrimethylsilane (1.4 mL, 10.9 mmol), and allowing the mixture to warm to r.t. for 1 hour. The reaction was then recooled to −78° C. and treated with further butyl lithium (7.5 ml, 12 mmol, 1.6M solution in hexanes), then stirred at 0° C. for 2 hrs before bubbling through gaseous formaldehyde for 15 mins. The mixture was allowed to warm to r.t. over 16 hours and was then diluted with water and the products extracted into ethyl acetate (100 ml). The organic phase was separated washed with brine (50 ml), dried (MgSO$_4$) and evaporated to dryness. Product was purified on silica eluting with hexane-ethyl acetate mixtures, 0.49 g. $^1$H NMR CDCl$_3$ 7.63-7.59 (2H,m), 7.49-7.39 (2H,m), 7.08-6.86 (2H,m), 6.88 (1H,s) and 6.09 (1H, s).

The resulting vinyl derivative (0.05 g, 0.16 mmol), and methoxymethyltrimethylsilylmethylbenzylamine (0.2 ml, 0.64 mmol) in dichloromethane (2 ml) at 0° C. were treated with trifluoroacetic acid (0.12 mL, 0.016 mmol, 1.3M in dichloromethane) and stirred at r.t. for 16 hours. The reaction was diluted with sodium hydrogen carbonate (sat aq, 3 mL), the products extracted into ethyl acetate (100 ml), and the organic phase separated, washed with brine (50 ml), dried (MgSO$_4$) and evaporated to dryness. Product was purified on silica eluting with hexane-ethyl acetate mixtures, 0.006 g. $^1$H NMR CDCl$_3$ 7.49 (2H,d, J=8.6 Hz), 7.38-7.18 (5H,m), 7.05-6.96 (2H,m), 6.90-6.83 (1H,m), 3.79 (1H, dd, J=11.5 and 1.0 Hz), 3.63 (2H, s), 3.14-2.89 (3H,m) and 2.58-2.50 (2H, m).

Example 31

Intermediate 2 (110 mg, 0.29 mmol) in dichloromethane (37 ml) was treated with bis(tricylcohexylphosphine)benzylidine ruthenium (IV) dichloride (12 mg, 0.014 mmol) and the mixture stirred at room temperature for 16 hours, then evaporated to dryness in vacuo to give 146 mg crude material. This was chromatographed on silica, eluting with 0-7.5% ethyl acetate in hexanes, giving product 84 mg. $^1$H NMR (400 MHz, CDCl$_3$), 3.10 (2H, d, J=17.3 Hz), 3.61-3.66 (2H, m), 5.65 (2H, s), 6.88-6.93 (1H, m), 7.01-7.06 (2H, m), 7.38-7.41 (2H, m), 7.49-7.52 (2H, m).

Example 32

The product of Ex. 31 (74 mg, 0.21 mmol) in ethyl acetate (7 ml) was treated with 10% palladium on carbon (20 mg) and the mixture stirred under an atmosphere of hydrogen at 1 atm at room temperature for 19 hours. The catalyst was filtered off through Hyflo™ and the solvent removed in vacuo to give 79 mg crude product. This was purified by preparative t.l.c., eluting with 10% ethyl acetate in hexanes to provide the pure product $^1$H NMR (360 MHz, CDCl$_3$), 1.73-1.82 (2H, m), 2.08-2.17 (2H, m), 2.24-2.32 (2H, m), 2.90-2.94 (2H, m), 6.75-6.81 (1H, m), 6.95-7.04 (2H, m), 7.35 (4H, s).

Example 33

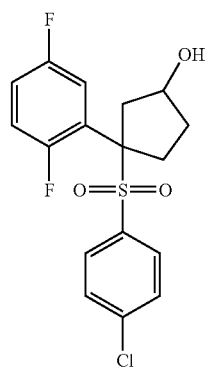

The cyclopentene from Ex. 31 (104 mg, 0.29 mmol) in tetrahydrofuran (2 ml) at 0° C. was treated with borane-tetrahydrofuran complex (1.0 ml, 1.0M solution in tetrahydrofuran, 1.0 mmol) and the mixture was stirred for 1 hour, warming to room temperature. A solution of hydrogen peroxide (27% w/w, 3 ml) in sodium hydroxide (4M, 3 ml) was added and stirring at room temperature continued for 1 hour. The reaction mixture was extracted with ethyl acetate (2×25 ml) and the combined organics were washed with brine (sat., 30 ml), dried (MgSO$_4$) and evaporated in vacuo to give 116 mg crude product. This was chromatographed on silica, eluting with 30% ethyl acetate in hexanes to give product. 78 mg.
¹H NMR (400 MHz, CDCl₃), 1.75-1.84 (1H, m), 2.37-2.49 (2H, m), 2.51-2.62 (1H, m), 2.88-2.96 (1H, m), 3.22-3.30 (1H, m), 4.72-4.80 (1H, m), 6.74-6.82 (1H, m), 6.98-7.02 (2H, m), 7.30-7.37 (4H, m).

Example 34

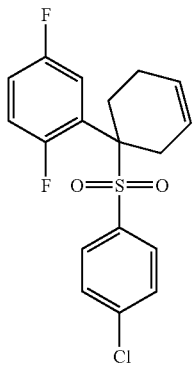

Intermediate 3 (750 mg, 1.89 mmol) in dichloromethane (200 ml) was treated with bis(tricylcohexylphosphine)benzylidine ruthenium(IV) dichloride (78 mg, 0.095 mmol) and the mixture stirred at room temperature for 16 hours. Evaporation to dryness in vacuo gave 750 mg material which was chromatographed on silica, eluting with 5-7.5% ethyl acetate in hexanes, giving product 539 mg. ¹H NMR (360 MHz, CDCl₃), 1.82-1.92 (1H, br), 2.20-2.35 (2H, m), 2.80-2.92 (1H, m), 2.94-2.98 (2H, br), 5.50-5.56 (1H, m), 5.64-5.670 (1H, m), 6.75-6.88 (1H, m), 6.95-7.10 (2H, m), 7.39 (4H, s).

Example 35

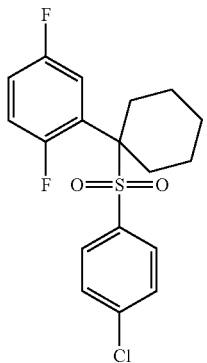

The cyclohexene from Example 34 (52.1 mg, 0.14 mmol) in ethyl acetate (5 ml) was treated with 10% palladium on carbon (15 mg) and the mixture shaken under an atmosphere of hydrogen at 45 psi for 1 hour. Catalyst was removed by filtration through Hyflo™ and the filtrate evaporated to dryness in vacuo to give 47 mg crude material. This was purified by preparative t.l.c., eluting with 10% ethyl acetate in hexanes to give product. 43 mg. ¹H NMR (400 MHz, CDCl₃), 1.10-1.25 (2H, m), 1.26-1.40 (1H, m), 1.58-1.64 (1H, m), 1.76- 1.82 (2H, m), 2.04-2.12 (2H, m), 2.65-2.80 (2H, br), 6.81-6.88 (1H, m), 7.01-7.11 (2H, m), 7.36 (4H, s).

Example 36

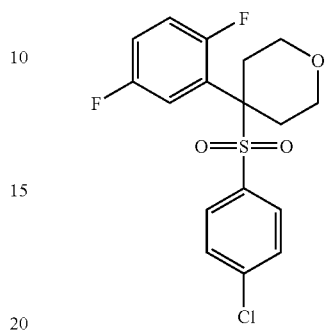

To a solution of Intermediate 1 (0.41 g, 1.36 mmol) in DMF (4 ml) was added sodium hydride (60% suspension in oil, 0.12 g, 3.0 mmol). After the effervescence had subsided 2-bromoethyl ether (0.2 ml, 1.59 mmol) was added and the solution was stirred at room temperature for 1 h. Water (20 ml) and ethyl acetate (20 ml) were added and the organic phase washed further with water (four times) and saturated brine. After drying (MgSO₄) and evaporating to dryness, the residue, dissolved in dichloromethane, was applied to a column containing silica gel. The product was eluted with 10% ethyl acetate in isohexane to give an oil which crystallised on treatment with diethyl ether to give the desired product (0.15 g). ¹H NMR (360 MHz, CDCl₃) Λ 2.50(2H, m), 2.59(2H, broad m), 3.32(2H, t J 12 Hz), 4.02(2H, dt J 12 Hz and 3 Hz), 6.89(1H, m), 7.10(2H,m), 7.38(4H, m).

Example 37

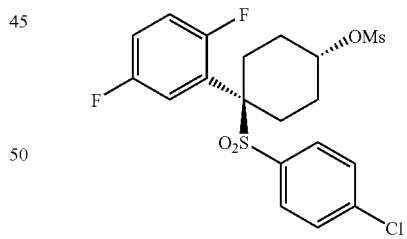

The trans cyclohexanol from Ex. 22(a) (2.7 g, 6.9 mmol) and triethylamine (1.45 mL, 10.3 mmol) in dichloromethane (50 mL) were treated with methane sulphonyl chloride (0.645 mL, 8.9 mmol) at −30° C. After 30 mins the mixture washed with water (20 mL), 10% aqueous citric acid (20 mL) and saturated aqueous sodium hydrogen carbonate (50 mL), dried (MgSO₄) and evaporated to dryness. The solid was triturated with ether to give the mesylate (2.6 g) ¹H NMR (CDCl₃) 7.40-7.37 (4H,m), 7.12-7.07 (2H,m), 6.92-6.83 (1H,m), 4.78-4.65 (1H, m), 2.96 (3H, s), 2.88-2.52 (2H, m), 2.29-2.21 (4H, m) and 1.59-1.47 (2H, m).

Example 38

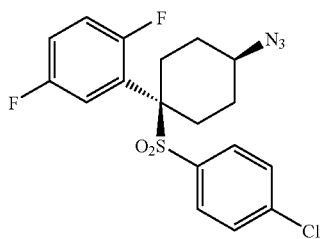

The mesylate from Ex. 37 (1.5 g, 3.2 mmol) in DMF (5 mL) was treated with sodium azide (315 mg, 4.8 mmol) and heated to 90° C. for 6 hrs. The mixture was treated with water (80 mL), and extracted with diethyl ether (3×50 mL), dried (MgSO$_4$) and evaporated to dryness. The solid was triturated with ether to give the azide (1.4 g) $^1$H NMR (CDCl$_3$) 7.40-7.34 (4H,m), 7.12-7.03 (2H,m), 6.90-6.83 (1H,m), 3.78-3.76 (1H, m), 2.62-2.41 (4H, m), 1.97-1.91 (2H, m) and 1.51-1.41 (2H, m).

Example 39

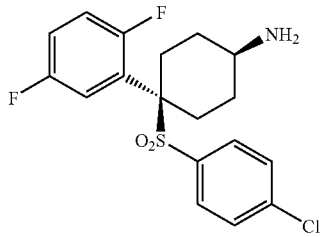

The azide from Ex. 38 (1 g, 2.55 mmol), dissolved in tetrahydrofuran (10 mL) and water (1 mL), was treated with triphenylphosphine (740 mg, 2.8 mmol) at room temperature for 15 mins and then water (5 mL) was added and the mixture was heated at reflux for 4 hrs. The mixture was allowed to cool to r.t. and then passed through SCX Varian Bond Elut™ cartridge. The basic fraction was evaporated and a portion was purified by preparative t.l.c. to give the primary amine. $^1$H NMR (CDCl$_3$) 7.35 (4H,s), 7.12-7.01 (2H,m), 6.88-6.81 (1H,m), 3.13-3.11 (1H, m), 2.64-2.44 (4H, m), 1.78-1.68 (2H, m) and 1.52-1.39 (2H, m). MS MH+ 386(388)

Example 40

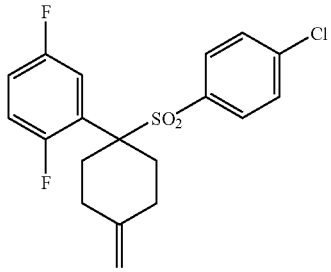

n-Butyllithium (1.6 M solution in hexanes, 15.6 mL) was added slowly to a stirred, cooled (0° C.) suspension of methyl triphenylphosphonium bromide (9.26 g, 26.0 mmol) in tetrahydrofuran (100 mL) and the mixture was stirred at room temperature for 3 h. The mixture was cooled to 0° C. and ketone from Ex. 2 (4 g, 10.4 mmol) in tetrahydrofuran (30 mL) was added. The mixture was stirred at room temperature for 1 h. then under reflux for 3 h. The mixture was cooled, poured into water and extracted with ethyl acetate. The combined organic fractions were dried (MgSO$_4$) and the solvent was evaporated under reduced pressure. The residue was purified by flash column chromatography on silica gel, eluting with isohexane:EtOAc (20:80), to give the desired product as a white solid (2.63 g, 66%). $^1$H NMR (400 MHz, CDCl$_3$) δ 7.38 (4H, s), 7.16-7.11 (1H, m), 7.09-7.03 (1H, m), 6.91-6.84 (1H, m), 4.68-4.67 (2H, m), 2.81 (2H, br m), 2.41-2.37 (2H, m), 2.20-2.13 (2H, m), and 2.00-1.93 (2H, m).

Example 41

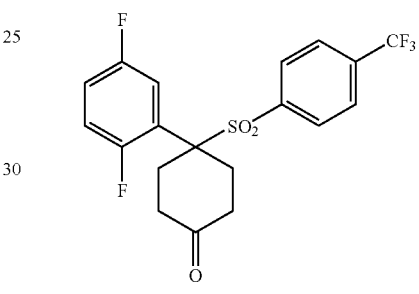

Prepared by the procedures of examples 1 and 2 using Intermediate 4 to give the product as a solid. (0.3 g) $^1$H NMR (360 MHz, CDCl$_3$) δ 7.71-7.69 (2H, d, J=7.5 Hz), 6.62-6.60 (2H, d, J=7.4 Hz), 7.22-7.11 (2H, m), 6.95-6.88 (1H, m), 3.02-2.99 (2H, m), 2.63-2.54 (4H, m) and 2.25-2.16 (2H, m).

Example 42

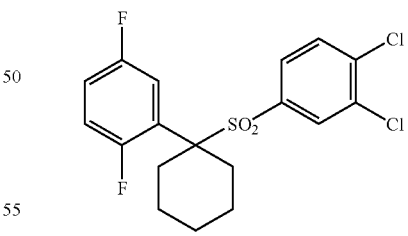

Intermediate 5 (0.54 g, 1.71 mM) was dissolved in tetrahydrofuran (20 ml) and treated with 1,5-dibromopentane (231 μl, 1.71 mM) and $^t$BuOK in tetrahydrofuran (3.42 mL, 1.0M solution). The reaction was left stirring for 18 hours, then diluted with water (100 mL) and the products extracted into ethyl acetate (3×500 mL). The combined organic phases were dried (MgSO$_4$) and evaporated to dryness. The product was purified on SiO$_2$ eluting with 2-8% ethyl acetate in isohexane to obtain pure product, 0.18 g. ¹H NMR (360 MHz, CDCl₃) δ 7.49-7.47 (1H, m), 7.42 (1H, d, J=2 Hz), 7.27-7.25 (1H, m), 7.13-7.04 (2H, m), 6.90-6.83 (1H, m), 2.90-2.60 (2H, m), 2.12-2.04 (2H, m), 1.83-1.80 (2H, m), 1.64-1.56 (1H, m) and 1.40-1.15 (3H m).

Example 43

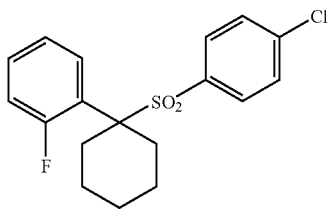

Prepared as for Example 42, using Intermediate 6.

¹H NMR (360 MHz, CDCl₃) δ 7.38-7.27 (6H, m), 7.14 (1H, t, J=1.3 and 7.8 Hz), 6.90-6.83 (1H, m), 2.80-2.60 (2H, m), 2.14-2.04 (2H, m), 1.80-1.77 (2H, m), 1.61-1.55 (1H, m) and 1.38-1.15 (3H, m).

Example 44

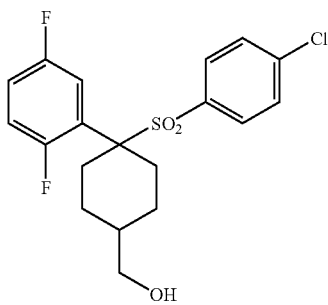

(1:1 mix of cis and trans)

Borane-tetrahydrofuran complex (1M in tetrahydrofuran, 2 mL, 2 mmol) was added to a solution of the olefin from Example 40 (383 mg, 1 mmol) in tetrahydrofuran (15 mL) and the mixture was stirred at room temperature for 3 h. Aqueous sodium hydroxide (4M, 2.5 mL) and aqueous hydrogen peroxide (27%, 2.5 mL) were added and the mixture was stirred at room temperature for 2 h. Water was added and the mixture was extracted with ethyl acetate. The combined organic fractions were dried (MgSO₄) and the solvent was evaporated under reduced pressure to give the desired product as a white foam (350 mg, 88%) as a 1:1 mixture of cis and trans isomers. ¹H NMR (360 MHz, CDCl₃) δ 7.39-7.31 (8H, m), 7.11-7.01 (4H, m), 6.88-6.81 (2H, m), 3.73 (2H, d, J=7.5 Hz), 3.35 (2H, d, J=6.2 Hz), 2.42-2.30 (4H, m), 2.23-2.12 (2H, m), 1.91-1.85 (4H, m), 1.77-1.67 (4H, m), 1.51-1.45 (2H, m), 1.02-0.89 (2H, m).

Example 45

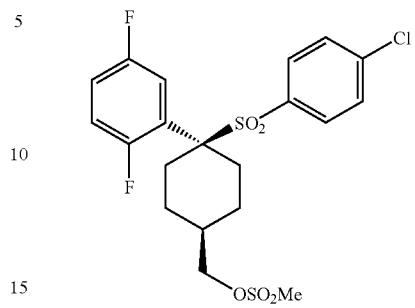

Methanesulfonyl chloride (77 μL, 0.998 mmol) was added to a solution of the cis and trans alcohol mixture from Example 44 (200 mg, 0.499 mmol) and triethylamine (208 μL, 1.50 mmol) in dichloromethane (10 mL) and the mixture was stirred at room temperature for 24 h. The solvent was evaporated under reduced pressure and the residue was dissolved in ethyl acetate. The mixture washed with aqueous citric acid (10%), aqueous sodium hydroxide (1M), dried (MgSO₄) and the solvent was evaporated under reduced pressure. The residue was purified by flash column chromatography on silica gel, eluting with isohexane:EtOAc (20:80), to give the product as a white foam (105 mg, 44%). ¹H NMR (400 MHz, DMSO-d₆) δ 7.62-7.60 (2H, m), 7.35-7.33 (3H, m), 7.21-7.09 (2H, m), 4.24 (2H, d, J=7.6 Hz), 3.21 (3H, s), 2.51-2.44 (2H, m), 2.27-2.18 (2H, m), 1.98-1.89 (1H, m), 1.81-1.73 (2H, m), 1.46-1.35 (2H, m).

Example 46

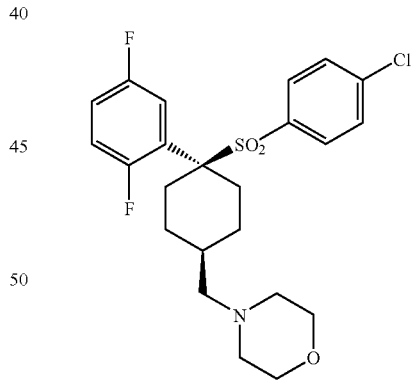

Morpholine (91 μL, 1.04 mmol) was added to a solution of the cis-mesylate from Example 45 (50 mg, 0.104 mmol) in acetonitrile (2 mL) and the mixture was stirred at 80° C. for 3 days. The mixture was cooled and the solvent was evaporated under reduced pressure and the residue was dissolved in ethyl acetate. The mixture washed with aqueous sodium hydroxide (1M), dried (MgSO₄) and the solvent was evaporated under reduced pressure. The residue was purified by flash column chromatography on silica gel, eluting with isohexane:EtOAc (1:1), to give the product as a white foam (30 mg, 61%). ¹H NMR (360 MHz, CD$_3$OD) δ 7.51-7.48 (2H, m), 7.44-7.38 (2H, m), 7.19-7.09 (2H, m), 7.00-6.93 (1H, m), 3.70-3.67 (4H, m), 2.56-2.24 (10H, m), 1.85-1.81 (3H, m), 1.50-1.42 (2H, m).

Example 47

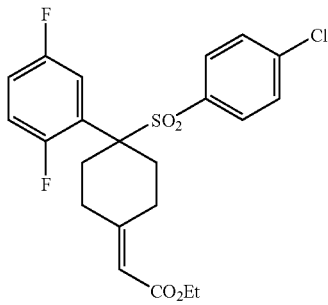

Ethyl(diethoxyphosphinyl)acetate (5.16 mL, 26 mmol) was added dropwise to a slurry of sodium hydride (60% dispersion in mineral oil, 988 mg, 24.7 mmol) in tetrahydrofuran (60 mL) and the mixture was stirred at room temperature for 1 h. The ketone from Example 2 (5 g, 13 mmol) in tetrahydrofuran (50 mL) was added dropwise over 20 min. and the mixture was stirred at room temperature for 18 h. Water was added and the mixture was extracted with ethyl acetate. The combined organic fractions were washed with water, dried (MgSO$_4$) and the solvent was evaporated under reduced pressure. The residue was purified by flash column chromatography on silica gel, eluting with isohexane:EtOAc (85:15), to give the product as a white solid (5.2 g, 88%). $^1$H NMR (400 MHz, CDCl$_3$) δ 7.41-7.36 (4H, m), 7.18-7.13 (1H, m), 7.11-7.05 (1H, m), 6.93-6.86 (1H, m), 5.64 (1H, s), 4.14-4.10 (2H, m), 3.99-3.96 (1H, m), 2.91-2.80 (2H, m), 2.42-2.38 (1H, m), 2.31-2.04 (3H, m), 1.89-1.78 (1H, m), 1.28-1.24 (3H, m).

Example 48

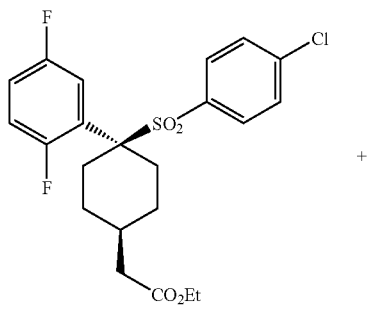

+

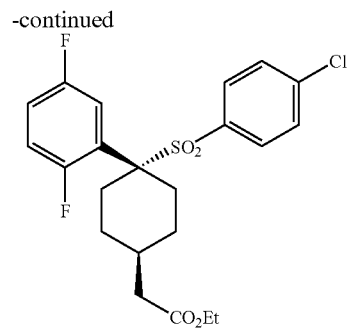

Sodium borohydride (313 mg, 8.23 mmol) was added to a mixture of the unsaturated ester from Example 47 (3.74 g, 8.23 mmol) and nickel (II) chloride (2.67 g, 20.6 mmol) in ethanol (100 mL). The mixture was stirred at room temperature for 20 min., then water (100 mL) was added. The mixture was filtered through Hyflo™, washing with ethanol and ethyl acetate. The solvent was evaporated under reduced pressure and the residue was partitioned between ethyl acetate and water. The organic layer was collected, dried (MgSO$_4$) and the solvent was evaporated under reduced pressure. The residue was purified by flash column chromatography on silica gel, eluting with isohexane:EtOAc (85:15), to give the faster running cis-isomer, as an oil (1.36 g, 36%), $^1$H NMR (400 MHz, CDCl$_3$) δ 7.37-7.30 (4H, m), 7.09-7.00 (2H, m), 6.86-6.79 (1H, m), 4.14 (2H, q, J=7.1 Hz), 2.47 (2H, d, J=7.6 Hz), 2.46-2.38 (2H, m), 2.19-2.14 (1H, m), 1.76-1.71 (2H, m), 1.57-1.48 (4H, m), 1.27 (3H, t, J7.1 Hz);

and the slower running trans-isomer, as an oil (200 mg, 5.3%). $^1$H NMR (400 MHz, CDCl$_3$) δ 7.39-7.34 (4H, m), 7.10-7.03 (2H, m), 6.88-6.82 (1H, m), 4.08 (2H, q, J=7.1 Hz), 2.98-2.85 (1H, m), 2.67-2.53 (1H, m), 2.22-2.11 (2H, m), 2.06 (2H, d, J=6.9 Hz), 2.01-1.85 (3H, m), 1.20 (3H, t, J=7.1 Hz), 1.01-0.90 (2H, m).

Example 49

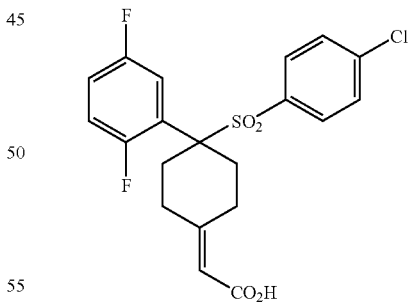

Lithium hydroxide (132 mg, 5.5 mmol) was added to a solution of the unsaturated ester from Example 47 (500 mg, 1.1 mmol) in ethanol (40 mL). The mixture was degassed and stirred at room temperature under nitrogen gas for 24 h. The mixture was poured into aqueous hydrochloric acid (1M) and extracted with ethyl acetate. The organic extract was dried (MgSO$_4$) and the solvent was evaporated under reduced pressure to give the product as a white solid (430 mg, 92%). $^1$H NMR (400 MHz, CD$_3$OD) δ 7.53-7.51 (2H, m), 7.45-7.39 (2H, m), 7.27-7.18 (2H, m), 7.07-7.00 (1H, m), 5.67 (1H, s), 3.97-3.93 (1H, m), 2.96-2.90 (2H, m), 2.47-2.43 (1H, m), 2.26-2.09 (3H, m), 1.84-1.77 (1H, m).

Example 50

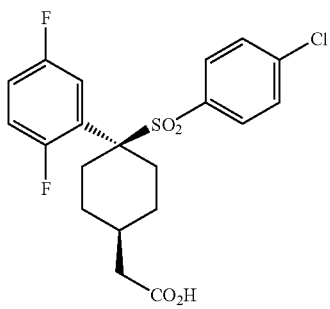

Lithium hydroxide (350 mg, 14.57 mmol) was added to a solution of the cis-ester from Example 48, (1.33 g, 2.91 mmol) in ethanol (40 mL). The mixture was degassed and stirred at room temperature under nitrogen gas for 5 h. The mixture was poured into aqueous hydrochloric acid (1M) and extracted with ethyl acetate. The organic extract was dried (MgSO$_4$) and the solvent was evaporated under reduced pressure to give a white solid which was then crystallized from IPA to give the product as a white solid (950 mg, 76%). $^1$H NMR (400 MHz, CD$_3$OD) δ 7.51-7.49 (2H, m), 7.40-7.37 (2H, m), 7.19-7.10 (2H, m), 7.00-6.94 (1H, m), 2.51-2.35 (6H, m), 2.13-2.10 (1H, m), 1.78-1.74 (2H, m), 1.57-1.50 (2H, m).

Example 51

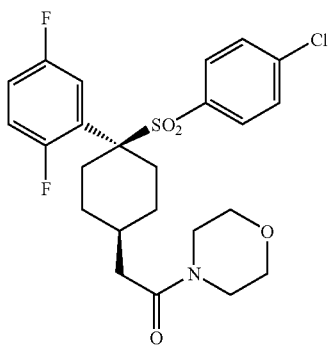

The acid from Example 50 (50 mg, 0.117 mmol), morpholine (30 μL, 0.351 mmol), 1-hydroxybenzotriazole (24 mg, 0.176 mmol) and triethylamine (65 μL, 0.468 mmol) was stirred in tetrahydrofuran at room temperature under nitrogen gas for 10 min. 1-(3-Dimethylaminopropyl)-3-ethylcarbodiimide hydrochloride (45 mg, 0.234 mmol) was added to the mixture and stirred for 24 h. The mixture was poured into aqueous sodium hydroxide (1M) and extracted with ethyl acetate. The organic extract was dried (MgSO$_4$) and the solvent was evaporated under reduced pressure. The residue was purified by flash column chromatography on silica gel, eluting with 5 to 10% methanol in dichloromethane, to give the product as a white foam (50 mg, 86%).

$^1$H NMR (400 MHz, CD$_3$OD) δ 7.50 (2H, d, J=8.6 Hz), 7.37 (2H, d, J=8.6 Hz), 7.19-7.09 (2H, m), 7.00-6.93 (1H, m), 3.69-3.63 (4H, m), 3.59-3.56 (4H, m), 2.55 (2H, d, J=7.4 Hz), 2.47-2.39 (4H, m), 2.16-2.07 (1H, m), 1.78-1.74 (2H, m), 1.58-1.51 (2H, m). m/z (ES$^+$) (M+1) 498+500.

Examples 52-63

The following compounds were prepared according to the method of Example 51, using the appropriate amine in place of morpholine.

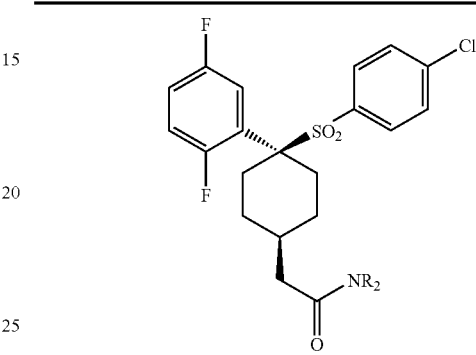

| Ex. | —NR$_2$ | Formula | M.W. | m/z (ES$^+$) (M + 1) |
|---|---|---|---|---|
| 52 | —N(piperazine)N— | C$_{25}$H$_{29}$ClF$_2$N$_2$O$_3$S | 510 512 | 511 513 |
| 53 | —N(piperazine)N-phenyl | C$_{30}$H$_{31}$ClF$_2$N$_2$O$_3$S | 572 574 | 573 575 |
| 54 | —N(piperidine)-OH | C$_{25}$H$_{28}$ClF$_2$NO$_4$S | 511 513 | 512 514 |
| 55 | —NH-CH$_2$CH$_2$-(2-pyridyl) | C$_{27}$H$_{27}$ClF$_2$N$_2$O$_3$S | 532 534 | 533 535 |
| 56 | —NH-CH$_2$CH$_2$CH$_2$-imidazolyl | C$_{26}$H$_{28}$ClF$_2$N$_3$O$_3$S | 535 537 | 536 538 |
| 57 | —N(piperidine)-CO$_2$Et | C$_{28}$H$_{32}$ClF$_2$NO$_5$S | 567 569 | 568 570 |
| 58 | —N(piperidine)-CO$_2$Et | C$_{28}$H$_{32}$ClF$_2$NO$_5$S | 567 569 | 568 570 |
| 59 | —N(piperidine)-CO$_2$Et | C$_{28}$H$_{32}$ClF$_2$NO$_5$S | 567 569 | 568 570 |

-continued

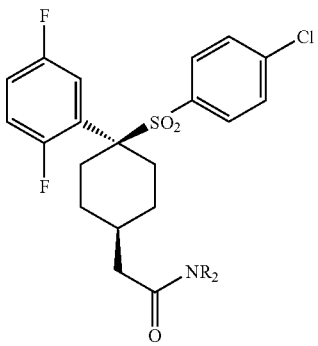

| Ex. | —NR₂ | Formula | M.W. | m/z (ES⁺) (M + 1) |
|---|---|---|---|---|
| 60 | piperidine-3-CO₂Et | $C_{28}H_{32}ClF_2NO_5S$ | 567, 569 | 568, 570 |
| 61 | piperidine | $C_{25}H_{28}ClF_2NO_3S$ | 495, 497 | 496, 498 |
| 62 | 3-methyl-piperidine-3-CO₂Et | $C_{29}H_{34}ClF_2NO_5S$ | 581, 583 | 582, 584 |
| 63 | 3-methyl-piperidine-3-CO₂Et | $C_{29}H_{34}ClF_2NO_5S$ | 581, 583 | 582, 584 |

Example 64

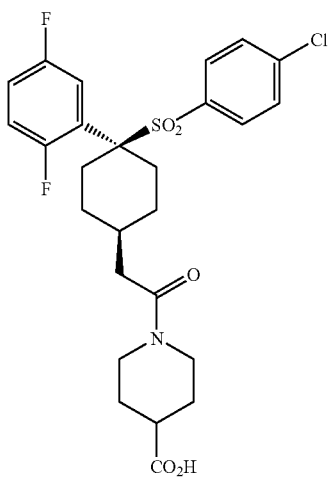

Lithium hydroxide (20 mg, 0.833 mmol) was added to a solution of Example 57 (95 mg, 0.167 mmol) in ethanol (12 ml) and water (4 ml). The mixture was degassed and stirred at room temperature under nitrogen gas for 18 h. The mixture was poured into aqueous hydrochloric acid (1M) and extracted with ethyl acetate. The organic extract was dried ($MgSO_4$) and the solvent was evaporated under reduced pressure to give the product as a white solid (75 mg, 83%). $^1$H NMR (400 MHz, $CD_3OD$) δ 7.50 (2H, d, J=8.6 Hz), 7.38 (2H, d, J=8.6 Hz), 7.19-7.10 (2H, m), 7.00-6.93 (1H, m), 4.37-4.32 (1H, m), 3.98-3.90 (1H, m), 3.26-3.18 (1H, m), 2.90-2.82 (1H, m), 2.64-2.38 (7H, m), 2.10-2.06 (1H, m), 2.00-1.91 (2H, m), 1.78-1.49 (6H, m). m/z (ES⁺) (M+1) 540+542.

Examples 65-69

The following compounds were prepared according to the method of Example 64 using the appropriate esters from Examples 58-63.

| Ex. | —NR₂ | Formula | M.W | m/z (ES⁺) (M + 1) |
|---|---|---|---|---|
| 65 | piperidine-3-CO₂H | $C_{26}H_{28}ClF_2NO_5S$ | 539, 541 | 540, 542 |
| 66 | piperidine-3-CO₂H | $C_{28}H_{32}ClF_2NO_5S$ | 539, 541 | 540, 542 |
| 67 | piperidine-3-CO₂H | $C_{28}H_{32}ClF_2NO_5S$ | 539, 541 | 540, 542 |
| 68 | 3-methyl-piperidine-3-CO₂H | $C_{27}H_{30}ClF_2NO_5S$ | 553, 555 | 554, 556 |
| 69 | 3-methyl-piperidine-3-CO₂H | $C_{27}H_{30}ClF_2NO_5S$ | 553, 555 | 554, 556 |

Example 70

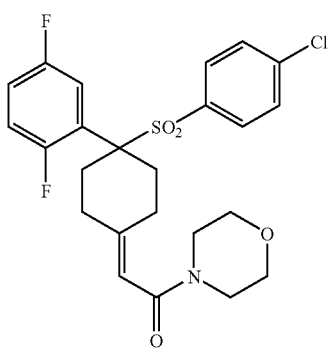

The acid from Example 49 (30 mg, 0.0703 mmol) was coupled with morpholine (18.4 µL, 0.211 mmol) following the procedure of Example 51 to give the product as a white foam (30 mg, 86%). $^1$H NMR (400 MHz, CD$_3$OD) δ 7.53-7.51 (2H, d, m), 7.45-7.41 (2H, d, m), 7.26-7.19 (2H, m), 7.07-7.00 (1H, m), 5.88 (1H, s), 3.64-3.58 (6H, m), 3.51-3.49 (2H, m), 2.98-2.92 (3H, m), 2.48-2.44 (1H, m), 2.23-2.06 (3H, m), 1.87-1.80 (1H, m).

Example 71

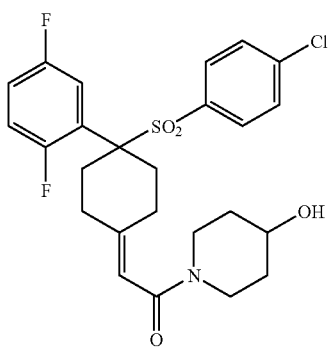

Prepared from the acid from Example 49 and 4-hydroxypiperidine according to the method of Example 51. $^1$H NMR (400 MHz, CD$_3$OD) δ 7.54-7.51 (2H, m), 7.43-7.41 (2H, m), 7.25-7.19 (2H, m), 7.07-7.00 (1H, m), 5.88 (1H, s), 4.12-4.02 (1H, m), 3.86-3.76 (2H, m), 3.26-3.12 (2H, m), 3.00-2.83 (3H, m), 2.48-2.44 (1H, m), 2.23-2.05 (3H, m), 1.87-1.78 (3H, m), 1.43-1.40 (2H, m).

Example 72

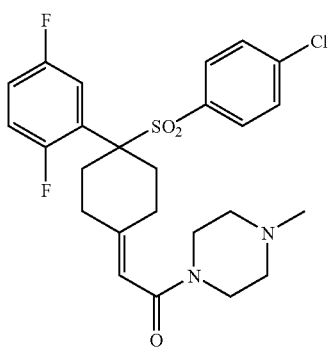

Prepared from the acid from Example 49 (30 mg, 0.0703 mmol) and 1-methylpiperazine (23 µL, 0.211 mmol) by the method of Example 51 to give the product as a white foam (25 mg, 70%). $^1$H NMR (400 MHz, CD$_3$OD) δ 7.53-7.51 (2H, m), 7.44-7.41 (2H, m), 7.25-7.19 (2H, m), 7.07-7.00 (1H, m), 5.88 (1H, s), 3.66-3.60 (2H, m), 3.53-3.48 (2H, m), 2.93-2.89 (3H, m), 2.48-2.39 (5H, m), 2.30 (3H, s), 2.23-2.08 (3H, m), 1.86-1.80 (1H, m). m/z (ES$^+$) (M+1) 509+511.

Examples 73-75

The following compounds were prepared according to the method of Example 70, using the appropriate amine in place of morpholine.

| Ex. | —NR$_2$ | Formula | M.W. | m/z (ES$^+$) (M+1) |
|---|---|---|---|---|
| 73 | —N(piperazinyl)-N-phenyl | C$_{30}$H$_{29}$ClF$_2$N$_2$O$_3$S | 570<br>572 | 571<br>573 |
| 74 | —NH-CH$_2$CH$_2$-(2-pyridyl) | C$_{27}$H$_{25}$ClF$_2$N$_2$O$_3$S | 530<br>532 | 531<br>533 |
| 75 | —NH-CH$_2$CH$_2$CH$_2$-(imidazolyl) | C$_{26}$H$_{26}$ClF$_2$N$_3$O$_3$S | 533<br>535 | 534<br>536 |

Examples 76-86

The following were prepared as mixtures of cis and trans isomers by the procedure outlined for Examples 5-16:

| Example No | —NR$_2$ | MS (MH+) |
|---|---|---|
| 76 | —N(piperazinyl)-N-(4-fluorophenyl) | 549 |

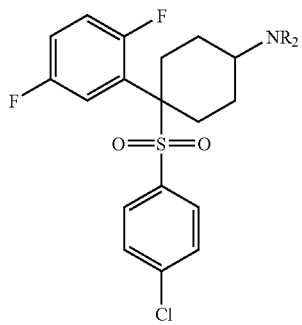

| Example No | —NR₂ | MS (MH+) |
|---|---|---|
| 77 | 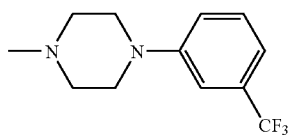 | 599 |
| 78 | 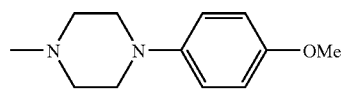 | 561 |
| 79 | 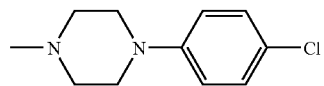 | 567 |
| 80 | 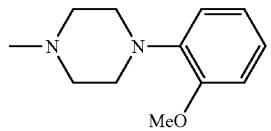 | 561 |
| 81 | 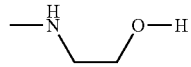 | 429 |
| 82 | 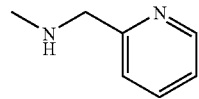 | 476 |
| 83 | 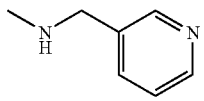 | 476 |
| 84 | 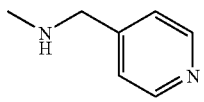 | 476 |
| 85 | 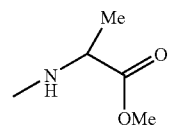 | 471 |

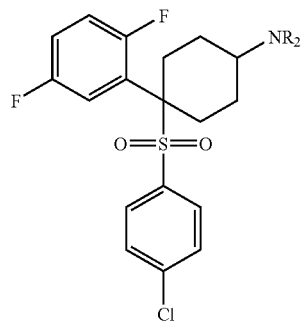

| Example No | —NR₂ | MS (MH+) |
|---|---|---|
| 86 | 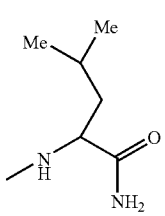 | 499 |

In the case of Examples 81-86, the cis and trans isomers were separated by flash chromatography using ethyl acetate/methanol mixtures.

Example 87

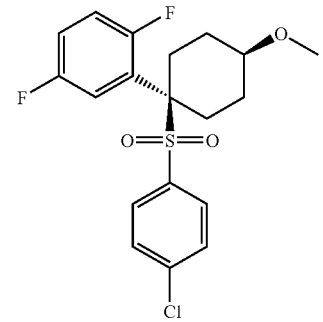

The cis alcohol from Example 22(b) (100 mg, 0.26 mmol) in dry THF was treated with NaH (60% dispersion, 16 mg, 0.39 mmol) and methyl iodide (0.2 ml, excess) and heated in a sealed tube at 70° C. for 18 h. The reaction was quenched with sat. aq. ammonium chloride and the products extracted with ethyl acetate (3×20 ml). The organics were washed with brine, dried (MgSO₄), filtered and evaporated. The crude oil was purified by flash chromatography eluting with 2:1 ʲhexane/ethyl acetate to give 35 mg of product.

$^1$H NMR δ (ppm) (CDCl₃): 1.26 (3 H, t, J=7.0 Hz), 1.99 (2 H, s), 2.04 (1 H, s), 2.48 (3 H, d, J=0.7 Hz), 3.26-3.32 (3 H, m), 6.82-6.90 (1 H, m), 7.01-7.13 (2H, m), 7.37 (4 H, s).

Example 88

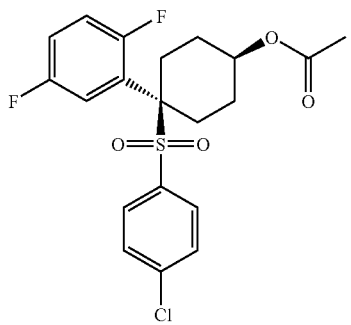

The cis alcohol from Example 22(b) (100 mg, 0.26 mmol) in dry DCM (5 ml) under nitrogen was treated with triethylamine (53 mg, 0.52 mmol) and acetyl chloride (41 mg, 0.52 mmol) using catalytic DMAP. The reaction was stirred at room temperature for 12 h. Reaction was diluted with DCM, washed with water, brine, dried (MgSO$_4$), filtered and evaporated. The crude oil was purified by flash chromatography eluting with 1:1 $^i$hexane/ethyl acetate) to give 45 mg of product. $^1$H NMR δ (ppm) (CDCl$_3$): 1.24 (1 H, d, J=6.3 Hz), 1.42 (2 H, t, J=14.7 Hz), 1.97 (1 H, s), 2.03 (1 H, d, J=10.9 Hz), 2.11 (3 H, s), 2.53 (3H, d, J=11.6 Hz), 4.88-4.91 (1 H, m), 6.82-6.89 (1 H, m), 7.03-7.12 (2 H, m), 7.35-7.37 (4H, m)

Example 89

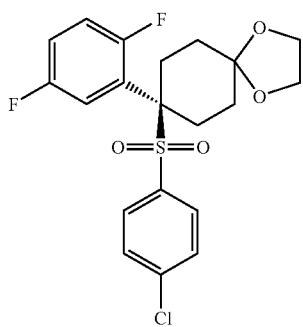

The ketone from Example 2 (200 mg, 0.52 mmol) in dry toluene (7 ml) was treated with ethanediol (0.1 ml, 1.56 mmol), p-toluenesulfonic acid (10 mg) and 4A molecular sieves (30 mg). The mixture was heated at reflux for 18 h. The reaction was neutralised with solid NaHCO$_3$, filtered and evaporated. The residue was dissolved in DCM, washed with aqueous NaHCO$_3$, dried (MgSO$_4$), filtered and evaporated. The crude oil was purified by flash chromatography (SiO$_2$, 2:1 $^i$hexane/ethyl acetate to 1:1) to give the product (65 mg).

$^1$H NMR δ (ppm) (CDCl$_3$): 1.24 (1 H, d, J=6.3 Hz), 1.42 (2 H, t, J=14.7 Hz), 1.97 (1 H, s), 2.03 (1 H, d, J=10.9 Hz), 2.11 (3 H, s), 2.53 (3H, d, J=11.6 Hz), 4.88-4.91 (1 H, m), 6.82-6.89 (1 H, m), 7.03-7.12 (2 H, m), 7.35-7.37 (4H, m)

Example 90

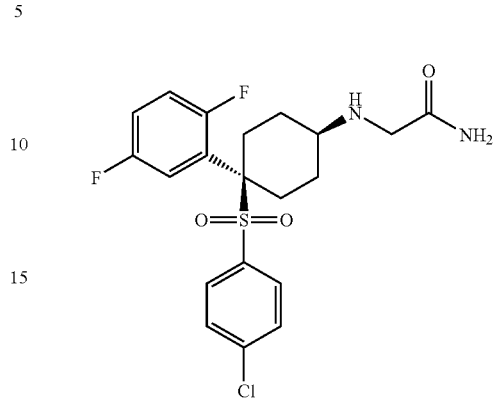

The cis amino-ester from Example 13 (100 mg, 0.23 mmol) (obtained by flash chromatography of the cis/trans mixture using ethyl acetate/methanol) was treated with a 2.0M solution of ammonia in methanol (3 ml). The solution was heated in a sealed tube for 18 hours, the reaction concentrated and the residue purified by flash chromatography (SiO$_2$, ethyl acetate to 3:1 ethyl acetate/methanol to give 70 mg. product amide. $^1$H NMR δ (ppm) (CDCl$_3$): 1.41-1.49 (2 H, m), 1.79-1.83 (2 H, m), 2.42-2.58 (4 H, m), 2.76 (1 H, t, J=3.1 Hz), 3.28 (2 H, s), 5.43-5.47 (1 H, m), 6.81-6.88 (1 H, m), 6.98-7.11 (2H, m), 7.32-7.38 (4H, m).

Example 91

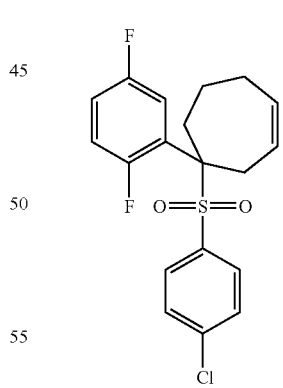

Prepared from Intermediate 7 (2.10 g, 5.12 mmol), using the method of Example 34. Yield 2.00 g. $^1$H NMR (400 MHz, CDCl$_3$), 1.28-1.35 (1H, m), 1.81-1.87 (1H, m), 2.14-2.18 (2H, m), 2.30-2.37 (1H, m), 2.86-2.90 (1H, m), 3.04-3.07 (1H, m), 3.30-3.36 (1H, m), 5.63-5.68 (1H, m), 5.79-5.84 (1H, m), 6.81-6.87 (1H, m), 6.92-7.04 (2H, m), 7.37 (4H, s).

Example 92

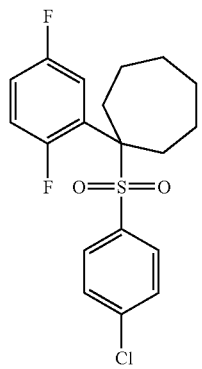

The product of Example 91 (57.8 mg, 0.151 mmol) in ethyl acetate (5 ml) was hydrogenated by the method of Example 35 to give the cycloheptane (46 mg). $^1$H NMR (400 MHz, CDCl$_3$), 1.38-1.46 (4H, m), 1.51-1.60 (2H, m), 1.84-1.92 (2H, m), 2.32-2.39 (2H, m), 2.67-2.72 (2H, m), 6.85-6.91 (1H, m), 6.98-7.06 (2H, m), 7.33-7.38 (4H, m).

Example 93

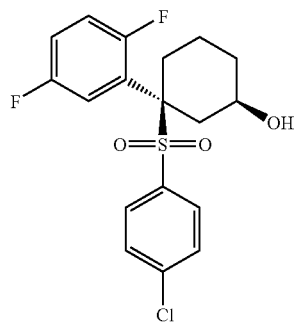

The cyclohexene from Example 34 (352 mg, 0.957 mmol) in tetrahydrofuran (6 ml) was treated with borane-tetrahydrofuran complex (1M in tetrahydrofuran, 4.8 ml, 4.78 mmol) at 0° C. Hydrogen peroxide (27% w/w in water, 10 ml) was mixed with sodium hydroxide solution (4N, 10 ml), then added slowly to the reaction and stirring continued for a further hour at room temperature. The reaction mixture was extracted with ethyl acetate (2×100 ml), and the combined organics washed with brine (sat., 100 ml), dried (MgSO$_4$) and evaporated in vacuo to give 415 mg mixture of 4 isomers. The isomers were separated by chromatography on silica, eluting with 30-50% ethyl acetate in hexanes. Fractions rich in 3-hydroxy isomers (198 mg) were purified by preparative t.l.c, eluting with 30% ethyl acetate in hexanes followed by two crystallisations from diethyl ether in hexanes to give the cis-3-alcohol product. 1.9 mg. $^1$H NMR (400 MHz, CDCl$_3$), 1.23-1.39 (2H, m), 1.89-2.09 (4H, m), 2.55-3.10 (2H, br), 3.48-3.54 (1H, m), 6.82-6.89 (1H, m), 7.02-7.25 (2H, m), 7.35-7.40 (4H, m).

Example 94

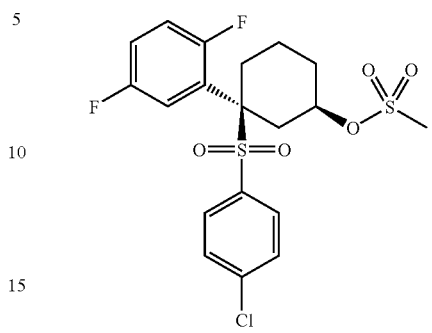

A mixture of cis-3- and cis-4-alcohols (2.52 g, 6.53 mmol) (from Example 93) in dichloromethane (80 ml) at 0° C. was treated with triethylamine (1.36 ml, 9.79 mmol) then methansulfonyl chloride (603 µl, 7.83 mmol). The mixture was stirred for 3.5 hours, slowly warming to room temperature, then washed with water (200 ml), citric acid (10% aq., 200 ml) and sodium hydrogen carbonate (sat. aq., 200 ml), dried (MgSO$_4$) and evaporated in vacuo to give 2.97 g mixture of 2 isomers. Isomers were separated by chromatography on silica, eluting with 100% dichloromethane giving cis-3-mesylate (182 mg), cis-4 mesylate (185 mg) and mixed fractions (2.19 g). Cis-3-mesylate (52 mg) was purified by preparative t.l.c., eluting with 100% dichloromethane to give product. 48 mg. $^1$H NMR (400 MHz, CDCl$_3$), 1.24-1.31 (1H, m), 1.63 (1H, dq, J=4.4 Hz and J=12.4 Hz), 1.96-2.20 (3H, br), 2.31 (1H, dt, J=2.4 Hz and J=12.4 Hz), 2.50-2.90 (1H, br), 3.01 (3H, s), 3.10-3.25 (1H, br), 4.40-4.54 (1H, m), 6.88-6.93 (1H, m), 7.07-7.11 (2H, m), 7.34-7.41 (4H, m).

Example 95

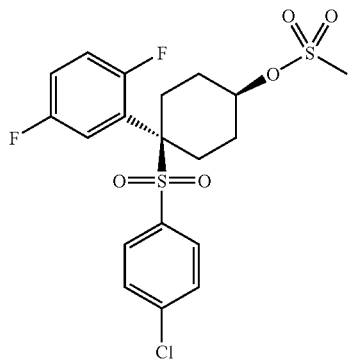

The cis-4-mesylate fraction from Example 94 (46 mg) was purified by preparative t.l.c., eluting with 100% dichloromethane to give product. 31 mg. $^1$H NMR (400 MHz, CDCl$_3$), 1.40-1.10 (2H, br), 2.15-2.25 (2H, br), 2.50-2.60 (4H, br), 3.08 (3H, s), 4.89 (1H, t, J=2.8 Hz), 6.80-6.90 (1H, m), 7.06-7.10 (2H, m), 7.33-7.40 (4H, m).

Example 96

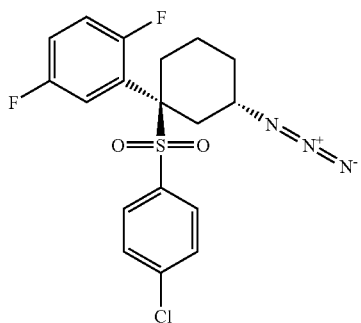

Cis-3-mesylate from Example 94 (66 mg, 0.142 mmol) in N,N-dimethylformamide (2 ml) was treated with sodium azide (14 mg, 0.213 mmol) and the mixture heated to 95° C. for 16 hours. A further portion of sodium azide (9 mg, 0.142 mmol) was added and stirring at 95° C. continued for a further 24 hours. The reaction was diluted with water (40 ml), extracted with 20% ethyl acetate in diethyl ether (3×60 ml) and the combined organics washed with brine (sat., 100 ml), dried (MgSO$_4$) and evaporated in vacuo to give 46 mg crude product. This was purified by chromatography on silica, eluting with 15% ethyl acetate in hexanes to give 12 mg product which was further purified by preparative t.l.c., eluting with 15% ethyl acetate in hexanes to give pure product. 7.2 mg. $^1$H NMR (400 MHz, CDCl$_3$), 1.62-1.71 (2H, m), 1.82-1.95 (2H, m), 2.30-2.50 (2H, br), 2.65-2.82 (2H, br), 4.18-4.23 (1H, m), 6.79-6.86 (1H, m), 6.70-7.04 (2H, m), 2.28-2.38 (4H, m).

Example 97

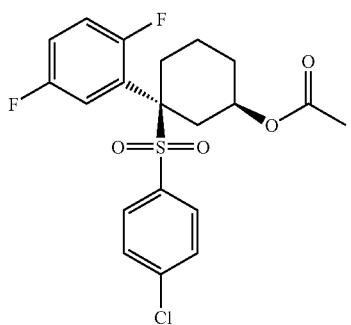

A mixture of cis-3- and trans-3-alcohols (650 mg, 1.68 mmol, isomer ratio 3:1) (from Example 93) in dichloromethane (20 ml) was treated with acetic anhydride (159 μl, 1.68 mmol) and dimethylaminopyridine (21 mg, 0.168 mmol). After 1 hour stirring at room temperature, the reaction was quenched with water (30 ml), washed with citric acid (10% aq., 30 ml) then sodium hydrogen carbonate (sat., aq., 30 ml). The organics were dried (MgSO$_4$) and evaporated in vacuo to give 843 mg mixture of isomers. Separation by chromatography on silica, eluting with 15-20% ethyl acetate in hexanes, gave the cis-isomer (209 mg). $^1$H NMR (360 MHz, CDCl$_3$), 1.20-1.50 (2H, br), 1.90-2.00 (2H, br), 2.05 (3H, s), 2.05-2.20 (2H, br), 2.50-3.05 (2H, br), 4.54-4.60 (1H, br), 6.82-6.90 (1H, m), 7.02-7.08 (2H, m), 7.33-7.39 (4H, m).

Example 98

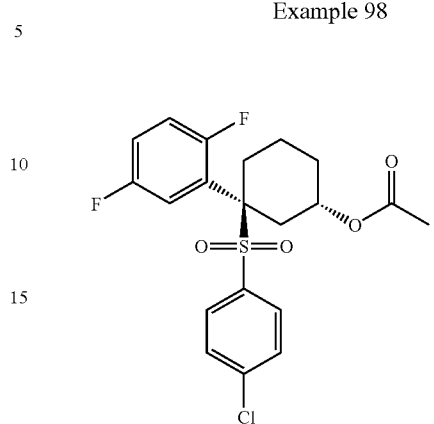

The trans-acetate fraction from Example 97 (220 mg) was purified by chromatography on silica, eluting with 100% dichloromethane, then 20% ethyl acetate in hexanes to give 90 mg material which was further purified by preparative t.l.c., eluting with 5% ethyl acetate in dichloromethane to give product. 49 mg. $^1$H NMR (400 MHz, CDCl$_3$), 1.55-1.88 (3H, m), 2.09 (3H, s), 2.28-2.36 (1H, m), 2.49-2.54 (1H, m), 2.58-2.65 (1H, br), 2.92-3.04 (2H, m), 5.40-5.44 (1H, m), 6.79-6.84 (1H, m), 7.01-7.07 (2H, m), 7.31-7.38 (4H, m).

Example 99

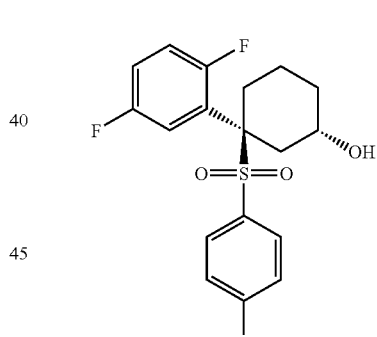

A degassed solution of trans-3-acetate from Example 98 (44 mg, 0.103 mmol) in methanol/water/tetrahydrofuran (3:1:1, 2 ml) was treated with lithium hydroxide (12 mg, 0.50 mmol). After 1 hour stirring at room temperature, a further portion of lithium hydroxide (12 mg, 0.50 mmol) was added, and after stirring at room temperature for 16 hours, the reaction was heated to 75° C. for 4 hours, cooled, diluted with water (10 ml), acidified with hydrochloric acid (1N, 3 ml), then extracted with ethyl acetate (3×20 ml). The combined organics were washed with brine (sat., 70 ml), dried (MgSO$_4$) and evaporated to give 35 mg crude product. This was purified by preparative t.l.c., eluting with 30% ethyl acetate in hexanes to give product. 11.3 mg. $^1$H NMR (400 MHz, CDCl$_3$), 1.63-1.84 (4H, m), 2.31-2.36 (1H, br), 2.45-2.57 (2H, br), 2.84-2.92 (1H, br), 4.37-4.45 (1H, br), 6.77-6.84 (1H, m), 6.97-7.05 (2H, m), 7.29-7.38 (4H, m).

Example 100

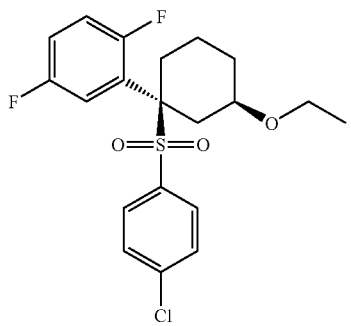

Cis-3-alcohol (Example 93) (49 mg, 0.128 mmol) in tetrahydrofuran (2 ml) was dripped into a stirring suspension of sodium hydride (5.6 mg, 60% w/w in mineral oil, 0.140 mmol) in tetrahydrofuran (1 ml) and the mixture heated to reflux for 2 hours. After cooling to 0° C., bromoethane (38 μl, 0.512 mmol) was added, the mixture stirred at room temperature for 16 hours, then further portions of sodium hydride (11 mg, 60% w/w in mineral oil, 0.256 mmol) and bromoethane (29 μl, 0.384 mmol) were added. After stirring at reflux for 24 hours, the reaction was cooled to room temperature, acidified with hydrochloric acid (2N, 2 ml) and extracted with diethyl ether (3×20 ml). The combined organics were washed with brine (sat., 50 ml), dried (MgSO$_4$) and evaporated to give 86 mg crude product. This was purified by preparative t.l.c., eluting with 30% ethyl acetate in hexanes to give product. 10 mg. $^1$H NMR (360 MHz, CDCl$_3$), 1.15-1.35 (6H, m), 1.87-2.04 (4H, m), 2.50-2.80 (1H, br), 3.06-3.20 (1H, br), 3.42-3.56 (2H, m), 6.84-6.91 (1H, m), 7.02-7.15 (2H, m), 7.39 (4H, s).

Example 101

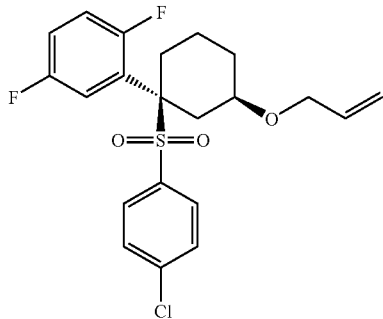

Prepared by the method of Example 100, substituting allyl bromide for bromoethane. The crude product was purified by preparative t.l.c., eluting with 15% ethyl acetate in hexanes to give product. 23 mg. $^1$H NMR (360 MHz, CDCl$_3$), 1.15-1.40 (3H, m), 1.85-2.02 (4H, m), 2.50-3.00 (1H, br), 3.12-3.24 (1H, br), 3.98-4.00 (2H, m), 5.14-5.26 (2H, m), 5.82-5.95 (1H, m), 6.84-6.90 (1H, m), 7.03-7.08 (2H, m), 7.40 (4H, s).

Example 102

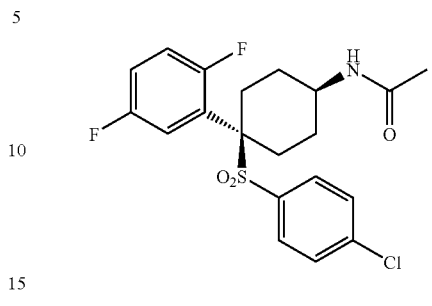

The amine from Example 39 (50 mg, 0.13 mmol) was dissolved in dichloromethane (1 mL) and was treated with triethylamine (27 μL, 0.2 mmol) and then acetic anhydride (18 μL, 0.2 mmol) and the mixture was stirred at r.t. for 24 hrs. The mixture was diluted with water (2 mL) and separated on a Bond Elut™ cartridge before purifying by preparative t.l.c to give the amide. $^1$H NMR (CDCl$_3$) 7.36 (2H, d, J=8.6 Hz), 7.29 (2H, d, J=9.3 Hz), 7.08-7.03 (2H,m), 6.88-6.83 (1H,m), 5.98-5.96 (1H, m), 4.04-4.01 (1H, m), 2.58-2.50 (2H, m), 2.41-2.34 (2H, m), 2.04 (3H, s), 1.97-1.91 (2H, m) and 1.54-1.46 (2H, m).

Example 103

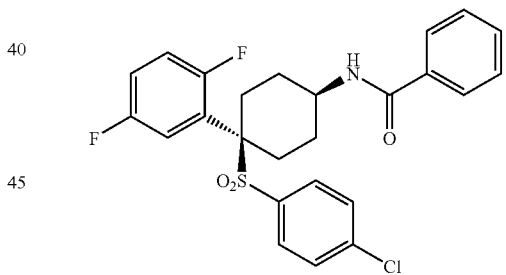

The amine from Example 39 (50 mg, 0.13 mmol) was dissolved in dichloromethane (1 mL) and was treated with triethylamine (54 μL, 0.4 mmol), benzoic acid (21 mg, 0.17 mmol) and 1-(3-dimethylaminopropyl)-3-ethylcarbodiimide hydrochloride (32 mg, 0.17 mmol) and the mixture was stirred at r.t. for 24 hrs. The mixture was diluted with water (2 mL) and separated on a Bond Elut™ cartridge before purifying by preparative t.l.c to give the amide. $^1$H NMR (CDCl$_3$) 7.77-7.72 (2H, m), 7.69-7.45 (3H, m), 7.39 (2H, d, J=11.2 Hz), 7.31 (2H, d, J=11.8 Hz), 7.26-7.03 (2H, m), 6.90-6.83 (1H, m), 6.43-6.40 (1H, m), 4.24-4.20 (1H, m), 2.63-2.58 (2H, m), 2.48-2.41 (2H, m), 2.12-2.07 (2H, m) and 1.68-1.54 (2H, m).

Example 104-107

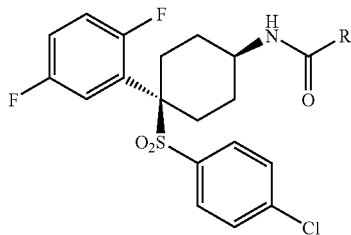

Using the method of Example 103, the following were prepared:

| Example | R | MS (MH+) |
|---|---|---|
| 104 | Dimethylaminomethyl | 470 (472) |
| 105 | 2-(piperidin-1-yl)ethyl | 525 (527) |
| 106 | 3-(dimethylamino)propyl | 499 (501) |
| 107 | (1H-imidazol-5-yl)methyl | 493 (495) |

Example 108

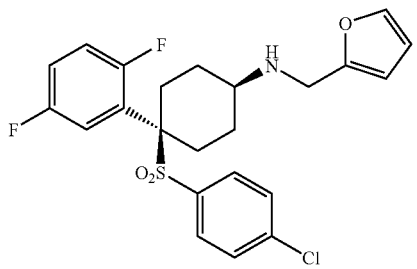

The amine from Example 39 (50 mg, 0.13 mmol) was dissolved in methanol (1 mL) and was treated with alumina (50 mg) and furfuraldehyde (2.5 µL, 0.26 mmol) and the mixture was stirred at r.t. for 16 hrs. Sodium borohydride was then added and the mixture was stirred for a further 16 hrs. The mixture was separated on a SCX Varian Bond Elut™ cartridge before purifying the basic fraction by preparative t.l.c to give the product. $^1$H NMR (CDCl$_3$) 7.38-7.32 (4H, m), 7.11-7.00 (2H, m), 6.87-6.80 (1H,m), 6.29 (1H, dd, J=2.8 and 1.6 Hz), 6.13 (1H, d, J=2.8 Hz), 3.76 (2H, s), 2.76-2.73 (1H, m), 2.64-2.56 (2H, m), 2.46-2.38 (2H, m), 1.82-1.76 (2H, m) and 1.41-1.34 (2H, m); MS MH+ 465(467).

Example 109

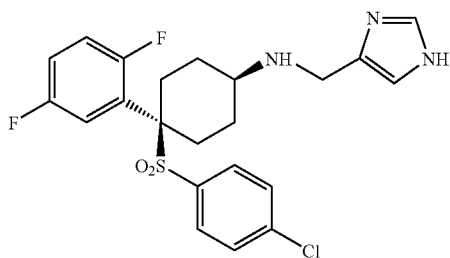

Prepared as in Example 108, substituting 4(5)-imidazole-carboxaldehyde for furfural. MS MH+ 465(467).

Example 110

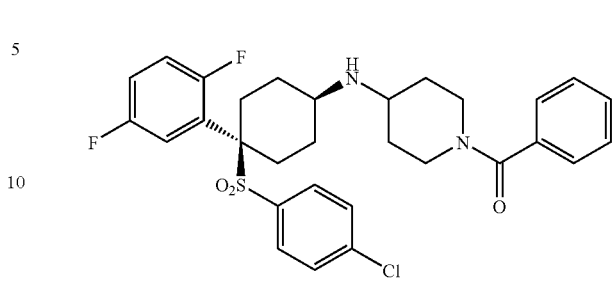

The amine from Example 39 (50 mg, 0.13 mmol) was dissolved in dichloroethane (1 mL) and treated with N-benzoyl-4-piperidone (53 mg, 0.26 mmol) and sodium triacetoxyborohydride (55 mg, 0.26 mmol) and the mixture was stirred at r.t. for 16 hrs. The mixture was diluted with saturated aqueous sodium bicarbonate (1 mL) and was separated on a Bond Elut™ cartridge before passing through a SCX Bond Elut™ cartridge. The basic fraction was purified by preparative t.l.c to give the amide.

$^1$H NMR (CDCl$_3$) 7.41-7.30 (9H, m), 7.10-7.01 (2H, m), 6.87-6.80 (1H,m), 4.62-4.50 (1H,m), 3.78-3.71 (1H, m), 3.08-2.91 (3H, m), 2.79-2.72 (1H, m), 2.61-2.43 (4H, m), 2.03-1.75 (4H, m) and 1.44-1.24 (4H, m); MS MH+ 573 (575).

Example 111

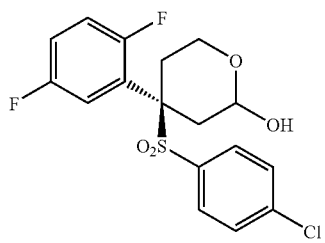

The cyclopentene from Example 31 (296 mg, 0.84 mmol) was dissolved in dichloromethane (40 mL), methanol (40 mL) and was stirred at −78° C. and purged with oxygen over 5 mins followed by bubbling through ozone until the blue colour persisted. The solution was then re-purged with oxygen and treated with sodium borohydride (316 mg, 8.4 mmol), and allowed to warm to r.t. over 16 hrs. The solvent was removed in vacuo and the residue was partitioned between ethyl acetate (100 mL) and saturated aqueous sodium bicarbonate (100 mL). The organic layer was separated, dried (MgSO$_4$) and evaporated. The yellow oil obtained was purified by column chromatography on silica gel eluting with 20-100% ethyl acetate in hexanes, to give the lactol. $^1$H NMR (CDCl$_3$) 7.41-7.30 (4H, m), 7.15-7.06 (2H, m), [1H, 5.48-5.46 (m) and 4.60 (d, J=8.8 Hz)], [1H, 4.11-4.07 (m) and 3.91-3.98(m)], 3.41-3.40 (2H, m), and 2.95-2.12 (3H,m)

Example 112

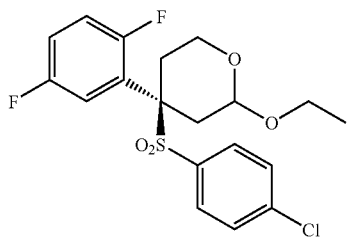

The lactol from Example 111 (30 mg, 0.07 mmol) was dissolved in dichloromethane (3 mL), methanol (1 mL) and was treated with Amberlyst 15 (10 mg) at r.t. over 16 hrs. The mixture was filtered and evaporated to give a pale oil (30 mg) which was purified by preparative t.l.c to give the ethyl acetal. $^1$H NMR (CDCl$_3$) 7.40-7.26 (4H, m), 7.02-6.88 (2H, m), 6.80-6.73 (1H, m), [1H, 5.01-4.99 (m) and 4.26 (d, J=8.8 Hz)], [2H, 4.11-4.07 (m) and 3.87-3.78(m)], 3.49-3.18 (2H, m), 2.90-2.16 (4H,m) and [3H, 1.20 (t, J=6.8 Hz) and 0.80 (t, J=7.2)]

Example 113

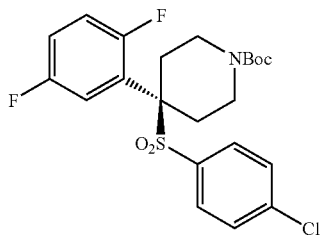

Intermediate 1 (2.5 g, 8.3 mmol) was dissolved in dimethylformamide (6 mL), and added dropwise to a suspension of 60% sodium hydride in mineral oil (635 mg 16.6 mmol) in dimethylformamide (6 mL). When the effervescence had ceased the solution was treated with a solution of N—Boc-bis-(2-chloroethyl)amine (3.75 g, 12 mmol) in dimethylformamide (3 mL). The mixture was stirred at r.t. for 36 hrs. Water (800 mL) was added and the solution washed with ethyl acetate (2×500 mL). The organic phase washed with brine (500 mL), dried (MgSO$_4$) and evaporated. The clear oil obtained was purified by column chromatography on silica gel eluting with 5-20% ethyl acetate in hexanes. The oil obtained was then further purified by column chromatography on silica gel eluting with dichloromethane to give the Boc-piperidine. $^1$H NMR (CDCl$_3$) 7.41-7.34 (4H, m), 7.13-7.05 (2H, m), 6.91-6.83 (1H, m), 4.25-4.15 (2H, m), 2.72-2.56 (4H, m), 2.34-2.23 (2H, m) and 1.43 (9H, s)

Example 114

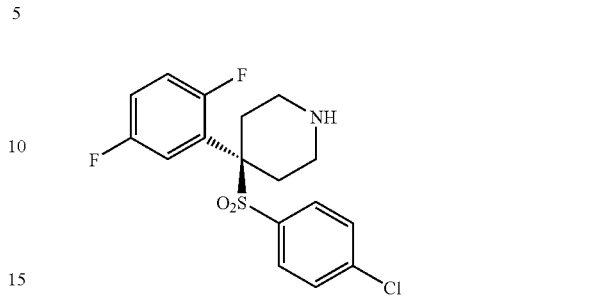

The Boc piperidine from Example 113 (300 mg, 0.64 mmol) was dissolved in dichloromethane (150 mL), and was treated with trifluoroacetic acid (30 mL). The mixture was stirred at r.t. for 30 mins and then the solvent was removed in vacuo and saturated aqueous sodium bicarbonate (100 mL) was added. The solution washed with dichloromethane (3×100 mL). The organic phase was dried (MgSO$_4$) and evaporated, to give the piperidine as a white solid. $^1$H NMR (CDCl$_3$) 7.40-7.36 (4H, m), 7.12-7.03 (2H, m), 6.91-6.84 (1H, m), 3.18-3.14 (2H, m), 2.75-2.54 (4H, m) and 2.30-2.24 (2H, m); MS MH+=371(373).

Example 115

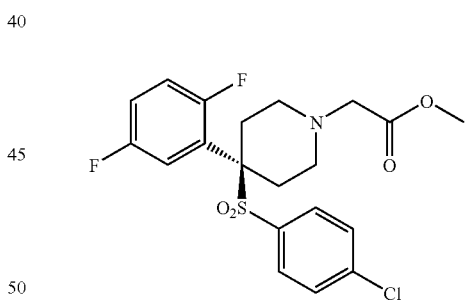

The piperidine from Example 114 (100 mg, 0.3 mmol) was dissolved in toluene (3 mL) and ethyl acetate (2 mL) and was treated with methyl bromoacetate (125 µL, 1.5 mmol) and was heated at 90° C. for 1 hr. The solvent was evaporated and the clear oil obtained was purified by column chromatography on silica gel eluting with 5-20% ethyl acetate in hexanes, to give the N-alkylpiperidine. $^1$H NMR (CDCl$_3$) 7.43-7.38 (4H, m), 7.13-7.04 (2H, m), 6.91-6.84 (1H, m), 3.66(3H, s), 3.12 (2H, s), 3.02-2.97 (2H, m), 2.90-2.60 (2H, m), 2.51-2.44 (2H, m) and 2.22-2.15 (2H, m); MS MH+=443(445).

Example 116

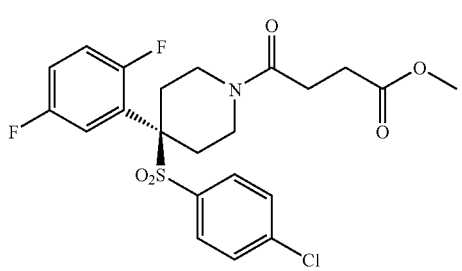

The piperidine from Example 114 (35 mg, 0.09 mmol) was dissolved in dichloromethane (2 mL) and was treated with triethylamine (20 μL, 0.14 mmol), methyl succinate monoester (15 mg, 0.11 mmol) and 1-(3-dimethylaminopropyl)-3-ethylcarbodiimide hydrochloride (24 mg, 0.12 mmol) and the mixture was stirred at r.t. for 24 hrs. The mixture was diluted with water (2 mL) and separated on a Bond Elut™ cartridge before purifying by preparative t.l.c to give the amide. $^1$H NMR (CDCl$_3$) 7.42-7.35 (4H, m), 7.14-7.07 (2H, m), 6.94-6.88 (1H, m), 4.70-4.64 (1H, m), 4.03-3.97 (1H, m), 3.67 (3H, s), and 3.08-2.25 (10H, m); MS MH+=485(487).

Example 117

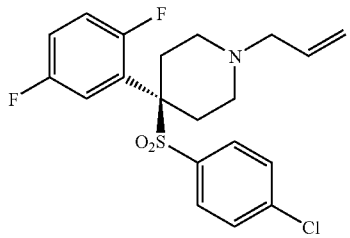

The piperidine from Example 114 (56 mg, 0.15 mmol) was dissolved in dimethylformamide (2 mL) and was treated with allyl bromide (17 μL, 0.18 mmol), and potassium carbonate (63 mg, 0.45 mmol) and the mixture was stirred at r.t. for 4 hrs. The mixture was diluted with water (2 mL) and the solution washed with ethyl acetate (3×10 mL). The organic phase was dried (MgSO$_4$) and evaporated to give a pale oil which was purified by column chromatography on silica gel eluting with 80% ethyl acetate in hexanes to give the N-allylpiperidine. $^1$H NMR (CDCl$_3$) 7.42-7.37 (4H, m), 7.13-7.02 (2H, m), 6.90-6.83 (1H, m), 5.83-5.71 (1H, m), 5.12-5.08 (2H, m), 2.99-2.95 (2H, m), 2.86 (2H, d, J=6.5 Hz), 2.84-2.38 (4H, m), and 1.91-1.85 (2H, m); MS MH+=412 (414).

Example 118

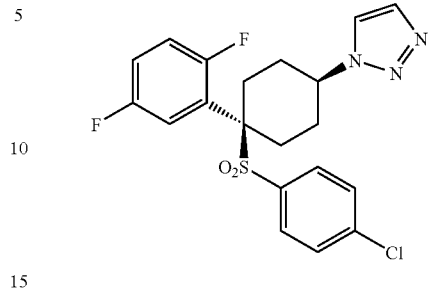

The azide from Example 38 (130 mg, 0.31 mmol) was dissolved in trimethylsilylacetylene (1.7 mL) and toluene (4 mL) and was heated at 90° C. for 7 hrs. The mixture was evaporated to dryness and purified by column chromatography on silica gel eluting with 20% ethyl acetate in hexanes to give the TMS triazole which was dissolved in tetrahydrofuran (16 mL) and was treated with acetic acid (0.3 mL) and TBAF (1M in tetrahydrofuran, 2 mL). The mixture was stirred at r.t. for 16 hrs. The solvent was removed in vacuo and saturated aqueous sodium bicarbonate (10 mL) was added. The solution washed with ethyl acetate (3×100 mL). The organic phase was dried (MgSO$_4$) and evaporated, to give a pale oil which was purified by column chromatography on silica gel eluting with 80% ethyl acetate in hexanes to give the triazole as a white solid. $^1$H NMR (CDCl$_3$) 7.77 (1H, s), 7.69 (1H, s), 7.39-7.32 (4H, m), 7.15-7.06 (2H, m), 6.91-6.86 (1H, m), 4.59-4.55 (1H, m), 3.28-3.23 (2H, m), 2.68-2.52 (5H, m) and 1.97-1.92 (2H, m); MS MH+=437(439).

Example 119

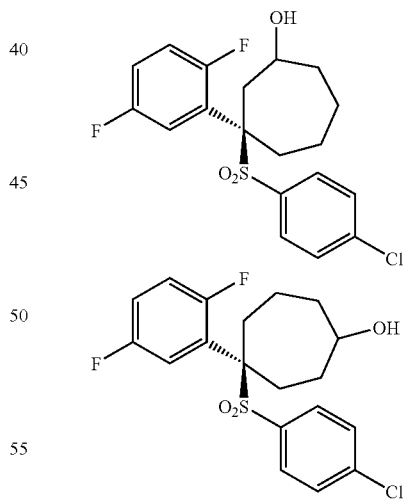

The cycloheptene from Example 91 (1.43 g, 3.75 mmol) in tetrahydrofuran (20 ml) at 0° C. was treated with borane (18.7 ml, 18.7 mmol, 1M solution in tetrahydrofuran), and the reaction mixture stirred for 1 hour at 0° C. Hydrogen peroxide (27% w/w in water, 30 ml) was mixed with sodium hydroxide solution (4N, 30 ml), then added slowly to the reaction, and stirring continued for a further hour, warming to room temperature. The reaction mixture was extracted with ethyl acetate (3×100 ml), and the combined organics were washed with brine (sat., 200 ml), dried (MgSO₄) and evaporated in vacuo to give 1.31 g mixture of isomeric cycloheptanols.

Example 120, 121

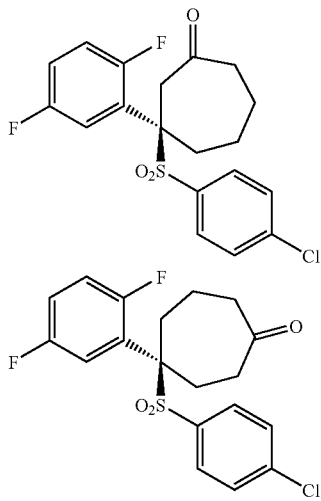

The cycloheptanol mixture from Example 119 (48 mg, 0.12 mmol) was dissolved in dichloromethane (5 mL) and treated with Dess-Martin periodinate (61 mg, 0.12 mmol), and the mixture stirred at r.t. for 1 hr. The mixture was diluted with saturated aqueous sodium bisulphite (5 mL) and after 15 mins was treated with saturated aqueous sodium bicarbonate, (10 mL) then extracted with dichloromethane (3×50 mL). The organic phase was dried (MgSO₄) and evaporated, to give a pale oil which was purified by preparative t.l.c to give the cycloheptan-3-one (Ex. 107): ¹H NMR (CDCl₃) 7.42-7.33 (4H, m), 7.11-7.01 (2H, m), 6.94-6.87 (1H, m), 3.66 (1H, dt, J=16.4 and 2.8 Hz), 2.50 (1H, dd, J=16.4 and 5.6 Hz), 2.32-2.16 (2H, m), 1.86-1.78 (2H, m), and 1.67-1.52 (2H, m);

and the cycloheptan-4-one (Ex. 108): ¹H NMR (CDCl₃) 7.41-7.34 (4H, m), 7.13-7.07 (1H, m), 7.01-6.97 (1H, m), 6.95-6.88 (1H, m), 3.06-3.00 (2H, m), 2.65-2.44 (4H, m), 2.41-2.33 (1H, m), 2.09-2.01 (1H, m), and 1.58-1.50 (2H, m).

Example 122

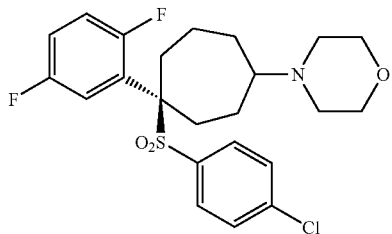

The ketone from Example 121 (40 mg, 0.1 mmol) was dissolved in dichloroethane (3 mL) and was treated with morpholine (16 mg, 0.26 mmol) and sodium triacetoxyborohydride (42 mg, 0.26 mmol) and the mixture stirred at r.t. for 16 hrs. The mixture was diluted with saturated aqueous sodium bicarbonate (1 mL) and was separated on a Bond Elut™ cartridge before passing through a SCX Bond Elut™ cartridge. The basic fraction was purified by preparative t.l.c to give the amine. ¹H NMR (CDCl₃) 7.38-7.31 (4H, m), 7.07-6.95 (2H, m), 6.91-6.84 (1H,m), 3.73-3.61 (5H,m) and 2.72-1.21 (11H, m); MS MH+ 469(471).

Example 123

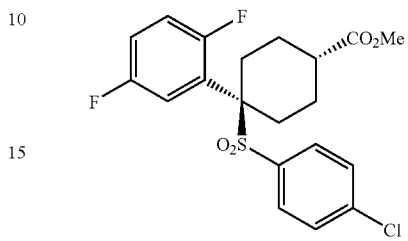

The cycloheptan-4-one from Example 121 (200 mg, 0.5 mmol) was dissolved in acetic acid (18 mL) and water (2 mL) and was treated with ceric ammonium nitrate (138 mg, 0.25 mmol) and bromine (40 mg, 0.25 mmol) and the mixture was heated at 50° C. for 16 hrs. The mixture was diluted with water (100 mL) and was extracted with ether (3×75 mL), the organic layer was dried (MgSO₄) and evaporated, give a mixture of bromoketones, which were dissolved in glyme (7.5 mL) and treated with sodium methoxide (43 mg, 3 eq). The mixture was stirred at room temperature for 2 hrs before quenching with acetic acid (0.5 mL), the mixture was diluted with water (30 mL) and extracted with ethyl acetate (3×25 mL). The organic layer was dried (MgSO₄) and evaporated, to give a mixture of esters. The 4-isomer was isolated by preparative t.l.c. ¹H NMR (CDCl₃) 7.38-7.32 (4H, m), 7.09-7.02 (2H, m), 6.89-6.83 (1H,m), 3.74 (3H, s), 2.62-2.53 (3H,m), 2.33-2.24 (4H, m) and 1.51-1.41 (2H, m); MS MH+ 469 (471).

Example 124

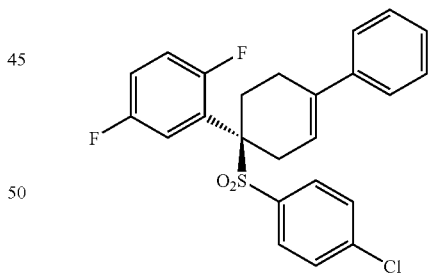

Step (1)

The ketone from Example 2 (5 g, 13 mmol) was dissolved in tetrahydrofuran (100 ml) and was added at −78° C. to a solution of LDA (28.6 mmol) in tetrahydrofuran (200 ml). The mixture was warmed to −30° C. over 1 hr and then recooled to −78° C. before treating with N-phenyl triflamide (4.65 g, 13 mmol) and the mixture was allowed to warm to rt over 16 hr. The mixture was diluted with water (2 ml) and the solution washed with ethyl acetate (2×500 ml). The organic phase washed with brine (500 ml), dried (MgSO₄) and evaporated. The clear oil obtained was purified by column chromatography on silica gel eluting with 5-20% ethyl acetate in hexanes. The oil obtained was then further purified by column chromatography on silica gel eluting with 5-10% ethyl acetate in hexane to give 4-(2,5-difluorophenyl)-4-(4-chlorophenylsulphonyl)-1-trifluoromethylsulphonylcyclohex-1-ene.

$^1$H NMR (CDCl$_3$) 7.42-7.36 (4H, m), 7.10-7.04 (2H, m), 6.91-6.83 (1H, m), 5.77-5.76 (1H, m), 3.14-3.12 (2H, m), 3.01-2.95 (1H, m), 2.57-2.44 (2H, m) and 2.24-2.14 (1H, m).

Step (2)

The triflate from step (1) (260 mg, 0.6 mmol), cesium carbonate (357 mg, 1.2 mmol) and phenyl boronic acid (94 mg, 0.76 mmol) were dissolved in dimethoxyethane/water [9:1] (20 ml). The flask was degassed and then tetrakistriphenylphosphine palladium (25 mg) was added, the mixture warmed to reflux over 4 hr and then cooled to rt. The solution was filtered through Celite™ and was diluted with water (20 ml) The solution washed with ethyl acetate (2×100 ml). The organic phase washed with brine (100 ml), dried (MgSO$_4$) and evaporated. The clear oil obtained was purified by column chromatography on silica gel eluting with 5% ethyl acetate in hexanes, to give the desired product. $^1$H NMR (CDCl$_3$) 7.44-7.38 (4H, m), 7.25-7.17 (5H, m), 7.13-7.07 (1H, m), 7.01-6.96 (2H, m), 6.86-6.79 (1H, m), 6.09-6.07 (1H, m), 3.16-3.14 (2H, m), 3.07-3.02 (1H, m), 2.73-2.67 (1H,m), 2.49-2.45 (1H, m) and 2.28-2.25 (1H, m).

Example 125

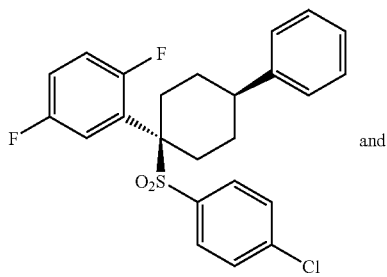

and

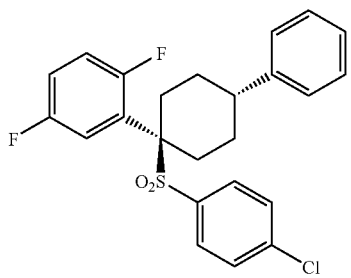

The alkene from Example 124 (60 mg, 0.13 mmol) was dissolved in ethanol (5 ml). The flask was degassed and then 5% palladium on carbon (5 mg) was added the mixture was stirred under an atmosphere of hydrogen for 45 mins. The solution was filtered through Celite™ and evaporated. The clear oil obtained was purified by preparative tlc eluting with 5% ethyl acetate in hexanes. The oil obtained was then further purified by column chromatography on silica gel eluting with 5% ethyl acetate in hexane to give the cis isomer; $^1$H NMR (CDCl$_3$) 7.38 (4H, s), 7.25-7.00 (7H, m), 6.91-6.84 (1H, m), 3.08-3.06 (1H, m), 2.75-2.69 (2H, m), 2.38-2.31 (2H, m), 2.04-2.00 (2H,m) and 1.44-1.38 (2H, m); and the trans isomer $^1$H NMR (CDCl$_3$) 7.42-7.37 (8H, m), 7.34-7.00 (3H, m), 6.91-6.83 (1H, m), 2.87-2.75 (3H, m), 2.49-2.40 (1H, m), 2.37-2.26 (2H, m) and 1.90-1.80 (1H, m).

Example 126

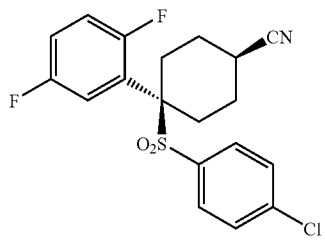

The trans mesylate from Example 37 (103 mg, 0.22 mmol) was dissolved in toluene (20 ml) and added to a pre-azeotroped sample of tetrabutylammonium cyanide (354 mg, 1.32 mmol), and the mixture was warmed to 70° C. over 18 hr and then cooled to rt. The solution was diluted with water (10 ml) and washed with ethyl acetate (2×50 ml). The organic phase washed with brine (10 ml), dried (MgSO$_4$) and evaporated. The clear oil obtained was purified by column chromatography on silica gel eluting with 10-20% ethyl acetate in hexanes, to give the cyanide. $^1$H NMR (CDCl$_3$) 7.42-7.36 (4H, s), 7.10-7.05 (2H, m), 6.89-6.84 (1H, m), 2.88-2.86 (1H, m), 2.76-2.72 (2H, m), 2.52-2.45 (1H,m), 2.12-2.07 (1H, m) and 1.56-1.49 (1H, m).

Example 127

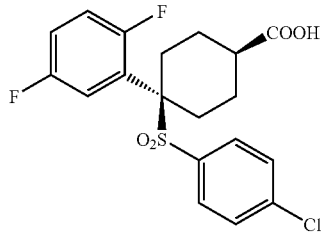

The cyanide from Example 126 (143 mg, 0.36 mmol) was dissolved/suspended in a mixture of glacial acetic acid (10 ml) and conc. HCl (6 ml) and heated at 110° C. for 15 hours. The mixture was cooled, diluted with ethyl acetate and washed with water (×3), dried (MgSO$_4$) and evaporated to dryness. This crude residue (153 mg) was purified by preparative tlc (5% methanol in dichloromethane/1% acetic acid). $^1$H NMR (CDCl$_3$) 7.38-7.35 (4H, s), 7.08-7.06 (2H, m), 6.90-6.84 (1H, m), 2.65-2.58 (2H, m), 2.38-2.33 (3H, m), and 1.75-1.49 (4H, m).

Example 128

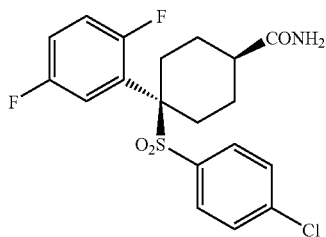

The cyanide from Example 126 (50 mg, 0.12 mmol) was dissolved in a mixture of tetrahydrofuran (4.5 ml) and water (0.5 ml) and stirred at 20° C. The mixture was treated with hydrogen peroxide (20 ml, 0.6 mmol) and then with lithium hydroxide (6 mg, 0.25 mmol) for 2 hours. Hydrogen peroxide (20 ml, 0.6 mmol) and then with lithium hydroxide (6 mg, 0.25 mmol) were added and the mixture was stirred at rt. for 72 hrs. The mixture was cooled, diluted with ethyl acetate and washed with water (×2) and sat. sodium bisulphite, dried (MgSO$_4$) and evaporated to dryness. This crude residue (51 mg) was purified by preparative tlc (20% ethyl acetate in hexanes) $^1$H NMR (CDCl$_3$) 7.37 (4H, s), 7.10-7.02 (2H, m), 6.90-6.84 (1H, m), 5.57 (2H, brs), 2.54-2.48 (3H, m), 2.43-2.39 (1H, m), 2.19-2.15 (2H, m) and 1.62-1.50 (3H, m).

Example 129

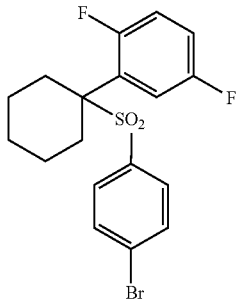

Step (1)

1-Trifluoromethylsulphonylcyclohex-1-ene (3 g, 13 mmol), cesium carbonate (8.4 g, 26 mmol) and 2,5-difluorophenyl boronic acid (2.88 g, 18 mmol) were dissolved in dimethoxyethane/water [9:1] (200 ml). The flask was degassed and then tetrakistriphenylphosphine palladium (125 mg) was added, the mixture warmed to 80° C. over 4 hr and then cooled to r.t. The solution was filtered through Celite™, diluted with water (20 ml) and the solution washed with ethyl acetate (2×100 ml). The organic phase washed with brine (100 ml), dried (MgSO$_4$) and evaporated. The clear oil obtained was purified by column chromatography on silica gel eluting with hexanes, to give 1-(2,5-difluorophenyl)cyclohex-1-ene. $^1$H NMR (CDCl$_3$) 6.97-6.73 (3H, m), 5.97-5.96 (1H, m), 2.35-2.31 (2H, m), 2.23-2.14 (2H, m) and 1.79-1.68 (1H, m).

Step (2)

The styrene from Step (1) (100 mg, 0.5 mmol) and 4-bromothiophenol (96 mg 0.5 mmol) were dissolved in dichloromethane (5 ml) and then 70% aqueous perchloric acid (15 ml) was added. The mixture was stirred at rt. over 24 hr and then treated with m-chloroperoxybenzoic acid in dichloromethane (10 ml) with stirring at rt. for a further 6 hrs. The mixture was diluted with 2N sodium hydroxide (2 ml) and separated on a Varian Bond Elut™ cartridge. The organic phase was dried (MgSO$_4$) and evaporated. The clear oil obtained was purified by column chromatography on silica gel eluting with 2-5% ethyl acetate in hexanes, to give the sulphone. $^1$H NMR (CDCl$_3$) 7.53 (2H, d, J=8.6 Hz), 7.27 (2H, d, J=8.6 Hz), 7.08-7.03 (2H, m), 6.84-6.80 (1H, m), 2.82-2.63 (2H, m), 2.12-2.04 (2H, m), 1.82-1.78 (2H, m) 1.64-1.54 (1H, m) and 1.40-1.18 (3H, m).

Following the procedure of Example 129, using the appropriate thiophenol in Step (2), the compounds of Examples 130-132 were obtained:

Example 130

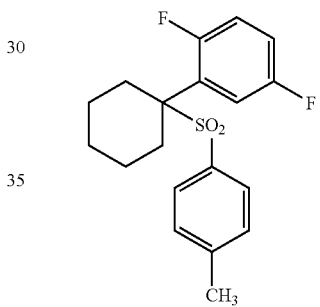

$^1$H NMR (CDCl$_3$) 7.30 (2H, d, J=8.6 Hz), 7.18 (2H, d, J=8.6 Hz), 7.03-6.97 (2H, m), 6.85-6.79 (1H, m), 2.85-2.65 (2H, m), 2.41 (3H, s), 2.10-2.03 (2H, m), 1.81-1.75 (2H, m) 1.61-1.57 (1H, m) and 1.35-1.13 (3H, m).

Example 131

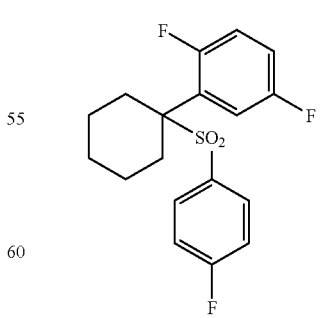

$^1$H NMR (CDCl$_3$) 7.44-7.40 (1H, m), 7.10-7.00 (4H, m), 6.86-6.80 (1H, m), 2.82-2.61 (2H, m), 2.12-2.07 (2H, m), 1.82-1.78 (2H, m) 1.62-1.54 (1H, m) and 1.45-1.15 (3H, m).

Example 132

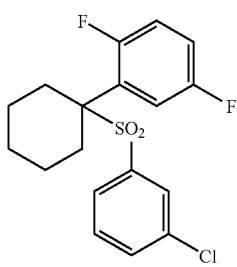

$^1$H NMR (CDCl$_3$) 7.58-7.54 (1H, m), 7.34-7.33 (3H,m), 7.10-7.03 (2H, m), 6.98-6.81 (1H, m), 2.82-2.61 (2H, m), 2.18-2.07 (2H, m), 1.85-1.79 (2H, m) 1.63-1.58 (1H, m) and 1.40-1.17 (3H, m).

Example 133

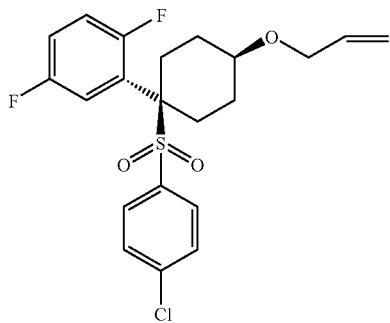

To the cis alcohol from Example 22 (1.8 g, 4.7 mmol) in dry THF (10 ml) under nitrogen were added sodium hydride (60% dispersion, 740 mg, 18.6 mmol) and potassium $^t$butoxide (1M in THF solution, 0.47 ml, 0.47 mmol). Allyl bromide (1.2 ml, 14.1 mmol) was added and the reaction heated at 60° C. for 18 h., diluted with water and extracted with ethyl acetate (×3). Organic extracts were washed with brine, dried (MgSO$_4$), filtered and evaporated. Crude product purified by flash column chromatography (2:1 $^t$hexane/ethyl acetate) to give a light yellow semi-solid (1.0 g). $^1$H NMR (CDCl$_3$) 1.24-1.32 (2H, m), 1.97 (1H, s), 2.03 (1H, d, J=9.5 Hz), 2.51 (4H, d, J=11.2 Hz), 3.47 (1H, t, J=2.8 Hz), 3.94 (1H, t, J=1.6 Hz), 3.96 (1H, t, J=1.4 Hz), 5.17-5.27 (2H, m), 5.86-5.96 (1H, m), 6.83-6.90 (1H, m), 7.02-7.14 (2H, m), 7.38 (4H, s).

Example 134

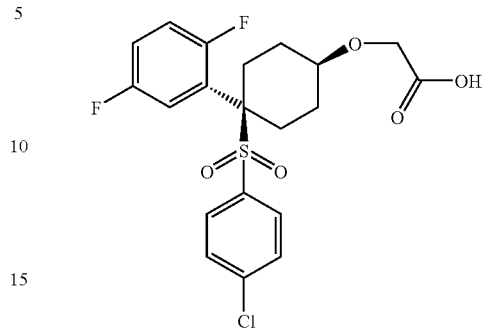

The allyl ether (200 mg, 0.47 mmol) from example 133 was dissolved in carbon tetrachloride (10 ml), water (1 ml), and acetonitrile (1 ml). The solution was stirred vigorously and sodium metaperiodate (402 mg, 1.88 mmol) and ruthenium trichloride hydrate (2 mg) were added. After 2 h the reaction was diluted with DCM and filtered through Celite™. The filtrate was concentrated and partitioned between ethyl acetate and water. Organic extracts were washed with brine, dried (MgSO$_4$), filtered and evaporated. Crude product purified by flash column chromatography (ethyl acetate) to give a white solid (80 mg). $^1$H NMR (CDCl$_3$) 2.04 (5H, br), 2.30-2.59 (4H, m), 3.63-3.67 (1H, br), 4.05 (2H, br), 6.79 (1H, br), 6.99 (2H, br), 7.29 (4H, br).

Example 135

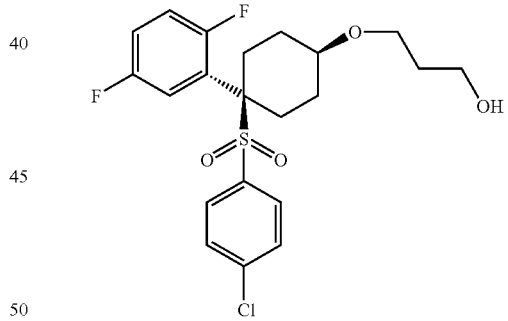

The allyl ether (120 mg, 0.28 mmol) from Example 133 was dissolved in dry THF (5 ml). To the solution under nitrogen and cooled to 0° C. was added a borane-THF solution (1M, 0.56 ml, 0.56 mmol), via a syringe, over 5 minutes. The reaction was stirred at this temperature for 4 h and then water (0.5 ml) was added followed by aq. sodium hydroxide (2M, 0.5 ml) and 30% hydrogen peroxide (0.4 ml). Reaction was stirred for 15 h at room temperature, concentrated, and partitioned between ethyl acetate and water. Organic extracts were washed with brine, dried (MgSO$_4$), filtered and evaporated. Crude product purified by flash column chromatography (1:1 $^t$hexane/ethyl acetate) to give a colourless oil (80 mg). $^1$H NMR (CDCl$_3$) 1.81-1.88 (2H, m), 1.98 (1H, s), 2.03 (2H, d, J=8.4 Hz), 2.07 (1H, s), 2.46 (5H, dd, J=0.7, 0.7 Hz), 3.44 (1H, t, J=2.8 Hz), 3.57 (2H, t, J=5.8 Hz), 3.78 (2H, s), 6.83-6.90 (1H, m), 7.02-7.13 (2H, m), 7.38 (4H, s).

Example 136

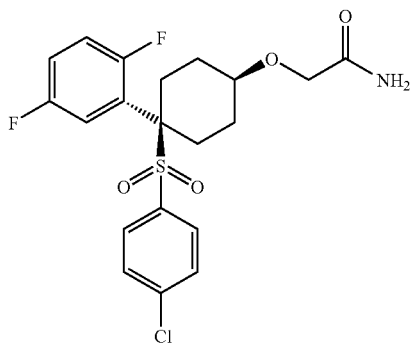

Step (1)

The acid from Example 134 (560 mg, 1.2 mmol) was dissolved in ethyl acetate (100 ml) under nitrogen and pentafluorophenol (330 mg, 1.8 mmol) was added. The solution was cooled to 0° C., dicyclohexylcarbodiimide (370 mg, 1.8 mmol) added, and the reaction was allowed to warm to room temperature and stirred for 1 h. The reaction mixture was filtered through a pad of Celite™, the filtrate evaporated and purified by flash chromatography (2:1 $^i$hexane/ethyl acetate) to give the pentafluorophenol ester as a white solid (760 mg).

Step (2)

To this ester (115 mg, 0.18 mmol) was added a 2 M solution of ammonia in methanol (3 ml), and the mixture heated at 50° C. in a sealed tube for 3 h. The reaction mixture was concentrated and purified by flash chromatography (1:1 $^i$hexane/ethyl acetate to 9:1 ethyl acetate/methanol) to give a white solid (54 mg). $^1$H NMR (CDCl3) 1.32-1.40 (2H, m), 2.04 (2H, br), 2.51-2.54 (4H, m), 3.54 (1H, t, J=2.8 Hz), 3.95 (2H, s), 5.45-5.54 (1H, br), 6.50-6.59 (1H, br), 6.83-6.90 (1H, m), 7.03-7.14 (2H, m), 7.36-7.40 (4H, m)

Example 137

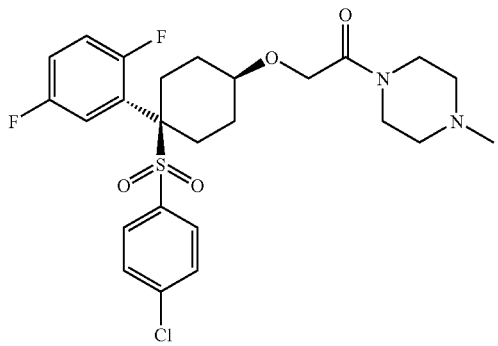

To the pentafluorophenol ester prepared in Example 136 (125 mg, 0.2 mmol) dissolved in DCM (3 ml) and under nitrogen was added N-methyl piperazine (70 μl, 0.8 mmol). After 1 h the reaction was concentrated, diluted with ethyl acetate, washed with aq. sodium carbonate, water, brine, dried (MgSO$_4$), filtered and evaporated. Purified by flash column chromatography (1:1 $^i$hexane/ethyl acetate to 9:1 ethyl acetate/methanol+2% triethylamine) to give a colourless glassy solid (50 mg). $^1$H NMR (CDCl$_3$) 1.34 (2H, m), 2.02 (4H, m), 2.34 (2H, m), 2.40-2.55 (8H, m), 3.55 (1H, t, J=2.8 Hz), 3.63 (2H, t, J=4.9 Hz), 4.14 (3H, s), 6.82-6.89 (1H, m), 7.02-7.12 (2H, m), 7.36 (4H, d, J=4.6 Hz).

Example 138

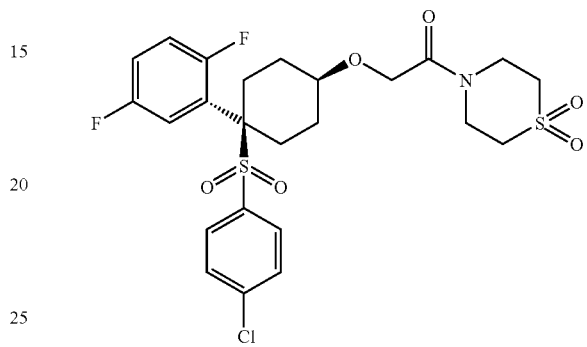

Prepared as in Example 137, using thiomorpholine sulfone hydrochloride (120 mg, 0.7 mmol) and triethylamine (0.1 ml) in place of N-methylpiperazine, to give a white solid (50 mg). $^1$H NMR (CDCl$_3$) 1.31-1.39 (2H, m), 2.00 (1H, s), 2.05 (1H, s), 2.38-2.45 (3H, m), 2.51-2.65 (1H, m), 3.09 (2H, d, J=1.1 Hz), 3.22 (2H, s), 3.58 (1H, t, J=2.5 Hz), 4.13 (4H, d, J=3.2 Hz), 4.18 (2H, s), 6.82-6.89 (1H, m), 7.03-7.12 (2H, m), 7.34 (3H, d, J=14.7 Hz), 7.39 (1H, s).

Example 139

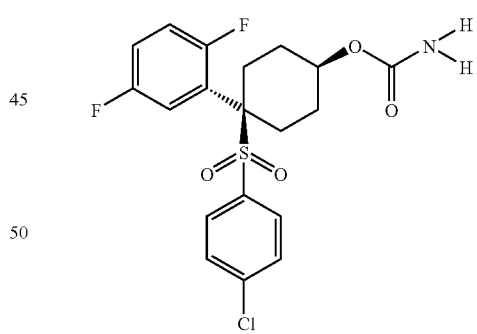

To the alcohol prepared in Example 22b (150 mg, 0.39 mmol) in dry THF (5 ml) cooled to 0° C. and under nitrogen was added chlorosulfonyl isocyanate (50 μl, 0.54 mmol). The reaction was stirred for 1 h and then sodium metabisulfite (220 mg, 1.17 mmol) in water (2 ml) was added dropwise over 5 min. Reaction was allowed to warm to room temperature and stirred for 16 h., diluted with water and extracted with ethyl acetate (×3). Organic extracts were washed with brine, dried (MgSO$_4$), filtered and evaporated. The carbamate was isolated by trituration with ether to give a white solid (40 mg). MS (EI+) 427 (M−2H)

Example 140

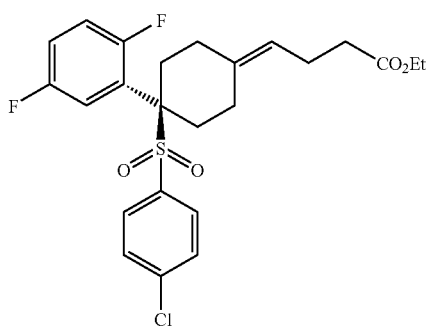

To 3-(ethoxycarbonyl)propyltriphenylphosphonium bromide (238 mg, 0.52 mmol) in dry toluene (5 ml) and under nitrogen was added dropwise potassium hexamethyldisilazide (0.5 M in toluene, 1.2 ml). The ketone from Example 2 (100 mg, 0.26 mmol) in dry toluene (3 ml) was added, the reaction stirred at 100° C. for 5 h., cooled, diluted with water and the organic layer removed. The aqueous layer was extracted with ethyl acetate (×3). Organic extracts were washed with brine, dried (MgSO$_4$), filtered and evaporated. Crude product purified by flash column chromatography (2:1 $^i$hexane/ethyl acetate) to give a white foam (70 mg). $^1$H NMR (CDCl$_3$) 1.24 (3H, t, J=7.2 Hz), 1.64-1.71 (2H, m), 1.93-2.38 (5H, m) 2.70-2.80 (4H, m), 4.13 (2H, q, J=7.1 Hz), 5.12 (1H, s), 6.83-6.91 (1H, m), 7.02-7.16 (3H, m), 7.37 (4H, s).

Example 141

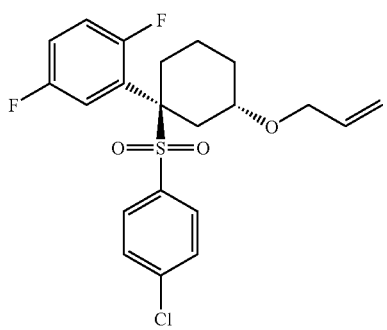

The trans-3-alcohol from Example 99 (40.0 mg, 0.104 mmol) in N,N-dimethylformamide (2 ml) was treated with allyl bromide (26.4 µl, 0.312 mmol), followed by sodium hydride (6.2 mg, 60% w/w in mineral oil, 0.156 mmol) and stirred at room temperature. After 2 hours, further portions of allyl bromide (26.4 µl, 0.312 mmol) and sodium hydride (6.2 mg, 60% w/w in mineral oil, 0.156 mmol) were added and stirring at room temperature continued. After 4 hours, reaction was quenched with water (60 ml), extracted with ethyl acetate (3×40 ml). Combined organics were washed with brine (sat., 150 ml), dried (MgSO$_4$) and concentrated in vacuo to give crude product (45 mg). This material was purified by preparative t.l.c., eluting with 15% ethyl acetate in hexanes to give product (25 mg, 56%). $^1$H NMR (400 MHz, CDCl$_3$) 1.53-1.81 (3H, m), 2.29-2.35 (1H, m), 2.45 (2H, d, J=13.8 Hz) 2.95-3.00 (1H, br), 3.80-3.82 (2H, m), 3.91-3.92 (2H, m), 4.89-4.98 (2H, m), 5.58-5.68 (1H, m), 6.74-6.80 (1H, m), 6.93-7.02 (2H, m), 7.29-7.38 (4H, m).

Example 142

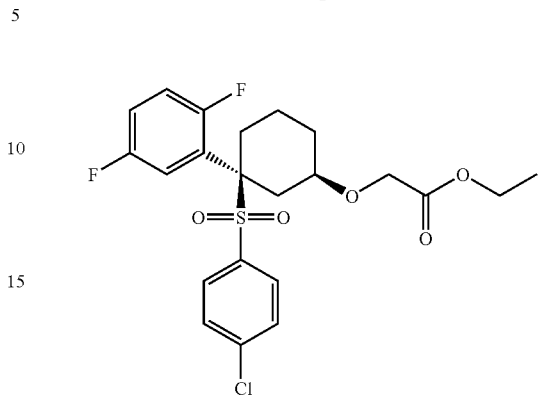

The cis-3-alcohol from Example 93 (87.0 mg, 0.226 mmol) in N,N-dimethylformamide (3 ml) was dripped into a suspension of sodium hydride (27.1 mg, 60% w/w in mineral oil, 0.678 mmol) in N,N-dimethylformamide (1 ml). Ethyl bromoacetate (75.2 µl, 0.678 mmol) was added and reaction stirred at room temperature. After 2 hours a further portion of ethyl bromoacetate (75.2 µl, 0.678 mmol) was added, the mixture stirred at room temperature for a further 4 hours, then heated to 90° C. for 3.5 hours. Reaction was then cooled, further portions of sodium hydride (27.1 mg, 60% w/w in mineral oil, 0.678 mmol) and ethyl bromoacetate (75.2 µl, 0.678 mmol) added, and heated again to 90° C. After 4 hours at this temperature, reaction was cooled, diluted with water (150 ml) and extracted with ethyl acetate (3×100 ml). Combined organics were washed with brine (sat., 250 ml), dried (MgSO$_4$) and evaporated in vacuo to give crude (263 mg). Crude material was chromatographed on silica, eluting with 15% ethyl acetate in hexanes to give impure product (32 mg) which was purified further by preparative t.l.c., eluting with 15% ethyl acetate in hexanes, followed by a second preparative t.l.c., eluting with 100% dichloromethane to give product (7 mg, 7%). $^1$H NMR (400 MHz, CDCl$_3$), 1.22-1.38 (3H, m), 1.89-1.94 (1H, m), 2.00-2.05 (3H, br), 2.60-3.15 (2H, m), 3.19-3.26 (1H, m), 4.07 (2H, s), 4.16-4.26 (4H, m), 6.84-6.95 (1H, m), 7.02-7.11 (2H, m), 7.39 (4H, s).

Example 143

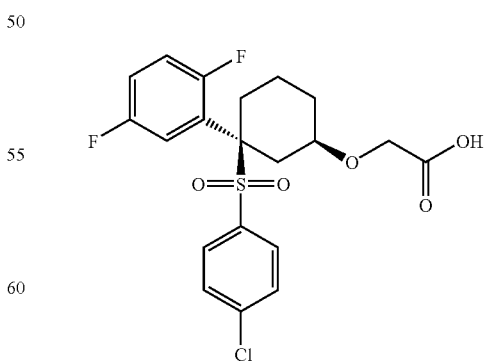

The cis-allyl ether from Example 101 (50.0 mg, 0.108 mmol) in carbon tetrachloride (0.2 ml), water (0.3 ml) and acetonitrile (0.2 ml) was treated with sodium (meta)periodate (95.0 mg, 0.444 mmol) followed by ruthenium(III) chloride hydrate (2.2 mol %, 0.5 mg, 2.38 nmol). After stirring at room temperature for 2 hours, dichloromethane (2 ml) was added and the phases separated. Aqueous phase was extracted with dichloromethane (3×5 ml). Combined organics were dried (MgSO$_4$) and evaporated in vacuo to give a brown residue (44 mg). This residue was diluted in diethyl ether (10 ml) and filtered through a pad of Celite™, then concentrated in vacuo to give crude (34 mg). This material was purified by preparative t.l.c., eluting with 5% methanol, 1% acetic acid in dichloromethane to give product (27 mg, 56%). $^1$H NMR (400 MHz, (CD$_3$)$_2$SO), 0.99-1.23 (2H, br), 1.70-1.86 (2H, br), 1.87-1.99 (1H, br), 2.55-3.05 (2H, br), 3.09-3.22 (1H, br), 3.24-3.40 (2H, br), 3.85-4.05 (1H, br), 7.10-7.20 (2H, br), 7.25-7.35 (1H, br), 7.41 (2H, d, J=7.9 Hz), 7.64 (2H, d, J=8.0 Hz), 12.10-12.80 (1H, br).

Example 144

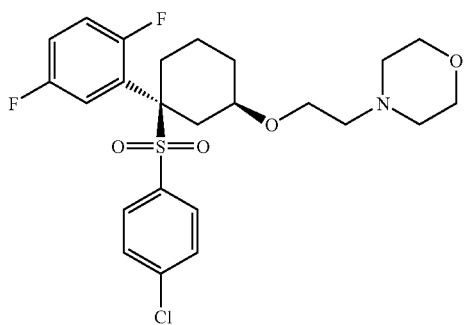

The cis-allyl ether from Example 101 (100 mg, 0.235 mmol) in dichloromethane/methanol (1:1, 10 ml) was cooled to −78° C. The flask was purged with oxygen, then with ozone until saturated, then with oxygen again and finally nitrogen. The mixture was warmed to room temperature and dimethyl sulphide (159 µl, 2.35 mmol) added. The reaction was then allowed to warm to room temperature and stirring continued for a further 16 hours. Solvent was removed in vacuo and the residue partitioned between water (10 ml) and ethyl acetate (10 ml). The aqueous phase was separated and extracted with ethyl acetate (2×10 ml). Combined organics were washed with brine (sat., 40 ml), dried (MgSO$_4$) and evaporated in vacuo to give the cyclohexyloxyacetaldehyde derivative (102 mg, >99%). $^1$H NMR (400 MHz, CDCl$_3$), 1.16-1.25 (1H, br), 1.32-1.40 (1H, br), 1.90-1.96 (2H, m), 2.02-2.10 (2H, br), 2.30-3.00 (2H, br), 3.18-3.23 (1H, m), 4.09 (2H, s), 6.84-6.91 (1H, m), 7.03-7.09 (2H, m), 7.36-7.41 (4H, m), 9.68 (1H, s).

The aldehyde (102 mg, 0.238 mmol) in dichloroethane (10 ml) was then treated with morpholine (22.9 µl, 0.262 mmol). After stirring at room temperature for 2 hours, the mixture was treated with sodium triacetoxyborohydride (202 mg, 0.852 mmol) and glacial acetic acid (1 ml). After a further 1.5 hours at room temperature, solvent was removed in vacuo and the residue partitioned between dichloromethane (5 ml) and sodium hydrogen carbonate (sat. aq., 5 ml). The organic phase was separated on a Varian Bond Elut™ cartridge and purified on a SCX Varian Bond Elut™ cartridge. Solvent was removed in vacuo to give product (80 mg, 67%). $^1$H NMR (400 MHz, CDCl$_3$), 1.15-1.32 (2H, m), 1.87-1.99 (4H, m), 2.47-2.49 (4H, m), 2.54 (2H, t, J=6.0 Hz), 2.60-3.00 (2H, br), 3.08-3.16 (1H, br), 3.56-3.63 (2H, m), 3.70 (4H, t, J=4.6 Hz), 6.84-6.90 (1H, m), 7.03-7.08 (2H, m), 7.36-7.41 (4H, m); ms. (ES$^+$), 500 (M$^+$+1), 324 (M$^+$175), 193 (M$^+$306).

Example 145

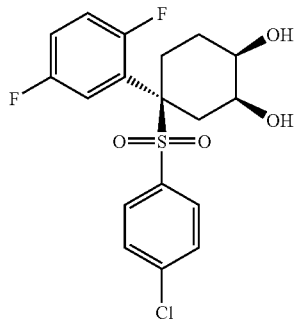

The cyclohexene from Example 34 (493 mg, 1.34 mmol) and N-methylmorpholine-N-oxide (204 mg, 1.74 mmol) in tetrahydrofuran/water (3:1, 8 ml) were stirred during the addition of osmium tetroxide (107 µl, 2.5 wt. % in $^t$BuOH, 0.342 mmol). Mixture was stirred for 24 hours at room temperature, then another portion of osmium tetroxide (107 µl, 2.5 wt. % in $^t$BuOH, 0.342 mmol) was added and stirring continued for a further 5 hours. The reaction mixture was diluted with sodium hydrogen sulfite (sat., aq., 15 ml) then extracted with ethyl acetate (3×15 ml). Combined organics were washed with brine (sat., 50 ml), dried (MgSO$_4$) and evaporated in vacuo to give product (88:12 cis:trans) (509 mg, 94%). $^1$H NMR (400 MHz, CD$_3$OD), 1.31-1.39 (1H, m), 1.92 (1H, qd, J=14.6 Hz and J=3.1 Hz), 2.40-2.62 (4H, br), 3.33-3.38 (1H, m), 3.78 (1H, d, J=2.7 Hz), 6.97-7.10 (1H, m), 7.16-7.21 (2H, m), 7.43 (2H, d, J=8.5 Hz), 7.52 (2H, d, J=8.6 Hz).

Example 146

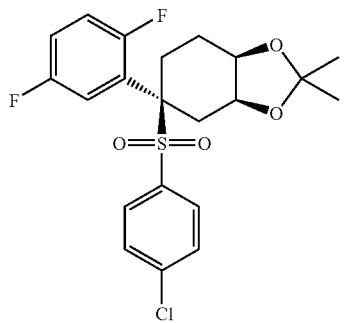

The mixture of diols from Example 145 (100 mg, 0.249 mmol) in acetone (3 ml) was treated with para-toluenesulphonic acid monohydrate (30.0 mg, 0.158 mmol) and the mixture stirred at room temperature. After 4 hours, a further portion of para-toluenesulphonic acid monohydrate (50.0 mg, 0.263 mmol) was added and the reaction mixture heated to 60° C. for 1 hour, then stirring continued at room temperature for a further 24 hours. Solvent was then removed in vacuo and the residue partitioned between ethyl acetate (10 ml) and sodium hydrogen carbonate (sat. aq., 10 ml). The aqueous phase was separated and extracted with ethyl acetate (2×10 ml). Combined organics were then washed with brine (sat., 50 ml), dried (MgSO4) and evaporated in vacuo to give crude (77 mg). This material was chromatographed on silica, eluting with 20% ethyl acetate in hexanes, followed by further purification by preparative t.l.c., eluting with 30% ethyl acetate in hexanes to give product (7.7 mg, 7%). $^1$H NMR (400 MHz, CDCl$_3$), 1.31 (3H, s), 1.54 (3H, s), 1.59-1.66 (1H, m), 2.14-2.20 (1H, m), 2.26-2.32 (1H, m), 2.35-2.42 (1H, m), 2.54-2.58 (1H, br), 2.81-2.86 (1H, br), 3.95-4.03 (2H, m), 6.83-6.89 (1H, m), 7.03-7.11 (2H, m), 7.36-7.41 (4H, m).

Example 147

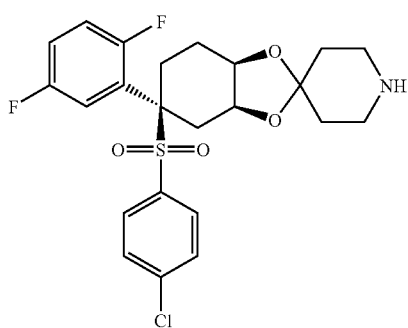

The mixture of diols from Example 145 (100 mg, 0.249 mmol) in toluene (3 ml) was treated with N-Fmoc-4-piperidone (240 mg, 0.747 mmol) and para-toluenesulphonic acid monohydrate (10 mg). This mixture was heated to reflux under Dean-Stark conditions. After 3 hours, solvent was removed in vacuo to give crude (420 mg). This material was chromatographed on silica, eluting with 25% ethyl acetate in hexanes to give protected acetal (148 mg, 84%).

This material was treated with 20% diethylamine in dichloromethane (5 ml). After stirring at room temperature for 16 hours, solvent was removed in vacuo to give crude (343 mg). This material was chromatographed on silica, eluting with dichloromethane/methanol/ammonia (90:8:1) to give material which was purified further by preparative t.l.c., eluting with dichloromethane/methanol/ammonia (90:8:1) giving product (40 mg, 39%). $^1$H NMR (360 MHz, CDCl$_3$), 1.58-1.70 (3H, br), 1.83-1.88 (2H, m), 2.17 (1H, dt, J=10.2 Hz and J=2.0 Hz), 2.31-2.58 (3H, br), 2.84-3.02 (3H, m), 3.00 (2H, t, J=5.7 Hz), 3.97-4.03 (2H, m), 6.81-6.88 (1H, m), 7.02-7.11 (2H, m), 7.34-7.40 (4H, m).

Example 148

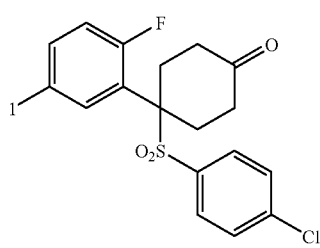

Prepared by the methods of Examples 1 and 2. The sulphone used for the process of Example 1 was obtained in the same manner as Intermediate 1, using 2-fluoro-5-iodobenzyl bromide in place of 2,5-difluorobenzyl bromide. $^1$H NMR (360 MHz, CDCl$_3$) 2.18 (2H, dt, J=5.5, 16.4 Hz), 2.52-2.59 (4H, m), 2.97-3.06 (2H, m), 6.76 (1H, dd, J=8.6, 12.7 Hz), 7.36-7.44 (4H, m), 7.56 (1H, dd, J=2.1, 7.5 Hz), 7.69-7.73 (1H, m).

Example 149

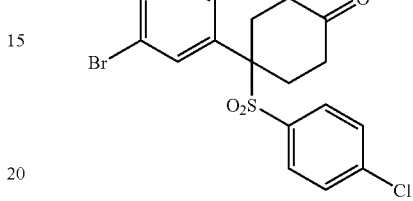

Prepared by the methods of Examples 1 and 2. The sulphone used for the process of Example 1 was obtained in the same manner as Intermediate 1, using 2-fluoro-5-bromobenzyl bromide in place of 2,5-difluorobenzyl bromide. $^1$H NMR (360 MHz, CDCl$_3$) 2.19 (2H, dt, J=5.2, 16.3 Hz), 2.53-2.59 (4H, m), 2.98-3.06 (2H, m), 6.88 (1H, dd, J=8.7, 12.5 Hz), 7.37-7.55 (6H, m).

Example 150

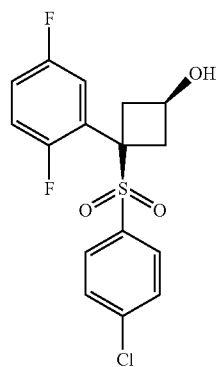

A solution of Intermediate 1 (10 g) in THF (100 ml) was cooled to −30° C. and treated slowly with n-BuLi (1.6 M in hexane, 22 ml). The reaction was stirred for 30 mins, then treated with epichlorohydrin, warmed to room temperature and refluxed for 30 min. The reaction mixture was cooled, evaporated and partitioned between water/EtOAc. The aqueous layer was dried, filtered and evaporated. Purification by column chromatography gave the alcohol (5 g, 42%) as a white solid. $^1$H NMR (360 MHz, CDCl$_3$) 7.41-7.35 (4H, m), 7.04-6.97 (1H, m), 6.85-6.76 (2H, m), 4.34-4.24 (1H, m), 3.59 (1H, d, J=10.7 Hz), 3.13-3.11 (4H, m).

Example 151

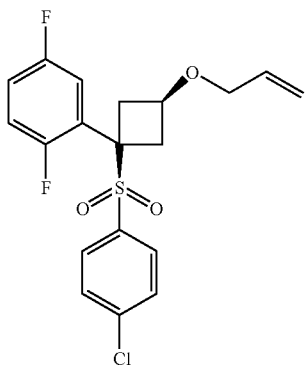

A solution of the alcohol from Example 150 (3 g) in DMF (20 ml) was treated with sodium hydride (1.5 equiv.) and allyl bromide (2 equiv.) and stirred at room temperature for 1 h. The reaction mixture was diluted with 1N HCl and ethyl acetate. The organic phase washed, dried, filtered and evaporated. Purification by column chromatography gave the allyl ether (3 g, 89%) as a white solid. $^1$H NMR (400 MHz, CDCl$_3$) 7.39-7.34 (4H, m), 7.04-6.99 (1H, m), 6.95-6.91 (1H, m), 6.85-6.79 (1H, m), 5.94-5.85 (1H, m), 5.29-5.17 (2H, m), 3.94-3.84 (3H, m), 3.23-3.18 (2H, m), 3.00-2.95 (2H, m).

Example 152

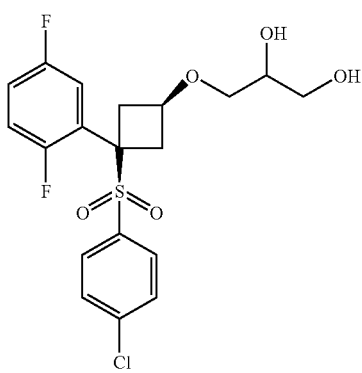

A solution of the allyl ether from Example 151 (2 g) was dissolved in $^t$BuOH (20 ml), THF (20 ml) and water (1 ml) and treated with N-methylmorpholine-N-oxide (3 equiv.) and OsO$_4$ (2.5 wt % solution in $^t$BuOH, 2 ml) and stirred at room temperature for 1 h. The reaction mixture was treated with sodium sulfite (3 equiv.), stirred for 10 min, then diluted with water/EtOAc. The organic phase was dried, filtered and evaporated. Purification by column chromatography gave the diol (2.1 g, 97%) as a white solid. $^1$H NMR (360 MHz, CDCl$_3$) 7.37 (4H, s), 7.05-6.98 (1H, m), 6.93-6.88 (1H, m), 6.83-6.77 (1H, m), 3.99-3.87 (2H, m), 3.79-3.64 (2H, m), 3.53-3.44 (2H, m), 3.25-3.19 (2H, m), 3.03-2.97 (2H, m), 2.83 (1H, d, J=4.8 Hz), 2.09 (1H, t, J=6.1 Hz).

Example 153

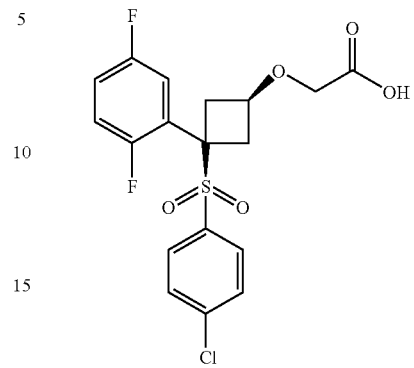

A solution of the diol from Example 152 (2 g) was dissolved in methanol (20 ml) and water (20 ml) and treated with sodium periodate (3 equiv.) and stirred at room temperature for 10 min. The reaction mixture was diluted with ether and water. The organic layer washed, dried, filtered and evaporated in vacuo to give the corresponding aldehyde. This compound was dissolved in $^t$BuOH (20 ml) and water (6 ml) and treated with NaClO$_2$ (3 equiv.) and NaH$_2$PO$_4$.2H$_2$O (1.05 equiv.) and stirred at room temperature for 1 h. The reaction mixture was quenched with 1N HCl, ethyl acetate and water. The organic phase washed, dried, filtered and evaporated. Purification by column chromatography gave the acid as a white solid (1.2 g, 81%). $^1$H NMR (360 MHz, DMSO) 12.8 (1H, brs), 7.62-7.60 (2H, m), 7.43-7.39 (2H, m), 7.32-7.03 (3H, m), 3.99 (2H, s), 3.92 (1H, qt, J=7.4 Hz), 3.07-2.96 (4H, m).

Example 154

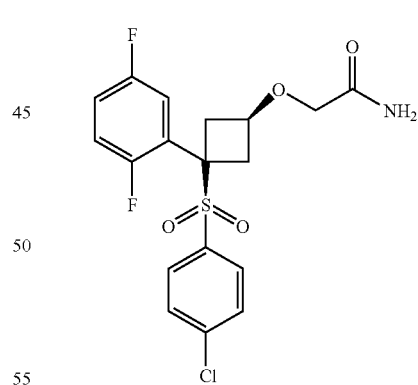

A solution of the acid from Example 153 (0.8 g) was dissolved in ethyl acetate (10 ml) and treated with C$_6$F$_5$OH (1.5 equiv.) and DCC (1.5 equiv.) and stirred at room temperature for 15 min. The reaction mixture was filtered and evaporated in vacuo and used without further purification.

A solution of the resulting active ester (ca. 0.64 mmol) in DCM (3.33 ml) was treated with ammonia gas and stirred at room temperature for 10 min. The reaction mixture was evaporated in vacuo and purified by column chromatography to give the amide (120 mg, 45%) as a white solid. $^1$H NMR (400 MHz, DMSO) 7.61 (2H, d, J=8.7 Hz), 7.41 (2H, d, J=8.7 Hz), 7.30-6.99 (5H, m), 3.95-3.88 (1H, m), 3.76 (2H, s), 3.09-2.93 (4H, m).

Example 155

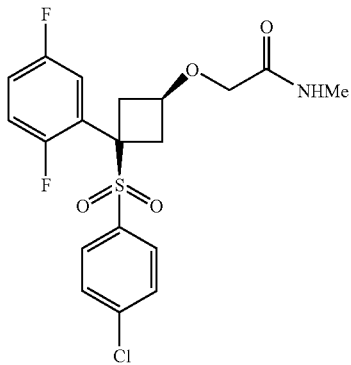

Prepared in 47% yield by a procedure analogous to Example 154. ¹H NMR (400 MHz, DMSO) 7.70 (1H, brd), 7.63-7.61 (2H, m), 7.41-7.40 (2H, m), 7.32-7.27 (1H, m), 7.17-7.09 (1H, m), 7.07-7.02 (1H, m), 3.95-3.85 (1H, m), 3.80 (2H, s), 3.04-3.01 (4H, m), 2.61 (3H, d, J=4.8 Hz).

Example 156

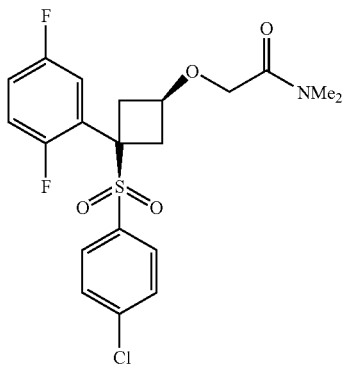

Prepared in 35% yield in a procedure analogous to Example 154. ¹H NMR (400 MHz, DMSO) 7.63-7.61 (2H, m), 7.42-7.40 (2H, m), 7.33-7.25 (1H, m), 7.17-7.01 (2H, m), 4.10 (2H, s), 3.95-3.85 (1H, m), 3.08-2.94 (4H, m), 2.88 (3H, s), 2.79 (3H, s).

Example 157

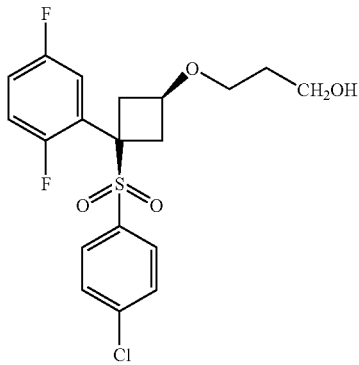

A solution of the allyl ether from Example 151 (0.6 g) in THF (15 ml) was cooled to −10° C. and treated with a solution of borane in THF (1.0M, 1.5 equiv.) The reaction mixture was stirred at room temperature for 1 h, then re-cooled to −10° C. and treated with 4N NaOH and $H_2O_2$. The reaction mixture was warmed to room temperature, washed with brine, dried, filtered and evaporated. Purification by column chromatography gave the alcohol (350 mg, 56%) as a white solid. ¹H NMR (360 MHz, CDCl₃) 7.37 (4H, s), 7.05-6.98 (1H, m), 6.94-6.89 (1H, m), 6.85-6.78 (1H, m), 3.91-3.78 (3H, m), 3.54 (2H, t, J=5.8 Hz), 3.22-3.17 (2H, m), 2.99-2.96 (2H, m), 2.01 (1H, brs), 1.84 (2H, qt, J=5.8 Hz).

Example 158

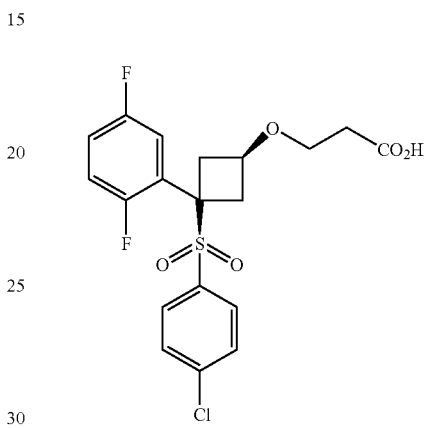

A solution of the alcohol from Example 157 (330 mg) was dissolved in $CCl_4$ (2 ml), MeCN (2 ml), water (3 ml) and treated with $RuO_2.H_2O$ (5 mg) and sodium periodate (800 mg) and stirred vigorously for 1 h. The reaction mixture was diluted with DCM, and the organic layer was dried, filtered and evaporated. Purification by column chromatography gave the acid as a solid (100 mg, 29%). ¹H NMR (400 MHz, CDCl₃) 7.37 (4H, s), 7.04-6.99 (1H, m), 6.94-6.90 (1H, m), 6.84-6.78 (1H, m), 3.89 (1H, qt, J=7.4 Hz), 3.67-3.64 (2H, m), 3.23-3.18 (2H, m), 3.01-2.96 (2H, m), 2.66-2.63 (2H, m).

Example 159

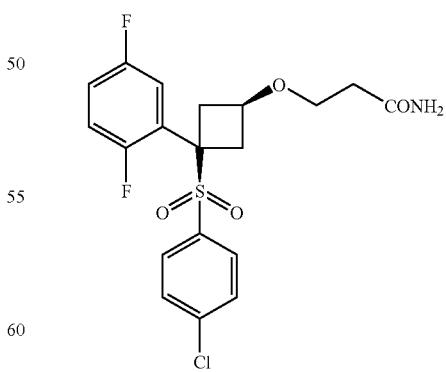

A solution of the acid from Example 158 was converted into the corresponding amide in 81% yield using the conditions described in Example 154. ¹H NMR (360 MHz, CDCl₃) 7.38 (4H, s), 7.05-6.99 (1H, m), 6.93-6.88 (1H, m), 6.84-6.77

(1H, m), 6.42 (1H, brs), 5.39 (1H, brs), 3.95 (1H, qt, J=7.4 Hz), 3.65-3.62 (2H, m), 3.27-3.20 (2H, m), 3.05-2.99 (2H, m), 2.54 (2H, t, J=5.6 Hz).

Examples 160-177

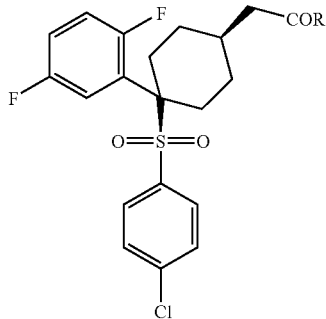

These Examples were prepared by the following method, using the appropriate amine free base or amine salt with prior neutralization.

To a stirred suspension of cis 4-(4-chlorobenzenesulphonyl)-4-(2,5-difluorophenyl)cyclohexaneacetic acid (Example 50, 0.15 g, 0.35 mmol) in dichloromethane (5 ml) was added oxalyl chloride (0.05 ml, 0.57 mmol) and dimethylformamide (1 drop). After 30 minutes the solution was evaporated to a small volume and to a solution of the residue in dichloromethane (5 ml) was added the desired amine (1.75 mmol). After stirring the solution for 20 minutes the solvent was removed in vacuo and the residue purified by chromatography on silica gel eluting with increasing concentrations of ethyl acetate in isohexane (25%, 50%). The fractions containing the product were evaporated to give the product amide. Chromatographic purification was performed on silica gel using appropriate concentrations of ethyl acetate in isohexane, ethyl acetate or methanol in ethyl acetate where appropriate.

| Example No. | R | MS m/z (M + H) | m.p. |
|---|---|---|---|
| 160 | NH-cyclobutyl | 482,484 | 192-193° C. |
| 161 | NH$_2$ | 428,430 | 187-189° C. |
| 162 | NHMe | 442,444 | 200-201° C. |
| 163 | NHEt | 456,458 | 146-147° C. |
| 164 | NH$^n$Pr | 470,472 | 150-151° C. |
| 165 | NH$^i$Pr | 470,472 | 124-125° C. |
| 166 | NMe$_2$ | 456,458 | |
| 167 | NHCH$_2$CH$_2$Ph | 532,534 | |
| 168 | NHCH$_2$CF$_3$ | 510,512 | |
| 169 | ![thiomorpholine dioxide] | 546,548 | |
| 170 | NHCH$_2$-cyclopropyl | 482,484 | 187-188° C. |
| 171 | NH-cyclopentyl | 496,498 | 182-183° C. |
| 172 | NH-cyclopropyl | 468,470 | 145-147° C. |
| 173 | NH$^n$Bu | 484,486 | oil |
| 174 | NH$^t$Bu | 484,486 | 102-110° C. |
| 175 | NHCH(Et)$_2$ | 498,500 | 89-92° C. |
| 176 | NH-allyl | 468,470 | 132-134° C. |
| 177 | NHNH$^t$Bu | 499,501 | |

Example 178

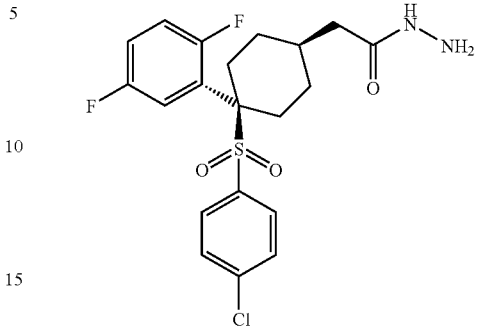

Step (1)

To a solution of the acid from Example 50 (1 g) in DCM (50 ml) and ethyl acetate (30 ml) was added pentafluorophenol (1.5 equiv.) and DCC (1.5 equiv.) and stirred at room temperature for 1 h. The reaction mixture was evaporated in vacuo, taken up in ethyl acetate and filtered. The filtrate was evaporated in vacuo to yield the pentafluorophenol ester of sufficient purity to use in subsequent reactions without further purification.

Step (2)

To the active ester prepared in Step (1) (200 mg, 0.33 mmol) dissolved in dry THF (3 ml) and under nitrogen was added hydrazine (1 M solution in THF, 1.3 ml, 1.32 mmol). After 3 h the reaction was concentrated diluted with water, extracted with ethyl acetate (×3), washed with, water, brine, dried (MgSO$_4$), filtered and evaporated. Purified by flash column chromatography (1:1 $^t$hexane/ethyl acetate to ethyl acetate+3% triethylamine) to give a white solid (50 mg). MS(EI+) 444 (MH+)

Example 179

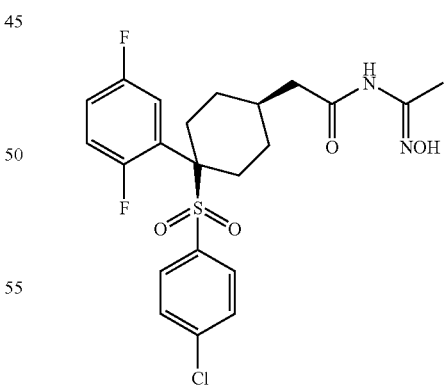

A solution of the active ester from step (1) of Example 178 in DMF was treated with acetamidoxime at room temperature. The reaction mixture was stirred for 0.5 h, diluted with ethyl acetate, washed with water, dried, filtered and evaporated in vacuo. Purification by column chromatography gave the desired product as a white solid (180 mg, 100%). MS MH+ 485(487).

Example 180

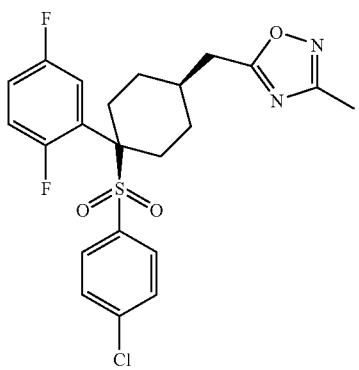

A solution of the oxime from Example 179 (100 mg) in THF (5 ml) was treated with potassium tert-butoxide solution (3 equiv.) and stirred at room temperature for 15 mins. The reaction mixture was diluted with water and ethyl acetate. The organic phase washed, dried, filtered and evaporated. Purification by column chromatography gave the desired product (65 mg, 62%) as a white solid. MS MH+ 467(469).

Example 181

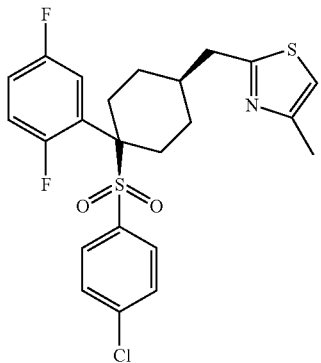

A solution of the amide from Example 161 (100 mg) was dissolved in dioxane and treated with Lawesson's reagent and stirred at room temperature overnight. The reaction mixture was filtered and the filtrate was evaporated in vacuo. Purification by column chromatography gave the thioamide (50 mg, 52%) as a white solid. A solution of the foregoing thioamide (40 mg) in ethanol (2 ml) was treated with chloroacetone (1.3 equiv.) and refluxed for 4 h. The reaction mixture was evaporated in vacuo. Trituration from hexane-ethyl acetate gave the desired product (26 mg, 59%) as a white solid. MS MH+ 482(484).

Example 182

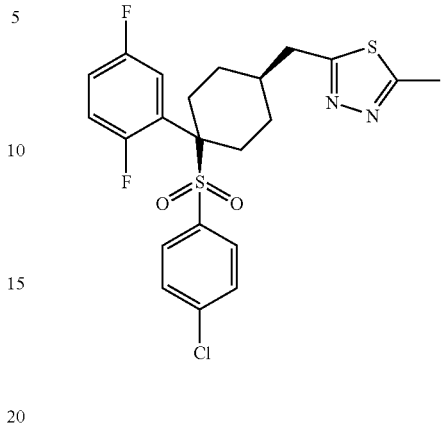

A solution of the active ester from Example 178 step (1) in DMF was treated with acetic hydrazide and stirred at room temperature for 15 min. The reaction mixture was diluted with ether and the precipitate was collected by filtration and washed several times with ether to give the intermediate diacyl hydrazide as a white solid. A solution of the foregoing compound (100 mg) in dioxane was treated with Lawesson's reagent (2 equiv.) and stirred at room temperature for 1 h. The reaction mixture was evaporated in vacuo. Purification by column chromatography gave the desired product (55 mg, 52%) as a white solid. MS MH+ 483(485).

Example 183

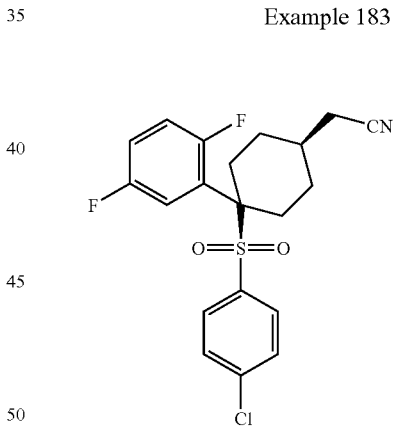

To a solution of the cis amide from Example 128 (46 mg) and pyridine (0.053 ml) in tetrahydrofuran (1 ml) was added trifluoroacetic anhydride (0.056 ml). The solution was stirred at room temperature for 2 hours when 0.5M–HCl (aqueous) and ethyl acetate were added. The organic phase was dried (MgSO$_4$), evaporated to a small volume and purified by chromatography on silica gel, eluting with isohexane:ethyl:acetate (5:1) to give the desired product as a colourless solid. $^1$H NMR (360 MHz, CDCl$_3$) Λ 1.61-1.70 (2H, m), 1.86-1.94 (2H, m), 2.03-2.10 (1H, m), 2.42-2.45 (4H, m), 2.51(2H, d J 8.0 Hz), 6.8 (1H, m), 7.02-7.09(2H, m), 7.30 (2H, d J 8.6 Hz), 7.36(2H, d J 8.7 Hz).

Example 184

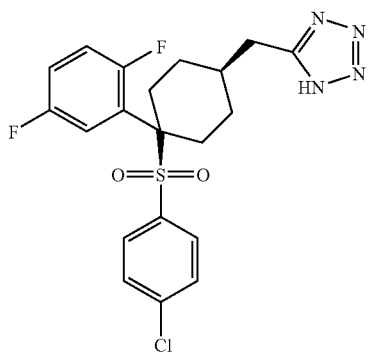

To a solution of the nitrile from Example 183 (0.43 g) in dimethylformamide (0.5 ml) was added ammonium chloride (0.15 g) and sodium azide (0.15 g) and the mixture was heated at 100° C. for 12 h. 0.2M–HCl (5 ml) and ethyl acetate (5 ml) were added and the organic phase washed with water (5 times) and dried (MgSO$_4$). The solvent was removed in vacuo and the residue was purified by chromatography on silica gel (eluting with ethyl acetate, 5% methanol in ethyl acetate) to give the desired product MS m/z 451 (M–H)

Example 185

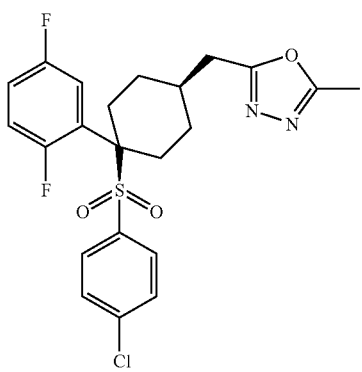

The nitrile from Example 183 (300 mg) was dissolved in methanol (3 ml) and ether (20 ml), cooled to 0° C. and treated with HCl gas for 10 minutes. The reaction vessel was stoppered and left to stand at room temperature overnight. The reaction mixture was evaporated in vacuo to give the imidate ether hydrochloride salt (350 mg, ca 100%) as a white solid.

A solution of the foregoing imidate ether hydrochloride salt (100 mg) in methanol (10 ml) was treated with acetic hydrazide (1.5 equiv.) and stirred at room temperature for 5 min. The reaction mixture was evaporated in vacuo and taken up in Dowtherm A, treated with ammonium chloride (100 mg) and heated at 190° C. for 2 h. The reaction mixture was cooled and purified by column chromatography to give the desired product (24 mg, 24%) as a white solid. MS MH+ 467(469).

Example 186

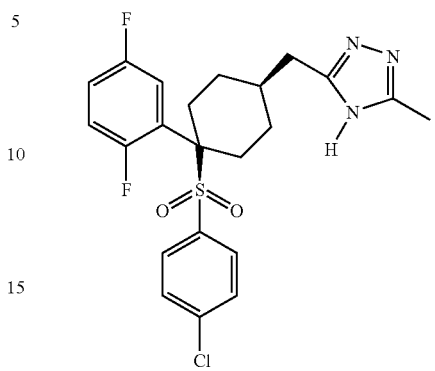

A suspension of the hydrazide of Example 178 (160 mg) in methanol (10 ml) was treated with a solution of acetamidine (2 equiv.) in ethanol (1 ml) and stirred at room temperature overnight, then refluxed for 2 h. The reaction mixture was evaporated in vacuo, dissolved in N-methylpyrrolidinone (2 ml) and xylene (30 ml) and refluxed overnight with the azeotropic removal of water. The reaction mixture was evaporated in vacuo, dissolved in ethyl acetate and washed with water (three times). The organic phase was dried, filtered and evaporated. Purification by column chromatography gave the desired product (137 mg, 76%) as a white solid. MS MH+ 466(468).

Example 187

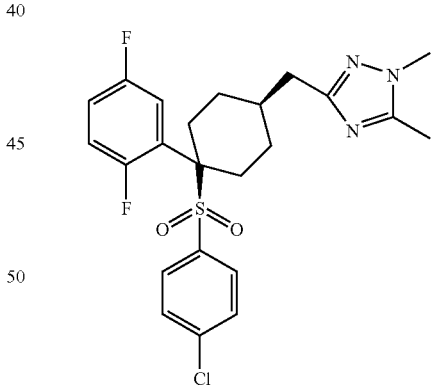

A solution of the triazole from Example 186 (50 mg) in DMF (1 ml) was treated with sodium hydride (1.1 equiv.) and, after 5 minutes, methyl iodide (1.5 equiv.). After 1 h, the reaction mixture was diluted with ethyl acetate and water. The organic layer washed with water, dried, filtered and evaporated in vacuo. Purification by column chromatography gave the desired product (33 mg, 64%) as a white foam. $^1$H NMR indicated this compound to be a mixture of N1/N2 methylated regioisomers. MS MH+ 480(482).

Example 188

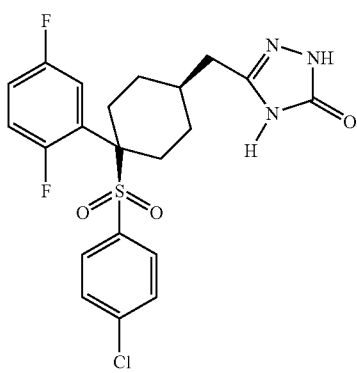

A solution of the active ester from Example 178 step (1) (200 mg) in toluene was treated with a suspension of semicarbazide hydrochloride (1.1 equiv.) in DMF and triethylamine (2.2 equiv.) and stirred at room temperature for half an hour. The reaction mixture was diluted with ether and filtered. The residue washed with ether to give the crude acyl semicarbazide as a white solid.

A suspension of this material (150 mg) in 1 M NaOH solution (20 ml) and a small amount of 1,4-dioxane was refluxed overnight. The reaction mixture was cooled and acidified with 1 M HCl. The resulting precipitate was collected by filtration, washed with water and ether several times and dried in vacuo to give the desired product as a white solid. MS MH+ 468(470).

Example 189

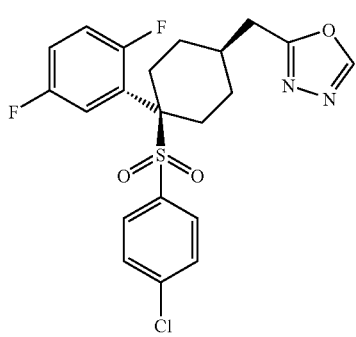

The hydrazide prepared in Example 178 (40 mg, 0.09 mmol) was dissolved in triethyl orthoformate (3 ml) and heated at 150° C. for 18 h. Reaction was concentrated and purified by flash chromatography (1:1 $^i$hexane/ethyl acetate) to give a colourless glassy solid (12 mg). $^1$H NMR (CDCl$_3$) 1.55-1.62 (2H, m), 1.77-1.82 (2H, m), 2.20-2.28 (1H, m), 2.44 (1H, s), 2.50 (3H, dd, J=5.5, 14.5 Hz), 3.07 (2H, d, J=7.8 Hz), 6.80-6.87 (1H, m), 7.01-7.09 (2H, m), 7.31-7.38 (4H, m), 8.36 (1H, s).

Example 190

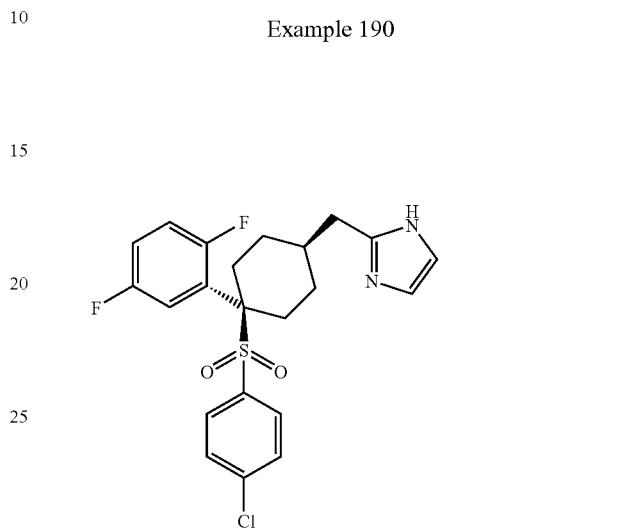

To the acid prepared in Example 50 (1.0 g, 2.3 mmol) dissolved in THF (80 ml) under nitrogen and cooled to 0° C. were added triethylamine (0.4 ml, 2.8 mmol) and isobutylchloroformate (0.36 ml, 2.8 mmol). Reaction was stirred at 0° C. for 2 h and then the solid in the reaction mixture was removed by filtration. The filtrate was recooled to 0° C. and sodium borohydride (435 mg) in water (10 ml) added dropwise and the reaction was stirred for 1 h. Reaction was concentrated, diluted with ethyl acetate, washed with water, brine, dried (MgSO$_4$), filtered and evaporated. Purified by flash chromatography (1:1 $^i$hexane/ethyl acetate) to give the alcohol (0.96 g).

To the alcohol (400 mg, 0.97 mmol) dissolved in DCM (20 ml) was added Dess-Martin periodinane (453 mg, 1.1 mmol). Reaction stirred for 1 h and then filtered through a pad of Celite™ and the filtrate evaporated and the residue purified by flash chromatography (2:1 $^i$hexane/ethyl acetate) to give the aldehyde (250 mg) which was dissolved in ethanol (5 ml), cooled to 0° C. and treated with glyokal (40% w/w aq solution, 0.2 ml) and ammonia (25% w/w aq. solution, 1 ml). After 30 min the reaction was allowed to warm to room temperature and stirred for 15 h. After concentration the residue was diluted with brine and extracted with ethyl acetate (×3). Organic extracts were dried (MgSO$_4$), filtered and evaporated to give the imidazole as a white solid (150 mg). $^1$H NMR (CDCl$_3$) 1.45-1.55 (2H, m), 1.70-1.75 (2H, m), 2.17-2.22 (1H, m), 2.46 (4H, dd, J=5.6, 14.0 Hz), 2.88 (2H, d, J=7.7 Hz), 6.78-6.85 (1H, m), 6.98 (2H, s), 7.00-7.05 (2H, m), 7.31-7.36 (4H, M), 9.1-9.8 (1H, br).

Example 191

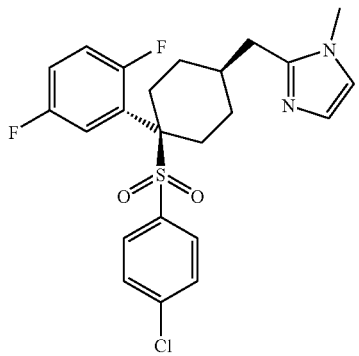

The imidazole prepared in Example 190 (35 mg, 0.078 mmol) was dissolved in dry DMF (2 ml) and treated with potassium carbonate (53 mg, 0.39 mmol) and iodomethane (6 µl, 0.096 mmol) and allowed to stir for 48 h. The reaction was diluted with water and extracted with ethyl acetate (×3). Organic extracts were dried (MgSO$_4$), filtered and evaporated and purified by flash chromatography (ethyl acetate) to give a white solid (8 mg). $^1$H NMR (CDCl$_3$) 1.51-1.59 (1H, m), 1.80 (4H, dd, J=3.9, 10.5 Hz), 2.19-2.26 (1H, m), 2.42-2.57 (3H, m), 2.80 (2H, d, J=7.7 Hz), 3.60 (3H, s), 6.79 (1H, d, J=1.1 Hz), 6.81-6.86 (1H, m), 6.94 (1H, d, J=1.4 Hz), 7.00-7.08 (2H, m), 7.34 (4H, d, J=4.2 Hz).

Example 192

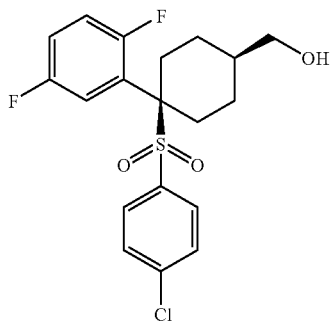

The acid from Example 127 (153 mg) was dissolved in dry THF (10 ml) and cooled to 0° C. under nitrogen. Triethylamine (61 µL, 0.43 mmol) and isobutylchloroformate (57 µL, 0.43 mmol) were added and the mixture stirred at 0° C. for one hour. The precipitate that had formed was removed by filtration and washed with a further 5 ml of dry THF. The combined THF layers were recooled to 0° C. and sodium borohydride (70 mg, 1.84 mmol) as a solution in water (2 ml) was added with effervescence. After stirring for 30 minutes at 0° C., the reaction was diluted with ethyl acetate, washed with ammonium chloride solution, sodium bicarbonate solution and brine then dried (MgSO$_4$) and evaporated to dryness. The residue was purified by column chromatography eluting with ethyl acetate:hexane (1:3) to afford the desired alcohol (75 mg). $^1$H NMR (CDCl$_3$) 7.39-7.31 (4H, m), 7.10-7.01 (2H, m), 6.88-6.81 (1H, m), 3.71 (2H, d, J=7.5 Hz), 2.46-2.32 (4H, m), 1.90-1.85 (2H, m), 1.78-1.74 (1H, m) and 1.54-1.44 (2H, m). m/z=423 [MNa]$^+$

Example 193

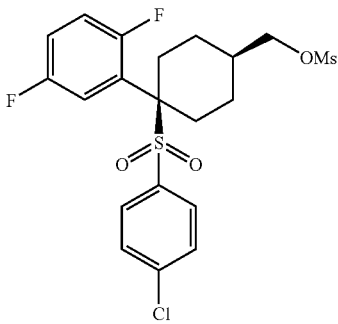

A stirred solution of the alcohol from Example 192 (294 mg, 0.74 mmol) in DCM (10 ml) was cooled to −30° C. Triethylamine (155 µl, 1.11 mmol) then methanesulfonyl chloride (68 µl, 0.89 mmol) were added and the mixture stirred for 30 minutes at −30° C. The reaction was diluted with water, warmed to ambient temperature and extracted with DCM. The organic layer washed with citric acid solution and sodium bicarbonate solution, dried (MgSO$_4$) and evaporated to dryness. The residue (321 mg) could be used without further purification or purified by column chromatography eluting with ethyl acetate:hexane (1:3) to remove small quantities of the trans isomer to afford the desired product. (272 mg). $^1$H NMR (CDCl$_3$) 7.36 (2H, d, J=8.5 Hz), 7.31 (2H, d, J=8.5 Hz), 7.08-7.02 (2H, m), 6.87-6.83 (1H, m), 4.29 (1H, d, J=7.5 Hz), 3.05 (3H, s), 2.46-2.42 (4H, m), 2.05-2.02 (1H, m), 1.93-1.88 (2H, m) and 1.62-1.55 (2H, m). m/z=501 [MNa]$^+$

Example 194

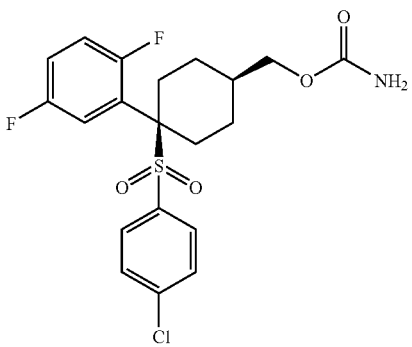

To a stirred solution of the alcohol from Example 192 (59 mg, 0.15 mmol) in dry THF (5 ml) cooled to 0° C. under nitrogen was added chlorosulfonyl isocyanate (18 µl, 0.21 mmol). The mixture was stirred for 45 minutes at this temperature then sodium metabisulfite (84 mg, 0.44 mmol) as a solution in water (1 ml) was added and stirring continued for 16 hours at room temperature. Ethyl acetate was added and the mixture washed with water (×2), brine, dried (MgSO$_4$) and evaporated to leave a residual solid (73 mg) which was triturated with ether and filtered to afford the desired product (35 mg). ¹H NMR (DMSO) 7.61 (2H, d, J=8.5 Hz), 7.36 (2H, d, J=8.5 Hz), 7.35-7.30 (1H, m), 7.25-7.10 (2H, m), 6.47 (2H, br s), 3.95 (2H, d, J=7.5 Hz), 3.16 (1H, m), 2.44 (1H, m), 2.23-2.14 (2H, m), 1.85-1.67 (3H, m) and 1.38-1.26 (2H, m). m/z=444 [MH]⁺

Example 195

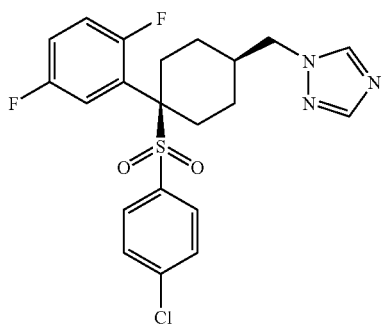

A stirred solution of 1,2,4-triazole sodium derivative (95 mg, 1.04 mmol) in DMSO (5 ml) and the mesylate from Example 193 (100 mg, 0.21 mmol) were heated to 100° C. for 17 hours. The reaction was cooled, diluted with dichloromethane and washed with water, brine (×2), dried (MgSO₄) and evaporated to leave a residue which was purified by preparative thin layer chromatography eluting with ether:dichloromethane 1:1 to afford the desired product. ¹H NMR (CDCl₃) 8.09 (1H, s), 7.95 (1H, s), 7.36 (2H, d, J=8.5 Hz), 7.31 (2H, d, J=8.5 Hz), 7.07-7.02 (2H, m), 6.85-6.81 (1H, m), 4.27 (2H, d, J=8 Hz), 2.58-2.39 (4H, m), 2.28-2.22 (1H, m), 1.75-1.68 (2H, m) and 1.6-1.48 (2H, m). m/z=452 [MH]⁺.

Example 196

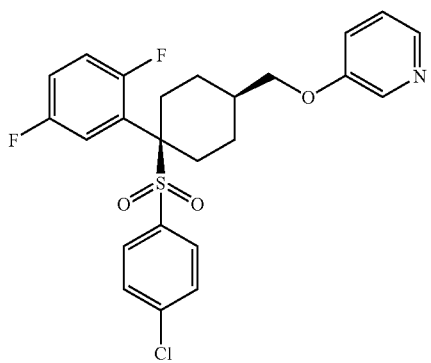

To a stirred solution of the alcohol from Example 192 (114 mg, 0.29 mmol) in dry THF (10 ml) was added 3-hydroxypyridine (30 mg, 0.32 mmol), triphenylphosphine (164 mg, 0.63 mmol) and diethylazodicarboxylate (55 μl, 0.35 mmol) and the resulting solution stirred at ambient temperature for 20 hours. The mixture was evaporated and purified by column chromatography eluting with ethyl acetate:hexane (1:1) to afford the desired product. (52 mg). ¹H NMR (CDCl₃) 8.33 (1H, s), 8.24 (1H, s), 7.37-7.30 (4H, m), 7.25-7.20 (2H, m), 7.11-7.03 (2H, m), 6.88-6.82 (1H, m), 4.07 (2H, d, J=7.5 Hz), 2.50-2.43 (4H, m), 2.13-2.09 (1H, m), 2.01-1.96 (2H, m) and 1.67-1.56 (2H, m). m/z=478[MH]⁺

Example 197

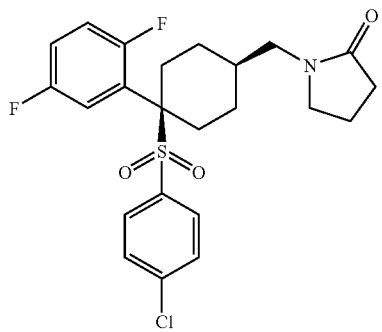

To a stirred solution of pyrrolidin-2-one (23 mg, 0.27 mmol) in DMF (10 ml) under nitrogen was added sodium hydride (11 mg of a 60% dispersion in mineral oil, 0.27 mmol) and the mixture stirred at ambient temperature for 20 minutes. After this time, a solution of the mesylate from Example 193 (44 mg, 0.09 mmol) in DMF (2 ml) was added and the mixture heated to 80° C. for 4 hours. The reaction was cooled, diluted with ethyl acetate and washed with ammonium chloride solution, sodium bicarbonate solution, brine, dried (MgSO₄) and evaporated to leave a residue which was purified by preparative thin layer chromatography eluting with ethyl acetate:hexanes 3:1 to afford the desired product (9 mg).

¹H NMR (CDCl₃) 7.37 (4H, s), 7.08-7.00 (2H, m), 6.88-6.81 (1H, m), 3.38-3.34 (4H, m), 2.51-2.38 (6H, m), 2.06-1.98 (2H, m), 1.92-1.87 (1H, m), 1.70-1.64 (2H, m) and 1.51-1.42 (2H, m). m/z=292[M-ArSO₂⁻]⁺

Using the general procedure of Example 197, and substituting the appropriate nucleophile for pyrrolidin-2-one, the following were prepared:

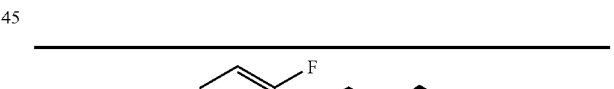

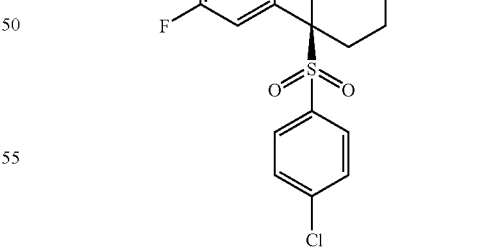

| Example No. | NR₂ | m/z |
|---|---|---|
| 198 | 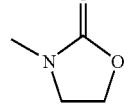 | 294 [M-ArSO₂⁻]⁺ |

-continued

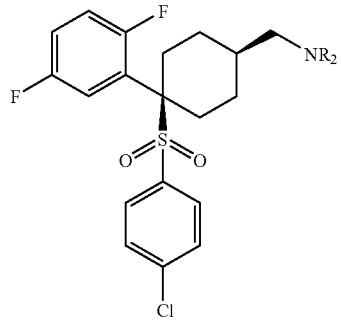

| Example No. | NR₂ | m/z |
|---|---|---|
| 199 | 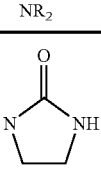 | 292 [M-ArSO₂⁻]⁺ |
| 200 | 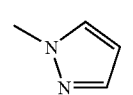 | 275 [M-ArSO₂⁻]⁺<br>451 [MH]⁺ |
| 201 | 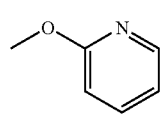 | 302 [M-ArSO₂⁻]⁺<br>478 [MH]⁺ |
| 202 | 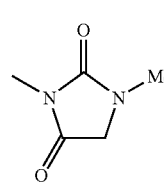 | 321 [M-ArSO₂⁻]⁺<br>497 [MH]⁺ |
| 203 | 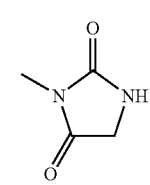 | 307 [M-ArSO₂⁻]⁺<br>483 [MH]⁺ |
| 204 | 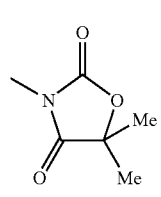 | *** |
| 205* | 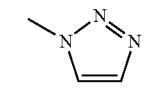 | 452 [MH]⁺ |
| 206* | 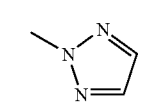 | 452 [MH]⁺ |
| 207 | 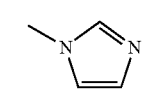 | 451 [MH]⁺ |

-continued

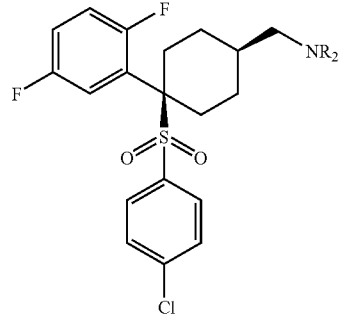

| Example No. | NR₂ | m/z |
|---|---|---|
| 208** | 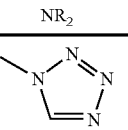 | 453 [MH]⁺ |
| 209** | 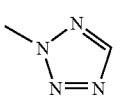 | 453 [MH]⁺ |
| 210 | 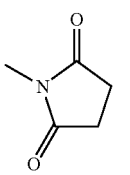 | 482 [MH]⁺ |

*obtained as a mixture using 1,2,3-triazole as nucleophile, and separated by preparative TLC (2:1 DCM/hexane 2% MeOH).
**obtained as a mixture using 1,2,3,4-tetrazole as nucleophile, and separated by preparative TLC.
***¹H NMR (CDCl₃) 7.36(4H, br s), 7.06-7.04(2H, m), 6.89-6.80(1H, m), 3.64-3.62(2H, d, J=7.5Hz), 2.53-2.46(4H, m), 2.04-2.01(1H, m), 1.69-1.68(2H, m) and 1.51-1.50(2H, m).

Example 211

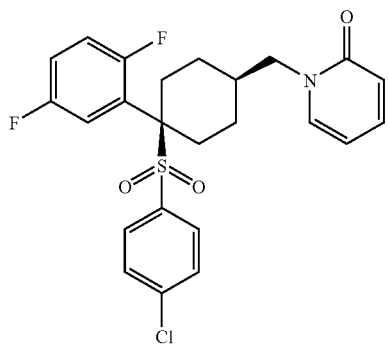

A stirred solution of 2-hydroxypyridine (60 mg, 0.63 mmol) in DME (4 ml) and DMF (1 ml) under nitrogen was cooled to 0° C. Sodium hydride (28 mg of a 60% dispersion in mineral oil, 1.15 mmol) was then added and the suspension stirred at 0° C. LiBr (109 mg, 1.26 mmol) was added 10 minutes later. After this time, the mixture was warmed to ambient temperature and stirred for 15 minutes. A solution of the mesylate from Example 193 (60 mg, 0.13 mmol) in DMF (2 ml) was added and the mixture heated to 65° C. for 18 hours. The reaction was cooled, diluted with ethyl acetate and washed with ammonium chloride solution, sodium bicarbonate solution and brine then dried (MgSO₄) and evaporated to leave a residue which was purified by preparative thin layer chromatography eluting with EtOAc:Hexane 1:5 to afford the desired product (4 mg).

¹H NMR (CDCl₃) 7.55-7.30 (5H, m), 7.25-7.22 (1H, dd J=7.0, 2.0 Hz), 7.09-7.00 (2H, m), 6.85-6.78 (1H, m), 6.58-6.55 (1H, d, J=9.0 Hz), 6.18-6.14 (1H, m), 4.02-3.99 (2H, d, J=8.0 Hz), 2.62-2.55 (2H, m), 2.44 (2H, m), 2.19-2.17 (1H, m), 1.80-1.76 (2H, m) and 1.6-1.5 (2H, m).

Example 212

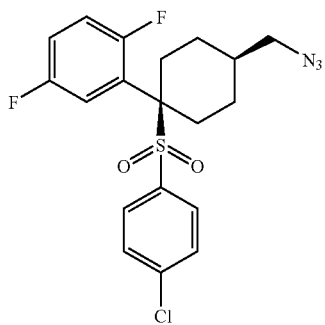

To a stirred solution of the mesylate from Example 193 (90 mg, 0.19 mmol) in DMF (10 ml) under nitrogen was added sodium azide (49 mg, 0.76 mmol) and the mixture stirred and heated to 100° C. for 2 hours. After this time, the reaction was cooled, diluted with water and extracted with ethyl acetate (×2), the combined organic layers were washed with water, dried (MgSO₄) and evaporated to leave a residue (76 mg) which was purified by preparative thin layer chromatography eluting with 4% EtOAc:Hexane to afford the desired product.

¹H NMR (CDCl₃) 7.38-7.30 (4H, m), 7.09-7.01 (2H, m), 6.87-6.80 (1H, m), 3.43-3.41 (2H, d, J=8.0 Hz), 2.46-2.35 (4H, m), 1.87-1.79 (3H, m), 1.56-1.50 (2H, m).

Example 213

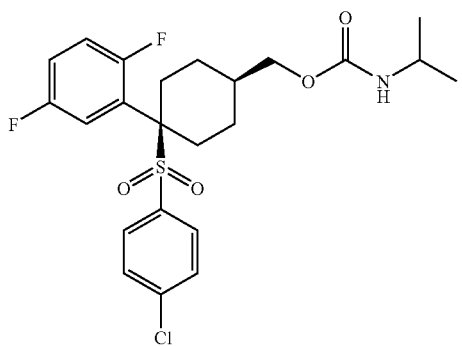

Step (1)

The alcohol from Example 192 (181 mg, 0.46 mmol) was dissolved in THF and pyridine (37 μl, 0.46 mmol) added followed by 4-nitrophenyl chloroformate (103 mg, 0.51 mmol). The reaction was stirred overnight at room temperature then the solvent removed in vacuo and the reaction taken up in ether and washed with water (×2) and brine (×2), dried (MgSO₄) and evaporated to a foam (247 mg). Product was purified by flash column chromatography (1% MeOH, 99% DCM) to yield the desired 4-nitrophenylcarbonate (230 mg)

Step (2)

The carbonate (74 mg, 0.14 mmol) was dissolved in DMF (2 ml) and isopropylamine (23 μl, 0.28 mmol) added. The reaction was stirred for 10 minutes then diluted with ethyl acetate and washed with 2N NaOH (×3) and brine (×3), dried (MgSO₄) and evaporated to dryness. The crude product was purified by prep plate (2:1 hexane:ethyl acetate) affording the desired product (18 mg). 1H NMR (CDCl₃) 7.38-7.30 (4H, m), 7.09-6.99 (2H, m), 6.88-6.79 (1H, m) 4.57-4.48 (1H, s, broad), 4.13 (2H, d, J=8.5 Hz), 3.88-3.71 (1H, m), 2.49-2.38 (4H, m), 1.92-1.80 (3H, m) 1.55-1.41 (2H, m), and 1.16 (6H, d, J=6.5 Hz).

Example 214

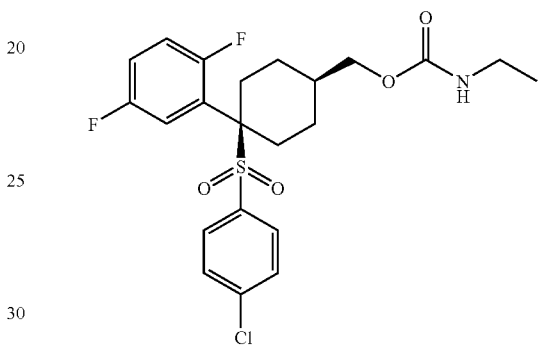

The carbonate from Example 213 step (1) (56 mg, 0.14 mmol) was dissolved in THF (2 ml) and ethylamine (0.4 ml, 0.28 mmol, 2M solution in THF) added. The reaction was stirred for 10 minutes then evaporated to a foam. The reaction was taken up in ethyl acetate and washed with 2N NaOH (×3) and brine (×3), dried (MgSO₄) and evaporated to dryness. The crude product was purified by prep plate (2:1 hexane:ethyl acetate) affording the desired product (18 mg). ¹H NMR (CDCl₃) 7.38-7.30 (4H, m), 7.09-6.99 (2H, m), 6.88-6.79 (1H, m) 4.61-4.70 (1H, s, broad), 4.14 (2H, d, J=7 Hz), 3.28-3.15 (2H, m), 2.49-2.38 (4H, m), 1.90-1.79 (3H, m) 1.55-1.42 (2H, m) and 1.15 (3H, t, J=7 Hz).

Example 215

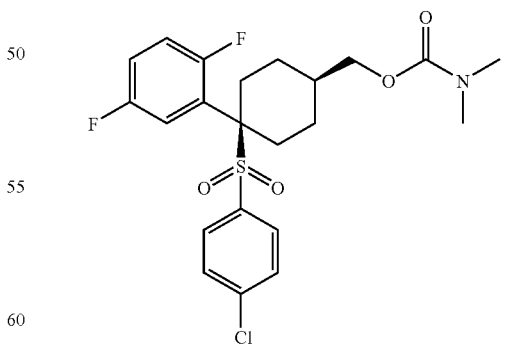

Prepared as for Example 214 using dimethylamine (2M solution in THF) as starting material. Yield 7 mg. ¹H NMR (CDCl₃) 7.38-7.30 (4H, m), 7.09-6.99 (2H, m), 6.88-6.78 (1H, m), 4.15 (2H, d, J=7 Hz), 2.91 (6H, s), 2.49-2.38 (4H, m), 1.95-1.80 (3H, m) and 1.55-1.48 (2H, m).

Example 216

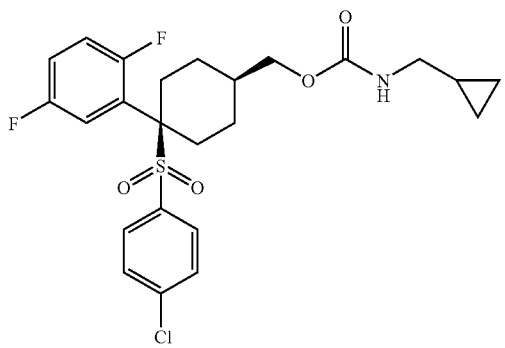

Prepared as for Example 214 using cyclopropylmethylamine as starting material. Yield 11 mg. $^1$H NMR (CDCl$_3$) 7.38-7.30 (4H, m), 7.09-7.00 (2H, m), 6.88-6.78 (1H, m), 4.87-4.75 (1H, s, broad), 4.14 (2H, d, J=7 Hz), 3.08-2.97 (2H, m), 2.47-2.38 (4H, m), 1.98-1.79 (3H, m), 1.55-1.41 (2H, m), 1.0-0.88 (1H, m), 0.53-0.46 (2H, m) and 0.20-0.12 (2H, m).

Example 217

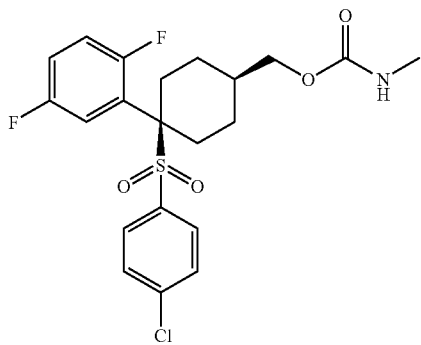

Prepared as for Example 214 using methylamine (8M solution in EtOH) as starting material. Yield 7 mg. $^1$H NMR (CDCl$_3$) 7.38-7.30 (4H, m), 7.09-7.00 (2H, m), 6.88-6.78 (1H, m), 4.68-4.56 (1H, s, broad), 4.14 (2H, d, J=7 Hz), 2.81 (3H, d, J=4.89), 2.48-2.38 (4H, m), 1.91-1.76 (3H, m) and 1.56-1.41 (2H, m).

Example 218

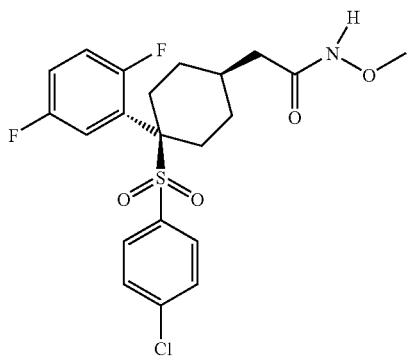

To the pentafluorophenol ester prepared in Example 178 step (1) (140 mg, 0.23 mmol) dissolved in DCM (3 ml) and under nitrogen were added methoxyamine hydrochloride (80 mg, 0.92 mmol) and triethylamine (0.1 ml). After 1 h the reaction was concentrated, diluted with ethyl acetate, washed with aq. sodium carbonate, water, brine, dried (MgSO$_4$), filtered and evaporated. Purified by flash column chromatography (1:1 $^i$hexane/ethyl acetate to ethyl acetate/methanol) to give a white solid (50 mg). $^1$H NMR (CDCl3) 1.56 (2H, br), 1.76 (2H, br), 2.25 (4H, br), 2.44 (4H, br), 3.78 (3H, s), 6.78-6.86 (1H, m), 7.01-7.06 (2H, m), 7.29-7.37 (4H, m).

Example 219

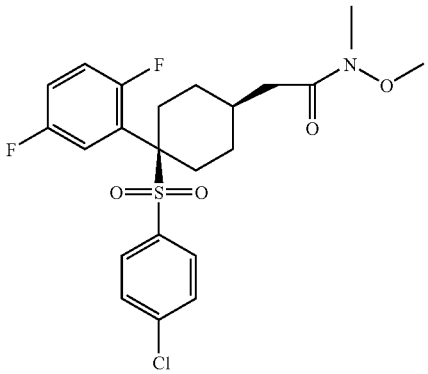

To a stirred suspension of cis 4-(4-chlorobenzenesulphonyl)-4-(2,5-difluorophenyl)cyclohexaneacetic acid (Example 50, 0.224 g, 0.52 mmol) in dichloromethane (5 ml) was added oxalyl chloride (0.075 ml, 0.86 mmol) and dimethylformamide (1 drop). After 30 minutes the solution was evaporated to a small volume and to a solution of the residue in dichloromethane (5 ml) was added N,O-dimethylhydroxylamine hydrochloride (0.068 g, 0.58 mmol) and diisopropylethylamine (0.2 ml, 1.14 mmol). After stirring the solution for 30 minutes the solvent was removed in vacuo and the residue purified by chromatography on silica gel eluting with increasing concentrations of ethyl acetate in isohexane (33%, 50%). The fractions containing the product were evaporated to give the desired product as a foam. $^1$H NMR (360 MHz, CDCl$_3$) Λ 1.50-1.56 (2H, m), 1.72-1.77 (2H, m), 2.24 (1H, m), 2.44 (4H, m), 2.57 (2H, d J 7.3 Hz), 3.2 (3H, s), 3.7 (3H, s), 6.80-6.88 (1H, m), 7.01-7.08 (2H, m), 7.31 (2H, dd J 6.7 Hz and 2.3 Hz), 7.36 (2H, dd J 6.7 Hz and 2.3 Hz).

Example 220

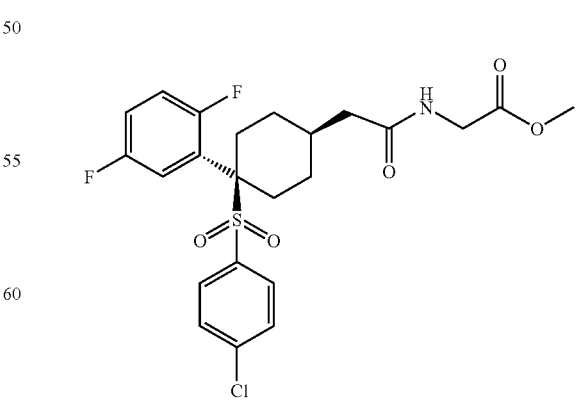

To the pentafluorophenol ester prepared in Example 178 step (1) (155 mg, 0.25 mmol) dissolved in DMF (3 ml) and under nitrogen were added glycine methyl ester hydrochloride (125 mg, 1.0 mmol) and triethylamine (0.15 ml). After 2 h the reaction was diluted with water, extracted with ethyl acetate (×3), washed with, water, brine, dried (MgSO$_4$), filtered and evaporated. Purified by flash column chromatography (1:1 $^i$hexane/ethyl acetate to 9:1 ethyl acetate/methanol) to give a white solid (55 mg). $^1$H NMR (CDCl$_3$) 1.08-1.16 (1H, m), 1.30-1.37 (1H, m), 1.67-1.71 (1H, m), 1.75-1.79 (2H, m), 1.91-1.95 (1H, m), 2.20-2.26 (1H, m), 2.41 (4H, d, J=7.8 Hz), 3.77 (3H, s), 4.05 (2H, d, J=5.1 Hz), 6.19 (1H, br), 6.79-6.85 (1H, m), 7.00-7.07 (2H, m), 7.30-7.37 (4H, m).

Example 221

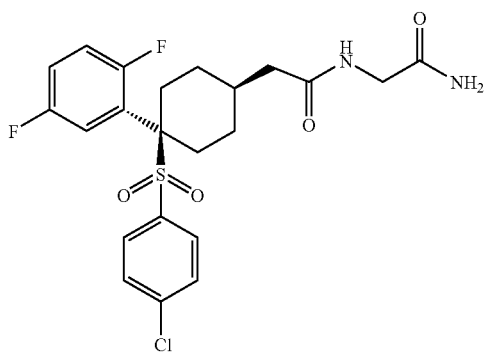

The glycine ester prepared in Example 220 (50 mg, 0.1 mmol) in a sealed tube and dissolved in a 2M ammonia in methanol solution (3 ml) was heated to 50° C. for 3 h. After cooling to room temperature the reaction mixture was concentrated and purified by trituration with ether to give a white solid (28 mg). MS(EI+): 485 (MH+)

Example 222

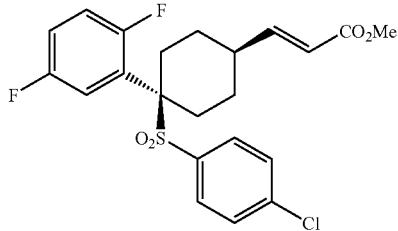

The alcohol from Example 192 (4 g, 10 mmol) was dissolved in dichloromethane (280 ml) and was treated with Dess Martin periodinane (4.66 g, 11 mmol) and the mixture was stirred for 45 mins before adding saturated aqueous sodium bisulphite (100 ml) and after 5 mins the mixture was separated and the organic phase as washed with saturated aqueous sodium bicarbonate (100 ml) dried (MgSO$_4$) and evaporated to dryness. The crude residue (4 g) was dissolved in dry dichloromethane (100 ml) and treated with methyl triphenylphosphinoacetate (4.7 g 14 mmol), stirring at rt. for 16 hrs. The solvent was evaporated and the residue was purified by column chromatography on silica gel eluting with 10-20% ethyl acetate in hexanes, to give the product. $^1$H NMR (CDCl$_3$) 7.37-7.36 (4H, m), 7.10-7.02 (3H, m), 6.87-6.83 (1H, m), 5.91 (1H, d, J=16 Hz), 3.77 (3H, s), 2.55-2.45 (3H, m), 2.40-2.38 (2H, m), 1.95-1.90 (2H,m) and 1.65-1.52 (1H, m).

Example 223

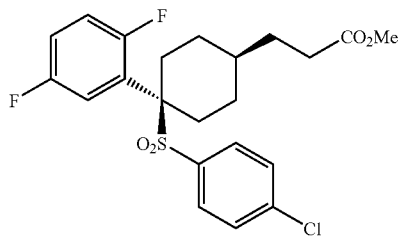

The alkene from Example 222 (3.6 g, 9 mmol) was dissolved in ethyl acetate (350 ml). The flask was degassed and then 10% palladium on carbon (400 mg) was added and the mixture stirred under an atmosphere of hydrogen for 45 mins. The solution was filtered through Celite™ and evaporated. The clear oil obtained was purified by preparative tlc eluting with 5% ethyl acetate in hexanes. The oil obtained was then further purified by column chromatography on silica gel eluting with 5-10% ethyl acetate in hexane to give the product. $^1$H NMR (CDCl$_3$) 7.37-7.34 (4H, m), 7.08-7.00 (2H, m), 6.85-6.81 (1H, m), 3.67 (3H, s), 2.45-2.39 (4H, m), 2.33 (2H, t, J=8.4 Hz), 1.81 (2H, q, J=8.4 Hz), 1.72-1.68 (2H,m) and 1.60-1.43 (3H, m).

Example 224

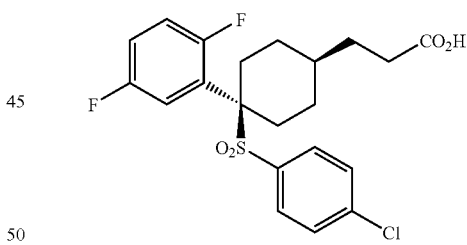

The ester from Example 223 (104 mg, 0.23 mmol) was dissolved in a mixture of ethanol (10 ml) and water (3 ml) and stirred at 20° C. The flask was degassed and then lithium hydroxide (27 mg, 1.15 mmol) was added. The mixture was stirred for 3 hrs. at room temperature. 1N Hydrochloric acid was then added and the mixture washed with ethyl acetate (2×50 ml). The organic phase washed with brine (50 ml), dried (MgSO$_4$) and evaporated. The oil obtained was then further purified by preparative tlc eluting with ethyl acetate to give the acid. $^1$H NMR (CDCl$_3$) 7.37-7.30 (4H, m), 7.09-6.99 (2H, m), 6.85-6.79 (1H, m), 2.42-2.36 (6H, m), 1.85-1.79 (2H, m), 1.73-1.69 (2H,m), 1.63-1.58 (1H,m) and 1.53-1.45 (2H, m).

Example 225

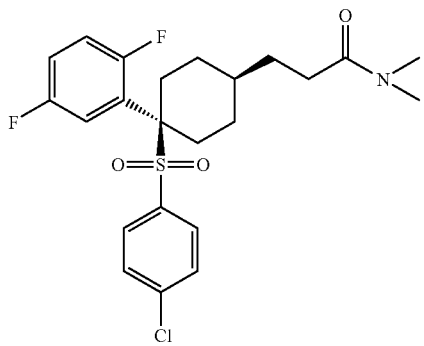

The acid from Example 224 (52 mg, 0.118 mmol) in dichloromethane (2 ml) was treated with oxalyl chloride (88 μl, 2 M solution in dichloromethane, 0.176 mmol). A drop of N,N-dimethylformamide was added and the solution allowed to stir for 2 hours. After this time, solvent was removed in vacuo and the residue redissolved in dichloromethane (1 ml). This solution was dripped into methanolic ammonia (2 M, 2 ml). The reaction was evaporated in vacuo and the residue chromatographed on silica, eluting with 80% ethyl acetate in hexanes. The resulting material was purified further by preparative t.l.c., eluting with 100% ethyl acetate followed by recrystallisation from hot hexane to give product (7.4 mg, 14%). $^1$H NMR (360 MHz, CDCl$_3$), 1.45-1.53 (2H, m), 1.57-1.65 (1H, br), 1.70-1.75 (2H, m), 1.78-1.84 (2H, m), 2.32 (2H, t, J=15.3 Hz), 2.38-2.44 (4H, br), 2.95 (3H, s), 3.02 (3H, s), 6.79-6.86 (1H, m), 7.00-7.09 (2H, m), 7.31-7.37 (4H, m); ms. (ES+), 470 (M$^+$1), 294 (M$^+$175).

Example 226

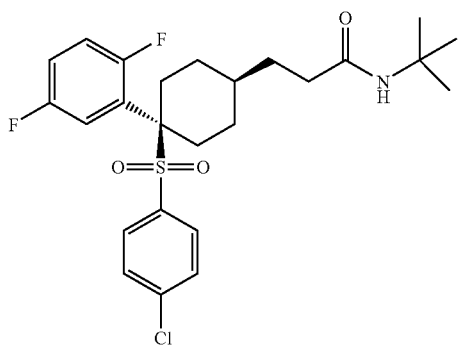

The acid from Example 224 (52 mg, 0.118 mmol) in dichloromethane (2 ml) was treated with 1-(3-dimethylaminopropyl)-3-ethylcarbodiimide hydrochloride (45 mg, 0.235 mmol), triethylamine (32.7 μl, 0.235 mmol) and tert-butylamine (24.6 μl, 0.235 mmol). After 2 hours stirring at room temperature, reaction washed with hydrochloric acid (1 N, 10 ml), organics dried (MgSO$_4$) and evaporated in vacuo to give crude (55 mg). This material was chromatographed on silica, eluting with 20-30% ethyl acetate in hexanes to give product (25 mg, 43%). $^1$H NMR (400 MHz, CDCl$_3$), 1.35 (9H, s), 1.45-1.62 (3H, m), 1.67-1.74 (2H, m), 1.76-1.80 (2H, m), 2.08-2.12 (2H, m), 2.38-2.42 (4H, br), 5.72-5.78 (1H, br), 6.76-6.88 (1H, m), 7.00-7.10 (2H, m), 7.31-7.37 (4H, m).

Example 227

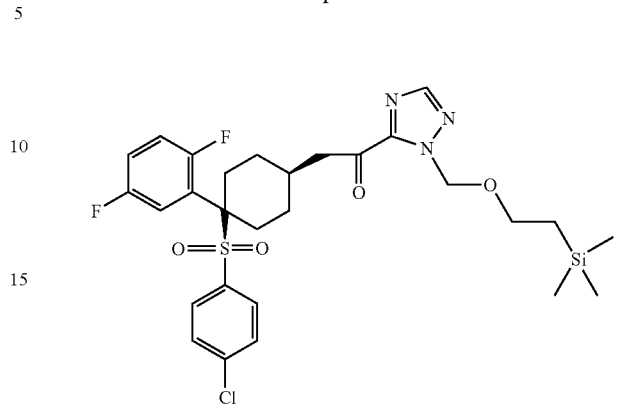

To a cooled (−80° C.) solution of 1-(trimethylsilylethyloxymethyl)triazole (0.109 g, 0.55 mmol) in tetrahydrofuran (2 ml) was added a solution of n-butyl lithium (2.5M in hexanes, 0.22 ml). The solution was stirred at −80° C. for 15 minutes, warmed to 0° C. for 5 minutes and then recooled to −80° C. To the cooled solution was added a solution of cis 4-(4-chlorobenzenesulphonyl)-4-(2,5-difluorophenyl)cyclohexaneacetic acid N,O-dimethylhydroxamate (Example 219) (217 mg, 0.46 mmol) in tetrahydrofuran (3 ml). After stirring the mixture at −80° C. for 15 minutes a saturated solution of aqueous ammonium chloride was added and the product extracted with ethyl acetate. The organic phase was dried (MgSO$_4$), evaporated to dryness and purified by chromatography on silica gel (eluting with 25% ethyl acetate in hexane) to give the desired product as a crystalline solid. MS m/z 610,612 (M+H)

Example 228

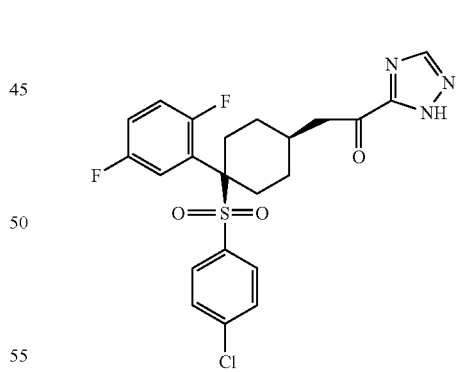

The triazole from Example 227 (0.117 g) was heated in a mixture of ethanol (10 ml) and 6M-HCl (aqueous) (5 ml) and concentrated HCl (2 ml) for 2 hours at 60° C. Water and ethyl acetate were added and the organic phase was dried (MgSO$_4$), evaporated in vacuo and the residue purified by chromatography on silica gel (eluting with 50% ethyl acetate in hexane, 100% ethyl acetate) to give the desired product as a solid which washed with hexane mp 147-154° C. MS m/z 480,482 (M+H). $^1$H NMR (360 MHz, CD$_4$OD) 1.51-1.60 (2H, m), 1.76 (2H, dd, J=14.3 Hz and 3.1 Hz), 2.37 (1H, m), 2.5 (4H m), 3.26 (2H, d, J=7.3 Hz), 6.96 (1H, m), 7.16 (2H, m), 7.40 (2H, dt, J=8.7 Hz and 2.23 Hz), 7.51 (2H, dt, J=8.7 Hz and 2.23 Hz), 8.51 (1H, s).

Example 229

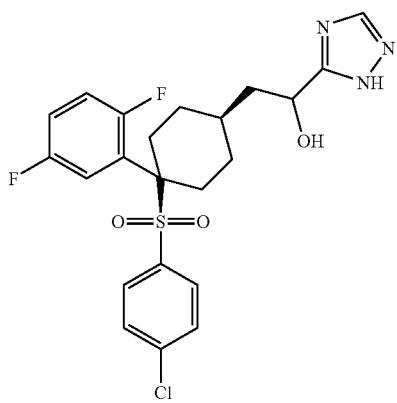

To a solution of the product of Example 228, (50 mg) in methanol (2 ml) was added sodium borohydride (4.5 mg 0.11 mmol). After 30 minutes ethyl acetate and water were added followed by addition of solid citric acid (50 mg). The organic phase was dried (MgSO$_4$), evaporated to dryness and the residue chromatographed on silica gel (eluting with ethyl acetate then 5% methanol in ethyl acetate) to give the desired product as a colourless solid after washing the residue with hexane. MS m/z 482, 484(M+H)). $^1$H NMR (360 MHz, CD$_4$OD) 1.43-1.54 (2H, m), 1.75-1.88 (3H, m), 1.54-2.0 (1H, m), 2.01-2.16 (1H,m), 2.35-2.55(5H,m), 6.93-7.00 (1H, m), 7.09-7.18 (2H, m), 7.37 (2H, d, J=8.6 Hz), 7.48 (2H,d, J=8.6 Hz), 8.1 (1H, v.broad s).

Example 230

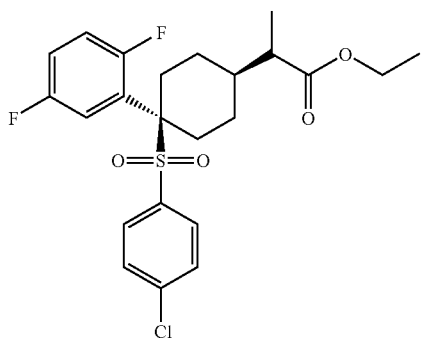

The ester from Example 48 (669 mg, 1.467 mmol) in tetrahydrofuran (14 ml) was cooled to −78° C., treated with sodium bis(trimethylsilyl)amide (2.20 ml, 1 M solution in tetrahydrofuran, 2.20 mmol) and stirred while warming to room temperature over 2 hours. Methyl iodide (457 µl, 7.36 mmol) was then added to the mixture at −20° C. and stirring continued, again warming to room temperature, for 2 hours. The reaction was quenched with glacial acetic acid (132 µl, 2.20 mmol), diluted with ammonium chloride (50% aq., 80 ml) and extracted with ethyl acetate (3×100 ml). Combined organics were then washed with brine (sat., 200 ml), dried (MgSO$_4$) and evaporated in vacuo to give crude (670 mg). This material was chromatographed on silica, eluting with 8% ethyl acetate in hexanes to give product (272 mg, 40%). $^1$H NMR (400 MHz, CDCl$_3$), 1.16 (3H, d, J=6.9 Hz), 1.28 (3H, t, J=7.1 Hz), 1.45-1.51 (2H, m), 1.71-1.77 (2H, m), 1.89-1.94 (1H, m), 2.28-2.48 (3H, br), 2.54-2.60 (1H, br), 2.70-2.74 (1H, m), Example 231

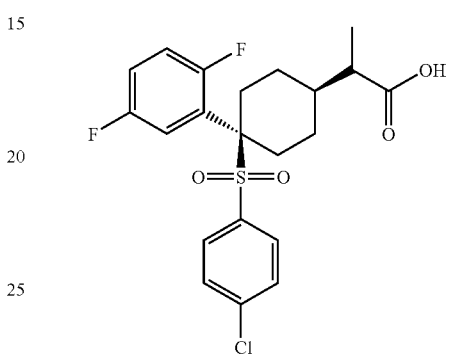

A solution of α-methyl ethyl ester from Example 230 (13 mg, 0.028 mmol) in methanol/water/tetrahydrofuran (3:1:1, 1 ml) was degassed and treated with lithium hydroxide (3.3 mg, 0.138 mmol) and the mixture heated to 90° C. After 1 hour at this temperature, the reaction was cooled to room temperature, acidified with hydrochloric acid (1 N, 2 ml), diluted with water (5 ml) and extracted with ethyl acetate (3×10 ml). Combined organics were washed with brine (sat., 30 ml), dried (MgSO$_4$) and evaporated in vacuo to give crude. This material was purified by preparative t.l.c., eluting with 3% methanol, 1% acetic acid in dichloromethane to give product (7 mg, 57%). $^1$H NMR (360 MHz, CDCl$_3$), 1.22 (3H, d, J=6.9 Hz), 1.48-1.58 (2H, m), 1.74-1.96 (3H, m), 2.30-2.50 (3H, br), 2.53-2.62 (1H, br), 2.71-2.81 (1H, m), 6.78-6.84 (1H, m), 7.00-7.09 (2H, m), 7.30-7.37 (4H, m).

Example 232

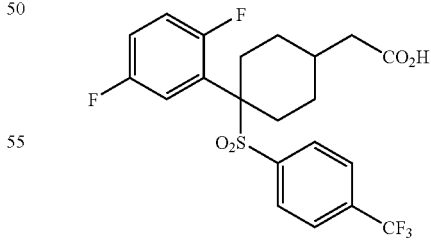

Prepared from the ketone of Example 41, following the procedures of Examples 47, 48 and 50. $^1$H NMR (360 MHz, CDCl$_3$) 1.52-1.61 (2H, m), 1.76-1.81 (2H, m), 2.20-2.26 (1H, m), 2.39 (2H, d, J=7.6 Hz), 2.40-2.50 (4H, m), 5.37 (1H, br), 5.51 (1H, br), 6.75-6.83 (1H, m), 7.01-7.08 (2H, m), 7.51 (2H, d, J=8.3 Hz) and 7.64 (2H, d, J=8.3 Hz).

Example 233

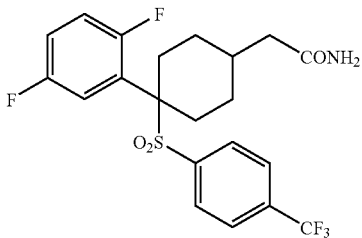

Prepared from the acid of Example 232 by the procedure of Example 178, using ammonia in the second step. MS MH+ 462(463).

The invention claimed is:

1. A compound of formula I:

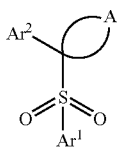

I wherein

A is selected from: —(CH$_2$)$_r$—O—(CH$_2$)$_s$— and (—CH$_2$)$_r$—NR$^1$—(CH$_2$)$_s$—, wherein r and s are 0-5 such that r+s is an integer in the range 2-5, said ring bearing, in addition to Ar$^2$ and Ar$^1$SO$_2$, 0-3 substituents independently selected from =X, halogen, CN, NO$_2$, N$_3$, R$^2$, CF$_3$, N(R$^1$)$_2$, OR$^1$, COR$^1$, CO$_2$R$^1$, CON(R$^1$)$_2$, OCOR$^1$, OCO$_2$R$^2$, OCON(R$^1$)$_2$, N(R$^1$)COR$^2$, N(R$^1$)CO$_2$R$^2$, OSO$_2$R$^2$ and N(R$^1$)SO$_2$R$^2$, except that the ring positions adjacent to the carbon bonded to the Ar$^1$SO$_2$ group are occupied by unsubstituted methylene groups;

X represents C(R$^1$)$_2$, CHCO$_2$R$^1$, O, S, NOR$^1$, CHCON (R$^1$)$_2$, NNHCOR$^2$, or the atoms necessary to complete a spiro-linked 5- or 6-membered carbocyclic or heterocyclic ring;

Ar$^1$ represents phenyl or pyridyl either of which bears 0-3 substituents independently selected from halogen, CN, NO$_2$, CF$_3$, OH, OCF$_3$, C$_{1-4}$alkoxy or C$_{1-4}$alkyl which optionally bears a substituent selected from halogen, CN, NO$_2$, CF$_3$, OH and C$_{1-4}$alkoxy;

Ar$^2$ represents phenyl, bearing 1 or 2 substituents independently selected from halogen, CN, NO$_2$, CF$_3$, OH, OCF$_3$, C$_{1-4}$alkoxy or C$_{1-4}$alkyl which optionally bears a substituent selected from halogen, CN, NO$_2$, CF$_3$, OH and C$_{1-4}$alkoxy;

R$^1$ represents H or R$^2$, or two R$^1$ groups together with a nitrogen atom to which they are mutually attached may complete an N-heterocyclyl group bearing 0-3 substituents selected from =O, =S, =NOR$^1$, halogen, CN, NO$_2$, R$^2$, CF$_3$, N(R$^{1a}$)$_2$, OR$^1$, COR$^1$, CO$_2$R$^1$ and CON(R$^{1a}$)$_2$;

R$^{1a}$ represents H or R$^2$, or two R$^{1a}$ groups together with a nitrogen atom to which they are mutually attached may complete an N-heterocyclyl group bearing 0-3 substituents selected from =O, =S, halogen, C$_{1-4}$alkyl CN, NO$_2$, CF$_3$, OH, C$_{1-4}$alkoxy, C$_{1-4}$alkoxycarbonyl, amino, C$_{1-4}$alkylamino, di(C$_{1-4}$alkyl)amino, carbamoyl, Ar and COAr;

R$^2$ represents C$_{1-6}$alkyl, C$_{3-9}$cycloalkyl, C$_{3-6}$cycloalkyl C$_{1-6}$alkyl, C$_{2-6}$alkenyl, C$_{2-6}$alkynyl or C-heterocyclyl, any of which may bear up to 3 substituents independently selected from halogen, CN, NO$_2$, N$_3$, CF$_3$, OR$^{2a}$, N(R$^{2a}$)$_2$, CO$_2$R$^{2a}$, COR$^{2a}$, OCOR$^{2a}$, CON(R$^{2a}$)$_2$, OCON(R$^{2a}$)$_2$, CONR$^{2a}$(OR$^{2a}$), CONHC(=NOH)R$^{2a}$, CON(R$^{2a}$)N(R$^{2a}$)$_2$, heterocyclyl, phenyl and heteroaryl, said heterocyclyl, phenyl and heteroaryl substituents themselves bearing 0-3 substituents selected from halogen, CN, NO$_2$, CF$_3$, OR$^{2a}$, N(R$^{2a}$)$_2$, CO$_2$R$^{2a}$, COR$^{2a}$, CON(R$^{2a}$)$_{2a}$ and C$_{1-4}$alkyl; or R$^2$ represents Ar; or 2 OR$^2$ groups attached to adjacent carbon atoms may complete a 1,3-dioxolane ring;

R$^{2a}$ represents H, C$_{1-6}$alkyl, C$_{3-6}$cycloalkyl, C$_{3-6}$cycloalkylC$_{1-6}$alkyl, C$_{2-6}$alkenyl, any of which optionally bears a substituent selected from halogen, CN, NO$_2$, CF$_3$, OR$^{2b}$, CO$_2$R$^{2b}$, N(R$^{2b}$)$_2$, CON(R$^{2b}$)$_2$, Ar and COAr; or R$^{2a}$ represents Ar; or two R$^{2a}$ groups together with a nitrogen atom to which they are mutually attached may complete an N-heterocyclyl group bearing 0-4 substituents independently selected from =O, =S, halogen, C$_{1-4}$alkyl, CN, NO$_2$, CF$_3$, OH, C$_{1-4}$alkoxy, C$_{1-4}$alkoxycarbonyl, CO$_2$H, amino, C$_{1-4}$alkylamino, di(C$_{1-4}$alkyl)amino, carbamoyl, Ar and COAr;

R$^{2b}$ represents H, C$_{1-6}$alkyl, C$_{3-6}$cycloalkyl, C$_{3-6}$cycloalkylC$_{1-6}$alkyl, C$_{2-6}$alkenyl, any of which optionally bears a substituent selected from halogen, CN, NO$_2$, CF$_3$, OH, C$_{1-4}$alkoxy, C$_{1-4}$alkoxycarbonyl, CO$_2$H, amino, C$_{1-4}$alkylamino, di(C$_{1-4}$alkyl)amino, carbamoyl, Ar and COAr; or R$^{2b}$ represents Ar; or two R$^{2b}$ groups together with a nitrogen atom to which they are mutually attached may complete an N-heterocyclyl group bearing 0-4 substituents independently selected from =O, =S, halogen, C$_{1-4}$alkyl, CN, NO$_2$, CF$_3$, OH, C$_{1-4}$alkoxy, C$_{1-4}$alkoxycarbonyl, CO$_2$H, amino, C$_{1-4}$alkylamino, di(C$_{1-4}$alkyl)amino, carbamoyl, Ar and COAr;

Ar represents phenyl or heteroaryl bearing 0-3 substituents selected from halogen, C$_{1-4}$alkyl, CN, NO$_2$, CF$_3$, OH, C$_{1-4}$alkoxy, C$_{1-4}$alkoxycarbonyl, amino, C$_{1-4}$alkylamino, di(C$_{1-4}$alkyl)amino, carbamoyl, C$_{1-4}$alkylcarbamoyl and di(C$_{1-4}$alkyl)carbamoyl;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

2. A compound according to claim 1 wherein each of r and s is at least 1.

3. A compound according to claim 1 wherein r+s is 3 or 4.

4. A compound according to claim 1 of formula IV, or a pharmaceutically acceptable salt thereof:

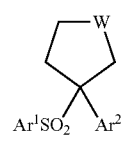

IV wherein:
W represents —NR⁶—(CH₂)ₜ— or —O—CHR⁷—;
R⁶ represents R¹, COR² or CO₂R²;
R⁷ H or OR¹; and
t is 0 or 1.
5. A compound which is selected from the group consisting of
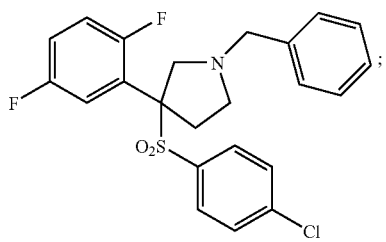
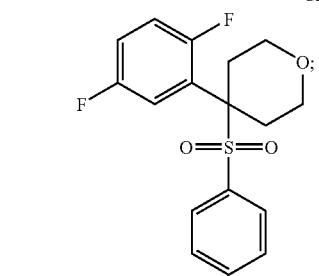
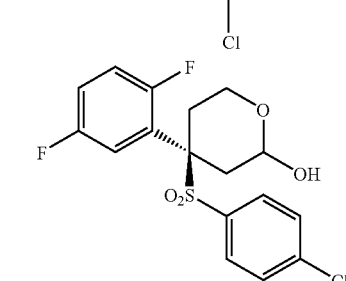
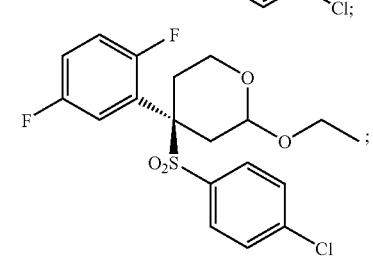
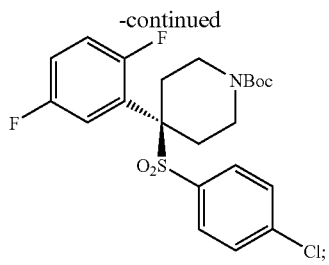
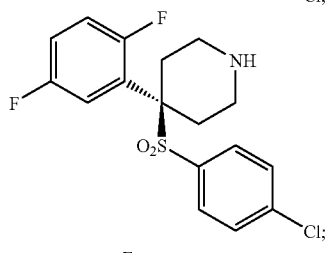
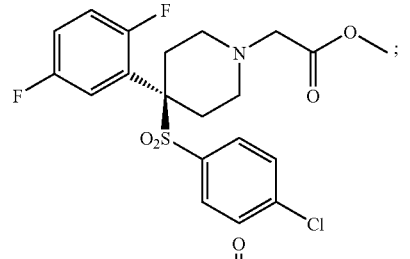
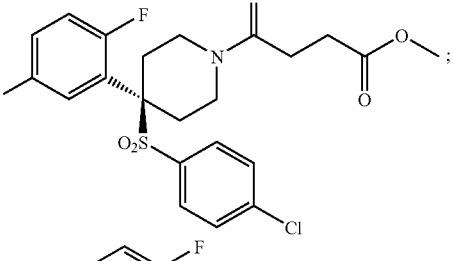
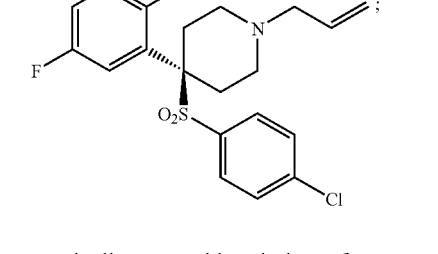
or a pharmaceutically acceptable salt thereof.
* * * * *